US007708701B2

(12) United States Patent
Boecker et al.

(10) Patent No.: US 7,708,701 B2
(45) Date of Patent: *May 4, 2010

(54) METHOD AND APPARATUS FOR A MULTI-USE BODY FLUID SAMPLING DEVICE

(75) Inventors: Dirk Boecker, Palo Alto, CA (US); Dominique M. Freeman, La Honda, CA (US); Michael Wittig, Santa Clara, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 1345 days.

This patent is subject to a terminal disclaimer.

(21) Appl. No.: 10/323,622

(22) Filed: Dec. 18, 2002

(65) Prior Publication Data
US 2004/0102803 A1 May 27, 2004

Related U.S. Application Data

(63) Continuation-in-part of application No. 10/127,395, filed on Apr. 19, 2002, now Pat. No. 7,025,774, and a continuation-in-part of application No. 10/237,261, filed on Sep. 5, 2002, now Pat. No. 7,344,507.

(60) Provisional application No. 60/393,706, filed on Jul. 1, 2002, provisional application No. 60/393,707, filed on Jul. 1, 2002, provisional application No. 60/422,988, filed on Nov. 1, 2002, provisional application No. 60/424,429, filed on Nov. 6, 2002, provisional application No. 60/428,084, filed on Nov. 20, 2002.

(51) Int. Cl.
*A61B 5/00* (2006.01)

(52) U.S. Cl. ...................................... 600/583; 606/181
(58) Field of Classification Search ......... 606/171–172, 606/181–186; 600/573, 583, 576, 577, 584
See application file for complete search history.

(56) References Cited

U.S. PATENT DOCUMENTS

| 2,801,633 | A | 8/1957 | Mauze et al | |
|---|---|---|---|---|
| 3,358,689 | A | 12/1967 | Higgins | 128/329 |
| 3,494,358 | A | 2/1970 | Grossenbacher | 128/218 |
| 3,626,929 | A | 12/1971 | Sanz | 128/2 R |
| 3,742,954 | A | 7/1973 | Strickland | 128/302 |
| 3,953,172 | A | 4/1976 | Shapiro | 23/230 |
| 4,224,125 | A | 9/1980 | Nakamura | 204/195 B |

(Continued)

FOREIGN PATENT DOCUMENTS

DE 29824204 10/2000

(Continued)

*Primary Examiner*—Michael J Milano
*Assistant Examiner*—Victor X Nguyen
(74) *Attorney, Agent, or Firm*—Paul Davis; Goodwin Procter LLP

(57) ABSTRACT

A device for use in penetrating tissue to obtain a body fluid sample is provided. A cartridge may be included. A plurality of penetrating members are slidably coupled to the cartridge. Each penetrating member has a distal end that is sufficiently sharp to pierce tissue. Each penetrating member may be moveable relative to the other ones of the penetrating members so that the sharpened distal ends extend radially outward to penetrate tissue. The penetrating members are elongate members without molded attachments.

13 Claims, 51 Drawing Sheets

U.S. PATENT DOCUMENTS

| | | | |
|---|---|---|---|
| 4,230,118 A | 10/1980 | Holman et al. | |
| 4,340,669 A | 7/1982 | Bauer | 435/14 |
| 4,353,984 A | 10/1982 | Yamada | 435/14 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,426,451 A | 1/1984 | Columbus | 436/518 |
| 4,426,884 A | 1/1984 | Polchaninoff | 73/172 |
| 4,469,110 A | 9/1984 | Slama | 128/770 |
| 4,517,978 A | 5/1985 | Levin | 128/314 |
| 4,539,988 A | 9/1985 | Shirley | 128/314 |
| 4,545,382 A | 10/1985 | Higgins | 128/635 |
| 4,553,541 A | 11/1985 | Burns | |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,637,403 A | 1/1987 | Garcia et al. | 128/770 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,787,398 A | 11/1988 | Garcia et al. | 128/770 |
| 4,794,926 A | 1/1989 | Munsch et al. | 606/183 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,824,639 A | 4/1989 | Hildenbrand | 422/56 |
| RE32,922 E | 5/1989 | Levin | 128/314 |
| 4,827,763 A | 5/1989 | Bourland | 73/172 |
| 4,830,959 A | 5/1989 | McNeill | 435/53 |
| 4,836,904 A | 6/1989 | Armstrong | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birch | 204/409 |
| 4,911,794 A | 3/1990 | Parce | 204/1 T |
| 4,920,977 A | 5/1990 | Haynes | 128/770 |
| 4,924,879 A | 5/1990 | O'Brien | |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | |
| 4,990,154 A | 2/1991 | Brown | 606/182 |
| 4,995,402 A | 2/1991 | Smith et al. | 128/771 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,026,388 A | 6/1991 | Ingalz | 606/182 |
| 5,054,499 A | 10/1991 | Swierczek | 128/770 |
| 5,059,789 A | 10/1991 | Salcudean | 250/206.1 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,145,565 A | 9/1992 | Kater et al. | 204/153.1 |
| 5,152,775 A | 10/1992 | Ruppert | 606/182 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,185,256 A | 2/1993 | Nankai | 435/174 |
| 5,187,100 A | 2/1993 | Matzinger | 436/16 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,217,480 A | 6/1993 | Haber | 606/182 |
| 5,229,282 A | 7/1993 | Yoshioka | 435/177 |
| 5,230,866 A | 7/1993 | Shartle | 422/103 |
| 5,231,993 A | 8/1993 | Haber et al. | |
| 5,250,066 A | 10/1993 | Lambert | 606/181 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,573 S | 12/1993 | Cerola | D24/147 |
| 5,272,087 A | 12/1993 | El Murr | 435/291 |
| 5,279,294 A | 1/1994 | Anderson et al. | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollman | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,316,012 A | 5/1994 | Siegal | 128/744 |
| 5,318,583 A | 6/1994 | Rabenau et al. | |
| 5,320,607 A | 6/1994 | Ishibashi | 604/115 |
| 5,324,302 A | 6/1994 | Crouse | 606/181 |
| 5,324,303 A | 6/1994 | Strong | 606/181 |
| 5,332,479 A | 7/1994 | Uenoyama | 204/153.12 |
| 5,350,392 A | 9/1994 | Purcell | 606/182 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,366,469 A | 11/1994 | Steg | 606/182 |
| 5,366,470 A | 11/1994 | Ramel | 606/183 |

| | | | | | | | |
|---|---|---|---|---|---|---|---|
| 5,366,609 A | 11/1994 | White | 204/403 | 5,683,562 A | 11/1997 | Schaffar | 204/403 |
| 5,375,397 A | 12/1994 | Ferrand | 54/66 | 5,695,947 A | 12/1997 | Guo | 435/11 |
| 5,378,628 A | 1/1995 | Graetzel | 435/288 | 5,700,695 A | 12/1997 | Yassinzadeh et al. | 436/180 |
| 5,382,346 A | 1/1995 | Uenoyama | 204/403 | 5,705,045 A | 1/1998 | Park | 204/403 |
| 5,383,885 A | 1/1995 | Bland | 606/182 | 5,708,247 A | 1/1998 | McAleer | 204/403 |
| 5,389,534 A | 2/1995 | Gentezkow | 435/180 | 5,709,668 A | 1/1998 | Wacks | 604/232 |
| 5,393,903 A | 2/1995 | Graetzel | 556/137 | 5,710,011 A | 1/1998 | Forrow | 435/25 |
| 5,395,387 A | 3/1995 | Burns | | 5,720,862 A | 2/1998 | Hamamoto | 204/403 |
| 5,397,334 A | 3/1995 | Schenk | 606/182 | 5,720,924 A | 2/1998 | Eikmeier et al. | 422/102 |
| 5,401,376 A | 3/1995 | Foos | 204/415 | D392,391 S | 3/1998 | Douglas | D24/225 |
| 5,402,798 A | 4/1995 | Swierczek | 128/770 | 5,723,284 A | 3/1998 | Ye | 435/4 |
| 5,407,545 A | 4/1995 | Hirose | 204/153.12 | 5,727,548 A | 3/1998 | Hill | 128/637 |
| 5,407,554 A | 4/1995 | Saurer | 204/403 | 5,730,753 A | 3/1998 | Morita | 606/181 |
| 5,407,818 A | 4/1995 | Gentezkow | 435/180 | 5,733,300 A | 3/1998 | Pambianchi | 606/181 |
| 5,409,583 A | 4/1995 | Yoshioka | 204/153.12 | D393,716 S | 4/1998 | Brenneman | D24/147 |
| 5,410,059 A | 4/1995 | Fraser | 546/10 | D393,717 S | 4/1998 | Brenneman | D24/147 |
| 5,423,847 A | 6/1995 | Strong et al. | 606/182 | 5,741,634 A | 4/1998 | Nozoe | 435/4 |
| 5,436,161 A | 7/1995 | Bergstrom | 435/291 | RE35,803 E | 5/1998 | Lange | 606/182 |
| 5,437,999 A | 8/1995 | Diebold | 435/288 | 5,746,217 A | 5/1998 | Erickson | 128/760 |
| 5,443,701 A | 8/1995 | Willner | 204/153 | 5,755,733 A | 5/1998 | Morita | 606/182 |
| 5,445,920 A | 8/1995 | Saito | 430/311 | 5,758,643 A | 6/1998 | Wong et al. | 128/632 |
| D362,719 S | 9/1995 | Kaplan | D24/147 | 5,759,364 A | 6/1998 | Charlton | 204/403 |
| 5,454,828 A | 10/1995 | Schraga | 606/182 | 5,762,770 A | 6/1998 | Pritchard | 204/403 |
| 5,456,875 A | 10/1995 | Lambert | 264/328.1 | 5,770,369 A | 6/1998 | Meade | 435/6 |
| 5,464,418 A | 11/1995 | Schraga | 606/182 | 5,772,586 A | 6/1998 | Heinonen | 600/300 |
| 5,471,102 A | 11/1995 | Becker | 310/50 | 5,772,677 A | 6/1998 | Mawhirt | 606/181 |
| 5,476,474 A | 12/1995 | Davis | 606/182 | 5,773,270 A | 6/1998 | D'Orazio | 435/177 |
| 5,480,387 A | 1/1996 | Gabriel | 604/134 | 5,776,157 A | 7/1998 | Thorne et al. | 606/182 |
| 5,487,748 A | 1/1996 | Marshall | 606/182 | 5,776,719 A | 7/1998 | Douglas | 435/28 |
| 5,496,453 A | 3/1996 | Uenoyama | 205/777.5 | 5,782,770 A | 7/1998 | Mooradian | 600/476 |
| 5,498,542 A | 3/1996 | Corey | 435/283.1 | 5,782,852 A | 7/1998 | Foggia | 606/182 |
| 5,509,410 A | 4/1996 | Hill | 128/637 | 5,788,652 A | 8/1998 | Rahn | 600/577 |
| 5,510,266 A | 4/1996 | Bonner et al. | | 5,795,725 A | 8/1998 | Buechler | 435/7.1 |
| 5,512,159 A | 4/1996 | Yoshioka | 204/403 | 5,795,774 A | 8/1998 | Matsumoto | 435/287.9 |
| 5,514,152 A | 5/1996 | Smith | 606/182 | 5,797,940 A | 8/1998 | Mawhirt | 606/167 |
| 5,518,006 A | 5/1996 | Mawhirt | 128/770 | 5,797,942 A | 8/1998 | Schraga | 606/182 |
| 5,524,636 A | 6/1996 | Sarvazyan | 128/774 | 5,798,030 A | 8/1998 | Raguse | 204/403 |
| 5,525,511 A | 6/1996 | D'Costa | 435/287.9 | 5,798,031 A | 8/1998 | Charlton | 204/403 |
| 5,527,333 A | 6/1996 | Nikkels | 606/182 | 5,800,781 A | 9/1998 | Gavin et al. | 422/73 |
| 5,527,334 A | 6/1996 | Kanner | 606/182 | 5,801,057 A | 9/1998 | Smart et al. | 436/68 |
| 5,540,709 A | 7/1996 | Ramel | 606/183 | 5,820,551 A | 10/1998 | Hill | 600/347 |
| 5,543,326 A | 8/1996 | Heller | 435/287.9 | 5,823,973 A | 10/1998 | Racchini et al. | 600/573 |
| 5,545,174 A | 8/1996 | Schenk | 606/182 | 5,824,491 A | 10/1998 | Priest | 435/28 |
| 5,547,702 A | 8/1996 | Gleisner | 427/2.13 | 5,840,020 A | 11/1998 | Heinonen | 600/309 |
| 5,554,166 A | 9/1996 | Lange | 606/182 | 5,840,171 A | 11/1998 | Birch | 205/335 |
| 5,558,834 A | 9/1996 | Chu | 422/55 | 5,846,490 A | 12/1998 | Yokota et al. | 422/66 |
| 5,569,286 A | 10/1996 | Peckham | 606/181 | 5,849,174 A | 12/1998 | Sanghera | 205/775 |
| 5,569,287 A | 10/1996 | Tezuka | 606/182 | 5,854,074 A | 12/1998 | Charlton et al. | 436/46 |
| 5,571,132 A | 11/1996 | Mawhirt | 606/182 | D403,975 S | 1/1999 | Douglas | D10/81 |
| 5,575,403 A | 11/1996 | Charlton et al. | 221/31 | 5,855,801 A | 1/1999 | Lin et al. | 216/2 |
| 5,575,895 A | 11/1996 | Ikeda | 204/403 | 5,857,983 A | 1/1999 | Douglas | 600/538 |
| 5,582,697 A | 12/1996 | Ikeda | 204/403 | 5,860,922 A | 1/1999 | Gordon et al. | 600/431 |
| 5,584,846 A | 12/1996 | Mawhirt | 606/181 | 5,863,800 A | 1/1999 | Eikmeier et al. | 436/48 |
| 5,593,852 A | 1/1997 | Heller | 435/14 | 5,866,353 A | 2/1999 | Berneth | 435/26 |
| 5,609,749 A | 3/1997 | Yamauchi | 205/777.5 | 5,868,772 A | 2/1999 | LeVaughn | 606/181 |
| 5,613,978 A | 3/1997 | Harding | 606/181 | 5,869,972 A | 2/1999 | Birch | 324/439 |
| 5,620,579 A | 4/1997 | Genshaw | 204/402 | 5,871,494 A | 2/1999 | Simons et al. | |
| 5,624,537 A | 4/1997 | Turner | 204/403 | 5,872,713 A | 2/1999 | Douglas | 702/85 |
| D379,516 S | 5/1997 | Rutter | D24/146 | 5,873,887 A | 2/1999 | King | 606/182 |
| 5,628,764 A | 5/1997 | Schraga | 606/182 | 5,876,957 A | 3/1999 | Douglas | 435/28 |
| 5,628,765 A | 5/1997 | Morita | 606/182 | 5,879,311 A | 3/1999 | Duchon et al. | 600/583 |
| 5,628,890 A | 5/1997 | Carter | 204/403 | 5,879,373 A | 3/1999 | Roeper | 606/344 |
| 5,632,410 A | 5/1997 | Moulton et al. | 221/79 | 5,882,494 A | 3/1999 | van Antwerp | 204/403 |
| 5,643,306 A | 7/1997 | Schraga | 606/182 | 5,891,053 A | 4/1999 | Sesekura | 600/583 |
| 5,645,555 A | 7/1997 | Davis | 606/182 | 5,900,130 A | 5/1999 | Benvegnu | 204/453 |
| 5,650,062 A | 7/1997 | Ikeda | 205/778 | 5,906,921 A | 5/1999 | Ikeda | 435/25 |
| 5,653,863 A | 8/1997 | Genshaw | 205/777.5 | D411,619 S | 6/1999 | Duchon | D24/146 |
| 5,657,760 A | 8/1997 | Ying et al. | 128/660.03 | 5,916,156 A | 6/1999 | Hildenbrand | 600/347 |
| 5,658,444 A | 8/1997 | Black | 204/415 | 5,916,229 A | 6/1999 | Evans | 606/171 |
| 5,662,127 A | 9/1997 | De Vaughn | 128/765 | 5,916,230 A | 6/1999 | Brenneman | 606/172 |
| 5,662,672 A | 9/1997 | Pambianchi | 606/181 | 5,921,963 A | 7/1999 | Erez | 604/192 |
| 5,680,872 A | 10/1997 | Sesekura | 128/760 | 5,922,188 A | 7/1999 | Ikeda | 204/777.5 |
| 5,682,884 A | 11/1997 | Hill | 128/637 | RE36,268 E | 8/1999 | Szuminsky | 205/777.5 |

| Patent | Type | Date | Inventor | Class |
|---|---|---|---|---|
| 5,935,075 | A | 8/1999 | Casscells et al. | 600/474 |
| 5,951,492 | A | 9/1999 | Douglas | 600/583 |
| 5,951,493 | A | 9/1999 | Douglas et al. | 600/583 |
| 5,951,582 | A | 9/1999 | Thorne et al. | 606/182 |
| 5,951,836 | A | 9/1999 | McAleer | 204/403 |
| 5,954,738 | A | 9/1999 | LeVaughn | 606/181 |
| 5,958,199 | A | 9/1999 | Miyamoto | 204/403 |
| 5,965,380 | A | 10/1999 | Heller | 435/14 |
| 5,972,199 | A | 10/1999 | Heller | 205/777.5 |
| 5,983,193 | A | 11/1999 | Heinonen | 705/2 |
| 5,985,116 | A | 11/1999 | Ikeda | 204/403 |
| 5,993,400 | A | 11/1999 | Rincoe | 600/595 |
| 5,997,561 | A | 12/1999 | Boecker | 606/182 |
| 5,997,817 | A | 12/1999 | Crismore | 422/58 |
| 5,997,818 | A | 12/1999 | Hackner | 422/681 |
| 6,001,067 | A | 12/1999 | Shults | 600/584 |
| 6,020,110 | A | 2/2000 | Williams | 430/315 |
| 6,022,324 | A | 2/2000 | Skinner | 600/566 |
| 6,022,366 | A | 2/2000 | Schraga | 606/181 |
| 6,027,459 | A | 2/2000 | Shain et al. | 600/573 |
| 6,030,399 | A | 2/2000 | Ignotz | 606/167 |
| 6,030,827 | A | 2/2000 | Davis | 435/287 |
| 6,033,421 | A | 3/2000 | Theiss | 606/186 |
| 6,033,866 | A | 3/2000 | Guo | 435/14 |
| 6,048,352 | A | 4/2000 | Douglas et al. | 606/181 |
| D424,696 | S | 5/2000 | Ray | D24/169 |
| 6,060,327 | A | 5/2000 | Keen | 436/518 |
| 6,063,039 | A | 5/2000 | Cunningham | 600/573 |
| 6,066,296 | A | 5/2000 | Brady | 422/63 |
| 6,067,463 | A | 5/2000 | Jeng | 600/336 |
| D426,638 | S | 6/2000 | Ray | D24/169 |
| 6,071,249 | A | 6/2000 | Cunningham | 600/578 |
| 6,071,250 | A | 6/2000 | Douglas | 600/583 |
| 6,071,251 | A | 6/2000 | Cunningham | 600/584 |
| 6,074,360 | A | 6/2000 | Haar et al. | 604/57 |
| 6,077,408 | A | 6/2000 | Miyamoto | 204/403 |
| 6,080,172 | A | 6/2000 | Fujiwara | 606/166 |
| 6,083,710 | A | 7/2000 | Heller | 435/14 |
| 6,086,562 | A | 7/2000 | Jacobsen | 604/156 |
| 6,090,078 | A | 7/2000 | Erskine | 604/198 |
| 6,093,156 | A | 7/2000 | Cunningham | |
| 6,103,033 | A | 8/2000 | Say | 156/73.1 |
| 6,107,083 | A | 8/2000 | Collins | 435/288 |
| 6,120,462 | A | 9/2000 | Hibner et al. | 600/566 |
| 6,120,676 | A | 9/2000 | Heller | 205/777.5 |
| 6,121,009 | A | 9/2000 | Heller | 435/14 |
| 6,129,823 | A | 10/2000 | Hughes | 204/403.01 |
| 6,133,837 | A | 10/2000 | Riley | 340/573.1 |
| 6,134,461 | A | 10/2000 | Say | 600/345 |
| 6,143,164 | A | 11/2000 | Heller et al. | 205/777.5 |
| 6,152,942 | A | 11/2000 | Brenneman et al. | 606/181 |
| 6,153,069 | A | 11/2000 | Pottgen | 204/403 |
| RE36,991 | E | 12/2000 | Yamamoto | 204/403 |
| 6,155,992 | A | 12/2000 | Henning et al. | 600/583 |
| 6,156,051 | A | 12/2000 | Schraga | 606/181 |
| 6,157,442 | A | 12/2000 | Raskas | 356/39 |
| 6,159,424 | A | 12/2000 | Kauhaniemi et al. | 422/63 |
| 6,162,611 | A | 12/2000 | Heller | 435/14 |
| 6,171,325 | B1 | 1/2001 | Mauze et al. | 356/446 |
| 6,175,752 | B1 | 1/2001 | Say | 600/345 |
| 6,176,865 | B1* | 1/2001 | Mauze et al. | 606/171 |
| 6,177,000 | B1 | 1/2001 | Peterson | 205/777.5 |
| 6,177,931 | B1 | 1/2001 | Alexander et al. | |
| 6,190,612 | B1 | 2/2001 | Berger | 422/82.07 |
| 6,191,852 | B1 | 2/2001 | Paffhausen | 356/244 |
| 6,192,891 | B1 | 2/2001 | Gravel | 128/920 |
| 6,194,900 | B1 | 2/2001 | Freeman | 324/321 |
| 6,197,257 | B1 | 3/2001 | Raskas | 422/82.05 |
| 6,206,841 | B1 | 3/2001 | Cunningham et al. | |
| 6,212,417 | B1 | 4/2001 | Ikeda | 204/403.14 |
| 6,214,804 | B1 | 4/2001 | Felgner | 514/44 |
| 6,221,238 | B1 | 4/2001 | Grundig | 205/777.5 |
| 6,225,078 | B1 | 5/2001 | Ikeda | 435/25 |
| 6,228,100 | B1 | 5/2001 | Schraga | |
| 6,230,501 | B1 | 5/2001 | Bailey | 62/51.1 |
| 6,241,862 | B1 | 6/2001 | McAleer | 204/403 |
| 6,245,060 | B1 | 6/2001 | Loomis | 606/9 |
| 6,251,260 | B1 | 6/2001 | Heller | 205/777.5 |
| 6,254,831 | B1 | 7/2001 | Barnard | 422/82.08 |
| 6,256,533 | B1 | 7/2001 | Vuzhakov | 604/21 |
| 6,258,229 | B1 | 7/2001 | Winarta | 204/403 |
| 6,258,254 | B1 | 7/2001 | Miyamoto | 205/777.5 |
| 6,261,519 | B1 | 7/2001 | Harding | |
| 6,268,161 | B1 | 7/2001 | Han | 435/14 |
| 6,270,637 | B1 | 8/2001 | Crismore | 204/403 |
| 6,272,359 | B1 | 8/2001 | Kivela | 455/567 |
| 6,281,006 | B1 | 8/2001 | Heller | 435/287.9 |
| 6,283,982 | B1 | 9/2001 | Levaughn | 606/172 |
| 6,284,478 | B1 | 9/2001 | Heller | 435/14 |
| 6,285,448 | B1 | 9/2001 | Kuenstner | 356/39 |
| 6,285,454 | B1 | 9/2001 | Douglas et al. | 356/446 |
| 6,290,683 | B1 | 9/2001 | Erez | 604/273 |
| 6,295,506 | B1 | 9/2001 | Heinonen | 702/104 |
| 6,299,757 | B1 | 10/2001 | Feldman | 205/775 |
| 6,302,855 | B1 | 10/2001 | Lav | 600/584 |
| 6,306,347 | B1 | 10/2001 | Mason | 422/58 |
| 6,309,535 | B1 | 10/2001 | Williams | 205/777.5 |
| 6,312,612 | B1 | 11/2001 | Sherman | 216/2 |
| 6,315,738 | B1 | 11/2001 | Nishikawa et al. | 600/583 |
| 6,319,210 | B1 | 11/2001 | Douglas et al. | 600/583 |
| 6,322,574 | B1 | 11/2001 | Lloyd | 606/181 |
| 6,331,163 | B1 | 12/2001 | Kaplan | 600/486 |
| 6,332,871 | B1 | 12/2001 | Douglas et al. | 600/583 |
| 6,334,363 | B1 | 1/2002 | Testud | 73/862 |
| 6,334,856 | B1 | 1/2002 | Allen | 604/191 |
| 6,338,790 | B1 | 1/2002 | Feldman | 205/777.5 |
| 6,350,273 | B1 | 2/2002 | Minagawa | 606/186 |
| 6,350,451 | B1 | 2/2002 | Horn | 424/184.1 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri et al. | 606/181 |
| 6,375,627 | B1 | 4/2002 | Mauze et al. | 600/584 |
| 6,379,301 | B1 | 4/2002 | Worthington | 600/309 |
| 6,379,324 | B1 | 4/2002 | Gartstein | 604/22 |
| 6,387,709 | B1 | 5/2002 | Mason | 436/164 |
| 6,399,394 | B1 | 6/2002 | Dahm | 436/180 |
| 6,409,740 | B1 | 6/2002 | Kuhr et al. | 606/182 |
| 6,413,410 | B1 | 7/2002 | Hodges | 205/775 |
| 6,413,411 | B1 | 7/2002 | Pottgen | 205/777.5 |
| 6,421,633 | B1 | 7/2002 | Heinonen | 703/11 |
| 6,428,664 | B1 | 8/2002 | Bhullar | 204/403.03 |
| 6,436,256 | B1 | 8/2002 | Williams | 204/403.06 |
| 6,436,721 | B1 | 8/2002 | Kuo | 436/514 |
| 6,440,645 | B1 | 8/2002 | Yon-Hin | 430/322 |
| 6,451,040 | B1 | 9/2002 | Purcell | 606/181 |
| 6,458,258 | B2 | 10/2002 | Taniike | 204/403 |
| 6,461,496 | B1 | 10/2002 | Feldman et al. | 205/777.5 |
| 6,462,162 | B2 | 10/2002 | van Antwerp | 528/77 |
| 6,471,903 | B2 | 10/2002 | Sherman | 264/328.1 |
| 6,475,436 | B1 | 11/2002 | Schabbach | 422/64 |
| 6,475,750 | B1 | 11/2002 | Han | 435/14 |
| 6,484,046 | B1 | 11/2002 | Say | 600/345 |
| 6,485,439 | B1 | 11/2002 | Roe et al. | 600/578 |
| 6,488,891 | B2 | 12/2002 | Mason et al. | 422/58 |
| 6,491,709 | B2 | 12/2002 | Sharma et al. | 606/181 |
| 6,497,845 | B1 | 12/2002 | Sacherer | 422/104 |
| 6,501,404 | B2 | 12/2002 | Walker | 341/143 |
| 6,503,210 | B1 | 1/2003 | Hirao et al. | 600/576 |
| 6,503,231 | B1 | 1/2003 | Prausnitz | 604/272 |
| 6,506,168 | B1 | 1/2003 | Fathallah | 600/578 |
| 6,506,575 | B1 | 1/2003 | Knappe et al. | 435/25 |
| 6,508,785 | B1 | 1/2003 | Eppstein | 604/113 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor | 206/305 |

| Patent No. | Date | Inventor | Class |
|---|---|---|---|
| 6,527,778 B2 | 3/2003 | Athanasiou | 606/80 |
| 6,530,892 B1 | 3/2003 | Kelly | |
| 6,530,937 B1 | 3/2003 | Schraga | 606/182 |
| 6,533,949 B1 | 3/2003 | Yeshurun | 216/11 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller et al. | 205/777.5 |
| 6,555,061 B1 | 4/2003 | Leong | 422/58 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,561,989 B2 | 5/2003 | Whitson | 600/573 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,576,101 B1 | 6/2003 | Heller | 204/403.14 |
| 6,576,416 B2 | 6/2003 | Haviland | 435/4 |
| 6,587,705 B1 | 7/2003 | Kim et al. | 600/347 |
| 6,589,260 B1 | 7/2003 | Schmelzeisen-Redeker et al. | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/72 |
| 6,641,533 B2 | 11/2003 | Causey | 600/300 |
| 6,645,368 B1 | 11/2003 | Beatty | 205/792 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-Redeker et al. | 600/583 |
| 6,706,000 B2 | 3/2004 | Perez | 600/583 |
| 6,706,159 B2 | 3/2004 | Moerman | 204/403.03 |
| 6,706,232 B2 | 3/2004 | Hasegawa | 264/403.09 |
| 6,713,660 B2 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Nakaminami et al. | 204/403.14 |
| 6,743,211 B1 | 6/2004 | Prausnitz | 604/239 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 * | 8/2004 | Kuhr et al. | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda et al. | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips et al. | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,847,451 B2 | 1/2005 | Pugh | 356/436 |
| 6,849,052 B2 | 2/2005 | Uchigaki et al. | 600/584 |
| 6,849,168 B2 | 2/2005 | Crumly et al. | 204/416 |
| 6,849,216 B2 | 2/2005 | Rappin | 264/134 |
| 6,850,790 B2 | 2/2005 | Berner | 600/347 |
| 2001/0017269 A1 | 8/2001 | Heller | 205/777.5 |
| 2001/0027328 A1 | 10/2001 | Lum | 606/186 |
| 2001/0054319 A1 | 12/2001 | Heller | 73/849 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum et al. | |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |

| | | | | | | |
|---|---|---|---|---|---|---|
| 2002/0057993 A1 | 5/2002 | Maisey ............... 422/82.01 | | 2003/0199912 A1 | 10/2003 | Pugh ..................... 606/182 |
| 2002/0076349 A1 | 6/2002 | Aitken ................... 422/58 | | 2003/0201194 A1 | 10/2003 | Heller .................. 205/777.5 |
| 2002/0078091 A1 | 6/2002 | Vu ........................ 707/513 | | 2003/0203352 A1 | 10/2003 | Haviland ................ 435/4 |
| 2002/0081588 A1 | 6/2002 | Lumley-Woodyear ....... 435/6 | | 2003/0206828 A1 | 11/2003 | Bell ........................ 422/44 |
| 2002/0084196 A1 | 7/2002 | Liamos .................. 205/792 | | 2003/0208140 A1 | 11/2003 | Pugh .................... 600/584 |
| 2002/0087056 A1 | 7/2002 | Aceti | | 2003/0212344 A1 | 11/2003 | Yuzhakov ............... 600/583 |
| 2002/0092612 A1 | 7/2002 | Davies .................. 156/292 | | 2003/0212345 A1 | 11/2003 | McAllister ............. 600/584 |
| 2002/0120216 A1 | 8/2002 | Fritz ..................... 600/583 | | 2003/0212346 A1 | 11/2003 | McAllister et al. ......... 600/584 |
| 2002/0130042 A1 | 9/2002 | Moerman ............ 204/403.01 | | 2003/0212347 A1 | 11/2003 | Sohrab .................. 600/584 |
| 2002/0136667 A1 | 9/2002 | Subramanian ............. 422/100 | | 2003/0212423 A1 | 11/2003 | Pugh .................... 606/181 |
| 2002/0136863 A1 | 9/2002 | Subramanian et al. ...... 428/156 | | 2003/0212424 A1 | 11/2003 | Briggs .................. 606/181 |
| 2002/0137998 A1 | 9/2002 | Smart ................... 600/347 | | 2003/0216767 A1 | 11/2003 | List ..................... 606/181 |
| 2002/0148739 A2 | 10/2002 | Liamos .................. 205/787 | | 2003/0217918 A1 | 11/2003 | Davies ................. 204/403.14 |
| 2002/0160520 A1 | 10/2002 | Orloff ...................... 436/72 | | 2003/0220552 A1 | 11/2003 | Reghabi .................. 600/365 |
| 2002/0161289 A1 | 10/2002 | Hopkins .................. 600/322 | | 2003/0220663 A1 | 11/2003 | Fletcher .................. 606/182 |
| 2002/0168290 A1 | 11/2002 | Yuzhakov .................. 422/56 | | 2003/0223906 A1 | 12/2003 | McAllister ............... 422/58 |
| 2002/0176984 A1 | 11/2002 | Smart ................... 428/336 | | 2003/0225429 A1 | 12/2003 | Garthe .................. 606/182 |
| 2002/0177761 A1 | 11/2002 | Orloff .................... 600/309 | | 2003/0225430 A1 | 12/2003 | Schraga ................. 606/182 |
| 2002/0188224 A1 | 12/2002 | Roe ..................... 600/584 | | 2003/0228637 A1 | 12/2003 | Wang ................... 435/7.9 |
| 2003/0018282 A1 | 1/2003 | Effenhauser ............ 600/583 | | 2003/0232370 A1 | 12/2003 | Trifiro ..................... 435/6 |
| 2003/0018300 A1 | 1/2003 | Duchon ................ 604/164.01 | | 2003/0233055 A1 | 12/2003 | Erickson ................ 600/573 |
| 2003/0028126 A1 | 2/2003 | List ..................... 600/583 | | 2003/0233112 A1 | 12/2003 | Alden et al. .............. 606/181 |
| 2003/0050573 A1 | 3/2003 | Kuhr .................... 600/567 | | 2003/0233113 A1 | 12/2003 | Alden et al. .............. 606/182 |
| 2003/0050656 A1 | 3/2003 | Schraga ................ 606/182 | | 2004/0006285 A1 | 1/2004 | Douglas ................. 600/583 |
| 2003/0060730 A1 | 3/2003 | Perez ................... 600/576 | | 2004/0007585 A1 | 1/2004 | Griffith .................. 221/232 |
| 2003/0073089 A1 | 4/2003 | Mauze .................... 435/6 | | 2004/0009100 A1 | 1/2004 | Simons .................. 422/102 |
| 2003/0073229 A1 | 4/2003 | Greenstein .............. 435/287.2 | | 2004/0010279 A1 | 1/2004 | Freeman ................ 606/182 |
| 2003/0073931 A1 | 4/2003 | Boecker ................. 600/573 | | 2004/0015064 A1 | 1/2004 | Parsons ................. 600/347 |
| 2003/0083685 A1 | 5/2003 | Freeman et al. | | 2004/0019250 A1 | 1/2004 | Catelli ..................... 600/1 |
| 2003/0083686 A1 | 5/2003 | Freeman ................ 606/181 | | 2004/0026243 A1 | 2/2004 | Davies ................. 204/403.14 |
| 2003/0088191 A1 | 5/2003 | Freeman et al. ............ 600/583 | | 2004/0030353 A1 | 2/2004 | Schmelzeisen-Redeker . 606/201 |
| 2003/0089730 A1 | 5/2003 | May ..................... 221/232 | | 2004/0031682 A1 | 2/2004 | Wilsey .................. 204/403.1 |
| 2003/0093010 A1 | 5/2003 | Essenpreis ............... 600/583 | | 2004/0034318 A1 | 2/2004 | Fritz ....................... 604/19 |
| 2003/0100040 A1 | 5/2003 | Bonnecaze ................ 435/14 | | 2004/0038045 A1 | 2/2004 | Smart ................... 428/446 |
| 2003/0106810 A1 | 6/2003 | Douglas ................. 205/777.5 | | 2004/0039303 A1 | 2/2004 | Wurster |
| 2003/0109777 A1 | 6/2003 | Kloepfer ................ 600/367 | | 2004/0039342 A1 | 2/2004 | Eppstein ................. 604/200 |
| 2003/0111357 A1 | 6/2003 | Black .................... 205/775 | | 2004/0039407 A1 | 2/2004 | Schraga ................. 606/181 |
| 2003/0113827 A1 | 6/2003 | Burkoth .................. 435/14 | | 2004/0039408 A1 | 2/2004 | Abulhaj ................. 606/181 |
| 2003/0116447 A1 | 6/2003 | Sturridge ............... 205/777.5 | | 2004/0049220 A1 | 3/2004 | Boecker ................. 606/181 |
| 2003/0135333 A1 | 7/2003 | Aceti ..................... 702/31 | | 2004/0054267 A1 | 3/2004 | Feldman ................ 600/316 |
| 2003/0143113 A2 | 7/2003 | Yuzhakov .................. 422/56 | | 2004/0055898 A1 | 3/2004 | Heller .................. 205/777.5 |
| 2003/0144608 A1 | 7/2003 | Kojima .................. 600/583 | | 2004/0059256 A1 | 3/2004 | Perez ................... 600/583 |
| 2003/0144609 A1 | 7/2003 | Kennedy ................ 600/583 | | 2004/0060818 A1 | 4/2004 | Feldman ............... 204/403.01 |
| 2003/0146110 A1 | 8/2003 | Karinka ................. 205/777.5 | | 2004/0061841 A1 | 4/2004 | Black ...................... 355/30 |
| 2003/0149348 A1 | 8/2003 | Raskas .................. 600/310 | | 2004/0064068 A1 | 4/2004 | DeNuzzio ................ 600/583 |
| 2003/0149377 A1 | 8/2003 | Erickson ................ 600/573 | | 2004/0092995 A1 | 5/2004 | Boecker ................. 606/181 |
| 2003/0153900 A1 | 8/2003 | Aceti ................... 604/890.1 | | 2004/0096991 A1 | 5/2004 | Zhang ................... 436/518 |
| 2003/0191415 A1 | 10/2003 | Moerman ................ 600/584 | | 2004/0098010 A1 | 5/2004 | Davison ................. 606/181 |
| 2003/0195435 A1 | 10/2003 | Williams ................. 600/583 | | 2004/0102803 A1 | 5/2004 | Boecker ................. 606/183 |
| 2003/0195540 A1 | 10/2003 | Moerman ................ 606/181 | | 2004/0106858 A1 | 6/2004 | Say ..................... 600/345 |
| 2003/0199744 A1 | 10/2003 | Buse .................... 600/347 | | 2004/0106859 A1 | 6/2004 | Say ..................... 600/345 |
| 2003/0199789 A1 | 10/2003 | Boecker ................. 600/575 | | 2004/0106860 A1 | 6/2004 | Say ..................... 600/345 |
| 2003/0199790 A1 | 10/2003 | Boecker ................. 600/576 | | 2004/0106904 A1 | 6/2004 | Gonnelli ................. 604/173 |
| 2003/0199791 A1 | 10/2003 | Boecker ................. 600/576 | | 2004/0106941 A1 | 6/2004 | Roe ..................... 606/181 |
| 2003/0199891 A1 | 10/2003 | Argauer ................. 606/181 | | 2004/0115754 A1 | 6/2004 | Chang .................... 435/14 |
| 2003/0199893 A1 | 10/2003 | Boecker ................. 606/181 | | 2004/0115831 A1 | 6/2004 | Meathrel ................. 436/514 |
| 2003/0199894 A1 | 10/2003 | Boecker ................. 606/181 | | 2004/0116829 A1 | 6/2004 | Raney ................... 600/573 |
| 2003/0199896 A1 | 10/2003 | Boecker ................. 606/181 | | 2004/0122339 A1 | 6/2004 | Roe |
| 2003/0199897 A1 | 10/2003 | Boecker ................. 606/181 | | 2004/0127818 A1 | 7/2004 | Roe ..................... 600/583 |
| 2003/0199898 A1 | 10/2003 | Boecker ................. 606/181 | | 2004/0127819 A1 | 7/2004 | Roe ..................... 600/583 |
| 2003/0199899 A1 | 10/2003 | Boecker ................. 606/181 | | 2004/0127928 A1 | 7/2004 | Whitson ................. 606/181 |
| 2003/0199900 A1 | 10/2003 | Boecker ................. 606/181 | | 2004/0127929 A1 | 7/2004 | Roe ..................... 606/181 |
| 2003/0199901 A1 | 10/2003 | Boecker ................. 606/181 | | 2004/0132167 A1 | 7/2004 | Rule ................... 435/287.1 |
| 2003/0199902 A1 | 10/2003 | Boecker ................. 606/181 | | 2004/0133125 A1 | 7/2004 | Miyashita ................ 600/573 |
| 2003/0199903 A1 | 10/2003 | Boecker ................. 606/181 | | 2004/0133127 A1 | 7/2004 | Roe ..................... 600/583 |
| 2003/0199904 A1 | 10/2003 | Boecker ................. 606/181 | | 2004/0138541 A1 | 7/2004 | Ward ................... 600/345 |
| 2003/0199905 A1 | 10/2003 | Boecker ................. 606/181 | | 2004/0138588 A1 | 7/2004 | Saikley ................. 600/583 |
| 2003/0199906 A1 | 10/2003 | Boecker ................. 606/181 | | 2004/0138688 A1 | 7/2004 | Giraud .................. 606/181 |
| 2003/0199907 A1 | 10/2003 | Boecker ................. 606/181 | | 2004/0146958 A1 | 7/2004 | Bae ....................... 435/14 |
| 2003/0199908 A1 | 10/2003 | Boecker ................. 606/181 | | 2004/0154932 A1 | 8/2004 | Deng .................. 205/777.5 |
| 2003/0199909 A1 | 10/2003 | Boecker ................. 606/181 | | 2004/0157017 A1 | 8/2004 | Mauze ................... 428/35.7 |
| 2003/0199910 A1 | 10/2003 | Boecker ................. 606/181 | | 2004/0157149 A1 | 8/2004 | Hofmann ................ 430/131 |
| 2003/0199911 A1 | 10/2003 | Boecker ................. 606/181 | | 2004/0157319 A1 | 8/2004 | Keen ................... 435/287.2 |

| Pub. No. | Date | Inventor | Class |
|---|---|---|---|
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Yang et al. | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1* | 1/2005 | Kuhr et al. | 606/181 |
| 2005/0027181 A1 | 2/2005 | Goode et al. | |

FOREIGN PATENT DOCUMENTS

| | | |
|---|---|---|
| DE | 10032042 | 1/2002 |
| DE | 10057832 | 2/2002 |
| DE | 10142232 | 3/2003 |
| EP | 0199484 A2 | 10/1986 |
| EP | 0289 269 A3 | 11/1988 |
| EP | 0320109 A1 | 6/1989 |
| EP | 0170375 B1 | 5/1990 |
| EP | 0136362 | 12/1990 |
| EP | 0453283 | 10/1991 |
| EP | 0374355 B1 | 6/1993 |
| EP | 0351891 B1 | 9/1993 |
| EP | 0593096 A2 | 4/1994 |
| EP | 0415388 B1 | 5/1995 |
| EP | 0505494 B1 | 7/1995 |
| EP | 0359831 | 8/1995 |
| EP | 0471986 B1 | 10/1995 |
| EP | 0368474 B1 | 12/1995 |
| EP | 0461601 B1 | 12/1995 |
| EP | 0429076 | 1/1996 |
| EP | 0552223 B1 | 7/1996 |
| EP | 0735363 | 10/1996 |
| EP | 0505504 B1 | 3/1997 |

| | | | | | | |
|---|---|---|---|---|---|---|
| EP | 0593096 A3 | 3/1997 | | WO | WO 98/20348 | 5/1998 |
| EP | 0406304 | 8/1997 | | WO | WO 98/24366 A2 | 6/1998 |
| EP | 0537761 | 8/1997 | | WO | WO 98/24366 A3 | 6/1998 |
| EP | 0795601 | 9/1997 | | WO | WO 98/24373 | 6/1998 |
| EP | 0795601 A3 | 9/1997 | | WO | WO 98/35225 | 8/1998 |
| EP | 0562370 | 11/1997 | | WO | WO 99/03584 | 1/1999 |
| EP | 0415393 B1 | 12/1997 | | WO | WO 99/05966 | 2/1999 |
| EP | 0560336 | 5/1998 | | WO | WO 99/07431 A1 | 2/1999 |
| EP | 0289 269 A2 | 11/1998 | | WO | WO 99/13100 | 3/1999 |
| EP | 0878 708 | 11/1998 | | WO | WO 99/19507 | 4/1999 |
| EP | 0505475 B1 | 3/1999 | | WO | WO 99/19717 | 4/1999 |
| EP | 0901018 | 3/1999 | | WO | WO 99/27852 | 6/1999 |
| EP | 0470649 B1 | 6/1999 | | WO | WO 99/62576 | 12/1999 |
| EP | 0 951 939 | 10/1999 | | WO | WO 99/64580 | 12/1999 |
| EP | 0847447 | 11/1999 | | WO | WO 00/09184 | 2/2000 |
| EP | 0964059 | 12/1999 | | WO | WO 00/30186 | 5/2000 |
| EP | 0969097 A2 | 1/2000 | | WO | WO 00/39914 | 7/2000 |
| EP | 0 985 376 | 5/2000 | | WO | WO 00/44084 A2 | 7/2000 |
| EP | 1021950 | 7/2000 | | WO | WO 00/44084 A3 | 7/2000 |
| EP | 0894869 | 2/2001 | | WO | WO 00/50771 | 8/2000 |
| EP | 1074832 | 2/2001 | | WO | WO 00/60340 | 10/2000 |
| EP | 1093854 | 4/2001 | | WO | WO 00/64022 | 10/2000 |
| EP | 1 101 443 | 5/2001 | | WO | WO 00/67245 | 11/2000 |
| EP | 1101443 | 5/2001 | | WO | WO 00/67268 | 11/2000 |
| EP | 1114995 A2 | 7/2001 | | WO | WO 01/00090 | 1/2001 |
| EP | 0736607 | 8/2001 | | WO | WO 01/75433 | 3/2001 |
| EP | 0969097 A3 | 8/2001 | | WO | WO 01/23885 A1 | 4/2001 |
| EP | 0730037 | 12/2001 | | WO | WO 01/23885 A3 | 4/2001 |
| EP | 0636879 | 1/2002 | | WO | WO 01/25775 | 4/2001 |
| EP | 0851224 | 3/2002 | | WO | WO 01/26813 | 4/2001 |
| EP | 0856586 | 5/2002 | | WO | WO 01/26813 A3 | 4/2001 |
| EP | 0817809 | 7/2002 | | WO | WO 01/33216 | 5/2001 |
| EP | 0872728 | 7/2002 | | WO | WO 01/34029 | 5/2001 |
| EP | 0795748 | 8/2002 | | WO | WO 01/36955 | 5/2001 |
| EP | 0685737 | 9/2002 | | WO | WO 01/40788 | 7/2001 |
| EP | 1114995 A3 | 10/2003 | | WO | WO 01/57510 A2 | 8/2001 |
| EP | 0880692 | 1/2004 | | WO | WO 01/57510 A3 | 8/2001 |
| EP | 1246688 | 5/2004 | | WO | WO 01/64105 A1 | 9/2001 |
| FR | 2 555 432 A | 5/1985 | | WO | WO 01/66010 | 9/2001 |
| GB | 2168815 | 6/1986 | | WO | WO 01/72220 A | 10/2001 |
| GB | 233936 A | 6/1999 | | WO | WO 01/72225 A1 | 10/2001 |
| GB | 2335860 A | 10/1999 | | WO | WO 01/73124 A2 | 10/2001 |
| GB | 2335990 A | 10/1999 | | WO | WO 01/73124 A3 | 10/2001 |
| JP | 2-326247 | 11/1990 | | WO | WO 01/73395 | 10/2001 |
| JP | 9-276235 | 10/1997 | | WO | WO 01/89691 | 11/2001 |
| JP | 10-296325 | 10/1998 | | WO | WO 01/89691 A3 | 11/2001 |
| WO | WO 80/01389 | 7/1980 | | WO | WO 02/00101 | 1/2002 |
| WO | WO 8504089 | 9/1985 | | WO | WO 02/02796 | 1/2002 |
| WO | WO 86/07632 | 12/1985 | | WO | WO 02/08750 | 1/2002 |
| WO | WO 91/09139 | 6/1991 | | WO | WO 02/08753 A2 | 1/2002 |
| WO | WO 93/02720 | 2/1993 | | WO | WO 02/08753 A3 | 1/2002 |
| WO | WO 93/06979 | 4/1993 | | WO | WO 02/08950 | 1/2002 |
| WO | WO 93/12726 | 7/1993 | | WO | WO 02/18940 A2 | 3/2002 |
| WO | WO 93/25898 | 12/1993 | | WO | WO 02/18940 A3 | 3/2002 |
| WO | WO 94/27140 | 11/1994 | | WO | WO 02/32559 | 4/2002 |
| WO | WO 94/29703 | 12/1994 | | WO | WO 02/41779 | 5/2002 |
| WO | WO 94/29704 | 12/1994 | | WO | WO 02/44948 | 6/2002 |
| WO | WO 94/29731 | 12/1994 | | WO | WO 02/059734 | 8/2002 |
| WO | WO 95/00662 | 1/1995 | | WO | WO 02/069791 | 9/2002 |
| WO | WO 95/10223 A2 | 4/1995 | | WO | WO 02/077638 A2 | 10/2002 |
| WO | WO 95/10223 A3 | 4/1995 | | WO | WO 02/077638 A3 | 10/2002 |
| WO | WO 95/22597 | 8/1995 | | WO | WO 02/100251 | 12/2002 |
| WO | WO 96/30431 | 10/1996 | | WO | WO 02/100252 | 12/2002 |
| WO | WO 97/02359 | 1/1997 | | WO | WO 02/100253 | 12/2002 |
| WO | WO 97/02487 | 1/1997 | | WO | WO 02/100254 | 12/2002 |
| WO | WO 97/18464 | 5/1997 | | WO | WO 02/100460 | 12/2002 |
| WO | WO 97/30344 | 8/1997 | | WO | WO 02/100461 | 12/2002 |
| WO | WO 97/42882 | 11/1997 | | WO | WO 02/101343 | 12/2002 |
| WO | WO 97/42888 | 11/1997 | | WO | WO 02/101359 | 12/2002 |
| WO | WO 97/45720 | 12/1997 | | WO | WO 03/000321 | 1/2003 |
| WO | WO 98/03431 | 1/1998 | | WO | WO 03/023389 A2 | 3/2003 |
| WO | WO 98/19159 | 5/1998 | | WO | WO 03/023389 A3 | 3/2003 |
| WO | WO 98/20332 | 5/1998 | | WO | WO 03/042691 | 5/2003 |

| | | |
|---|---|---|
| WO | WO 03/045557 A2 | 6/2003 |
| WO | WO 03/045557 A3 | 6/2003 |
| WO | WO 03/046542 A2 | 6/2003 |
| WO | WO 03/046542 A3 | 6/2003 |
| WO | WO 03/049609 | 6/2003 |
| WO | WO 03/050534 | 6/2003 |
| WO | WO 03/066128 A2 | 8/2003 |
| WO | WO 03/066128 A3 | 8/2003 |
| WO | WO 03/070099 | 8/2003 |
| WO | WO 03/071940 | 9/2003 |
| WO | WO 03/088851 A1 | 10/2003 |
| WO | WO 2004/008130 | 1/2004 |
| WO | WO 2004/026130 | 4/2004 |
| WO | WO 2004/041082 | 5/2004 |
| WO | WO 2004/054455 | 7/2004 |
| WO | WO 2004/060174 | 7/2004 |
| WO | WO 2004/060446 | 7/2004 |
| WO | WO 2004/091693 | 10/2004 |
| WO | WO 2004/107964 | 12/2004 |
| WO | WO 2004/107975 | 12/2004 |
| WO | WO 2004/112602 | 12/2004 |
| WO | WO 2005/001418 | 1/2005 |

* cited by examiner

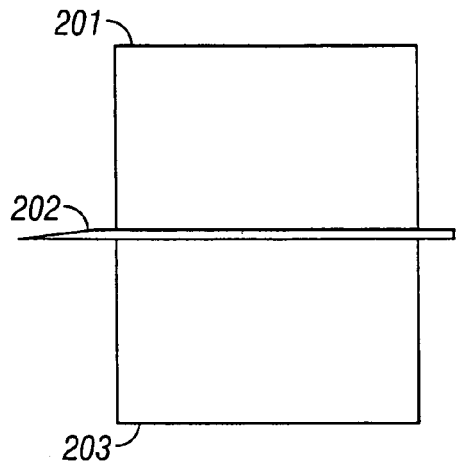
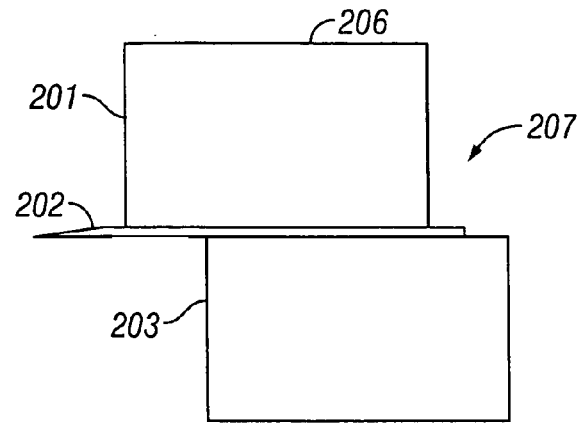
FIG. 12          FIG. 13
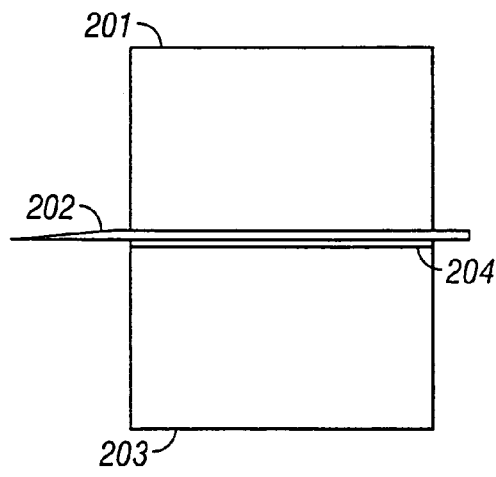
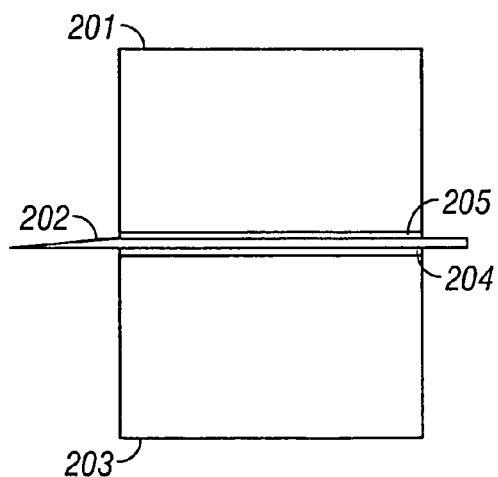
FIG. 14          FIG. 15

METHOD AND APPARATUS FOR A MULTI-USE BODY FLUID SAMPLING DEVICE

RELATED APPLICATIONS

This application is a continuation-in-part, and claims priority under 35 USC §120 to commonly assigned, copending, U.S. patent application Ser. No. 10/127,395 filed Apr. 19, 2002 now U.S. Pat. No. 7,025,774. This application is also a continuation-in-part, and claims priority under 35 USC §120 to commonly assigned, copending U.S. patent application Ser. No. 10/237,261 filed Sep. 5, 2002 now U.S. Pat. No. 7,344,507. The present application also claims the benefit of priority under 35 USC §119(e) to commonly assigned, copending U.S. Provisional Patent Application Ser. No. 60/393,706 filed Jul. 1, 2002; commonly assigned, copending U.S. Provisional Patent Application Ser. No. 60/393,707 filed Jul. 1, 2002; commonly assigned, copending U.S. Provisional Patent Application Ser. No. 60/422,988 filed Nov. 1, 2002; commonly assigned, copending U.S. Provisional Patent Application Ser. No. 60/424,429 filed Nov. 6, 2002; and commonly assigned, copending U.S. Provisional Patent Application Ser. No. 60/428,084 filed Nov. 20, 2002. All applications listed above are incorporated herein by reference for all purposes.

BACKGROUND OF THE INVENTION

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Another impediment to patient compliance is the lack of spontaneous blood flow generated by known lancing technology. In addition to the pain as discussed above, a patient may need more than one lancing event to obtain a blood sample since spontaneous blood generation is unreliable using known lancing technology. Thus the pain is multiplied by the number of attempts required by a patient to successfully generate spontaneous blood flow. Different skin thickness may yield different results in terms of pain perception, blood yield and success rate of obtaining blood between different users of the lancing device. Known devices poorly account for these skin thickness variations.

A still further impediment to improved compliance with glucose monitoring are the many steps and inconvenience associated with each lancing event. Many diabetic patients that are insulin dependent may need to self-test for blood glucose levels five to six times daily. The large number of steps required in traditional methods of glucose testing, ranging from lancing, to milking of blood, applying blood to a test strip, and getting the measurements from the test strip, discourages many diabetic patients from testing their blood glucose levels as often as recommended. Older patients and those with deteriorating motor skills encounter difficulty loading lancets into launcher devices, transferring blood onto a test strip, or inserting thin test strips into slots on glucose measurement meters. Additionally, the wound channel left on the patient by known systems may also be of a size that discourages those who are active with their hands or who are worried about healing of those wound channels from testing their glucose levels.

SUMMARY OF THE INVENTION

The present invention provides solutions for at least some of the drawbacks discussed above. Specifically, some embodiments of the present invention provide a multiple lancet solution to measuring analyte levels in the body. The invention may use a high density design. At least some of these and other objectives described herein will be met by embodiments of the present invention.

In one aspect of the present invention, a device for use in penetrating tissue to obtain a body fluid sample is provided. A cartridge may be included. A plurality of penetrating members are slidably coupled to the cartridge. Each penetrating member has a distal end that is sufficiently sharp to pierce tissue. Each penetrating member is moveable relative to the other ones of the penetrating members so that the sharpened distal ends extend radially outward to penetrate tissue. The penetrating members are elongate members without molded attachments.

In another embodiment of the present invention, a device is provided for use in penetrating tissue to obtain a body fluid sample. A cartridge is included that has a plurality of cavities. A plurality of bare lancets each have sharpened tips and are slidably coupled to the cartridge. Each of the bare lancets is moveable relative to the other ones of the bare lancets along a path out of the cartridge to penetrate tissue. The bare lancets are arranged with the sharpened tips pointing radially outward. Each of the cavities is defined in part by a deflectable portion. In a first position, the deflectable portion prevents the penetrating member from exiting the cartridge. The deflectable portion is movable to a second position by creating an opening that allows the lancet to extend outward from the cartridge.

In another embodiment of the present invention, a device for use in penetrating tissue to obtain a body fluid sample includes a cartridge that has a plurality of cavities. A plurality of penetrating member are slidably coupled to the cartridge. Each of the penetrating members is at least partially housed in one of the cavities and is moveable relative to the other ones of the penetrating members along a path out of the cartridge and into tissue. A sterility barrier covers a plurality of openings on the cartridge and creates a sterile environment in the plurality of cavities.

In another embodiment of the present invention, a device includes a single radial cartridge. A plurality of bare lancets are slidably coupled to the cartridge and are selectively actuatable to penetrate tissue. Each of the lancets has a longitudinal axis. The lancets are longitudinally oriented in order to be substantially in a common plane.

In another embodiment of the present invention, a device includes a cartridge. A plurality of bare lancets are slidably coupled to the cartridge and are selectively actuatable to penetrate tissue. Each of the lancets has a longitudinal axis. A first sterility barrier is on a top surface of the cartridge. A second sterility barrier is on another surface of the cartridge.

In another embodiment of the present invention, an apparatus for penetrating an organism includes a penetrating member. A first surface is in physical contact with the penetrating member. A second surface is in physical contact with the penetrating member. The friction coefficient between the penetrating member and the second surface is at least 15% less than the friction coefficient between the penetrating member and the first surface.

In another embodiment of the present invention, a lancing device includes a penetrating member that has a shaft with a transverse slot configured to mate to a protuberance of a drive member.

In another embodiment of the present invention, a penetrating member includes a shaft that has a friction enhanced outer surface.

In another embodiment of the present invention, a device includes a cartridge that defines a plurality of cavities. A plurality of penetrating members are at least partially contained in the cavities of the single cartridge. The penetrating members are slidably movable to extend outward from the cartridge to penetrate tissue. The cavities each have a longitudinal opening that provides access to an elongate portion of the penetrating member. A sterility barrier is coupled to the cartridge. The sterility barrier covers a plurality of the longitudinal openings.

In another embodiment of the present invention, a device includes a cartridge that defines a plurality of cavities. A plurality of penetrating members are at least partially contained in the cavities of the single cartridge. The penetrating members are slidably movable to extend outward from lateral openings on the cartridge to penetrate tissue. A sterility barrier is coupled to the cartridge. The sterility barrier covers a plurality of the lateral openings.

In another embodiment of the present invention, a lancing system includes a cartridge. A plurality of penetrating members are coupled to the cartridge and are selectively actuatable to penetrate tissue. The penetrating members extend radially outward to penetrate tissue. An electrically powered drive force generator is operatively coupled to an active penetrating member to drive the penetrating member into a tissue site.

In another embodiment of the present invention, a lancing system includes a cartridge that has an opening which extends through a center of the cartridge. A plurality of penetrating members are coupled to the cartridge and are selectively actuatable to penetrate tissue. The penetrating members extend radially outward to penetrate tissue. A penetrating member driver is at least partially positioned within the central opening. The driver is operatively couplable to an active penetrating member to drive the penetrating member into a tissue site.

In another embodiment of the present invention, a lancing system includes a single cartridge. A plurality of penetrating members are coupled to the single cartridge and are selectively actuatable to penetrate tissue. A drive force generator is operatively coupled to an active penetrating member to drive the penetrating member into a tissue site. A feedback loop controls the position of the active penetrating member coupled to the drive force generator.

In another embodiment of the present invention, a lancing system includes a single cartridge. A plurality of penetrating members are coupled to the single cartridge and are selectively actuatable to penetrate tissue. A drive force generator is operatively coupled to an active penetrating member to drive the penetrating member into a tissue site. The drive force generator actuates at least one of the penetrating members to follow a velocity profile.

In another embodiment of the present invention, a device includes a single cartridge. A plurality of penetrating members are coupled to the single cartridge and are couplable to a penetrating member driver. A plurality of ratchet surfaces are on the cartridge for advancing the cartridge.

In another embodiment of the present invention, a device includes a single cartridge. At least 50 penetrating members are coupled to and at least partially housed in the single cartridge. The cartridge has a diameter that is no greater than about 5 inches. The penetrating members are movable in an outward direction from the cartridge to penetrate tissue when actuated by the penetrating member driver.

In another embodiment of the present invention, a device includes a single cartridge. At least 100 penetrating members are coupled to and at least partially housed in the single cartridge. The cartridge has a diameter that is no greater than 6 inches. The penetrating members are movable in an outward direction from the cartridge to penetrate tissue when actuated by the penetrating member driver.

In another embodiment of the present invention, a lancing system includes a plurality of cartridges. Each cartridge includes a plurality of penetrating members coupled to the cartridge and couplable to a penetrating member driver. A cartridge loading device moves at least one of the cartridges to be operatively coupled to the penetrating member driver.

In another embodiment of the present invention, a lancing device includes a penetrating member cartridge. Penetrating members are retractable and held within the cartridge so that they can not be used again.

In another embodiment of the present invention, a lancing device includes a cartridge. A foil or seal is provided and broken by a mechanism other than a penetrating member.

In another embodiment of the present invention, a lancing system for use with a plurality of penetrating members includes a penetrating member driver. A cartridge houses the plurality of penetrating members. A penetrating member release device releases one of the penetrating members from a sterile environment prior to use. A penetrating member coupling device is provided. The cartridge is positionable for one of the penetrating members to engage the coupler and be operatively coupled to the penetrating member driver.

In another embodiment of the present invention, a manufacturing method provides a cartridge that has a plurality of cavities for holding penetrating members. A plurality of cavities are sealed with a seal layer. A plurality of analyte sensors are provided by coupling a sensor layer to the cartridge.

In another embodiment of the present invention, a manufacturing method provides a cartridge that has a plurality of cavities for holding penetrating members. The cartridge is sterilized while each of the cavities is in a sealed condition. The cartridge contains at least one penetrating member. A sterility barrier is applied to the cartridge. The barrier covers a plurality of cavities.

In another embodiment of the present invention, a method transports a plurality of penetrating members, each in a sterilized environment, towards a penetrating member launch position. One of the penetrating members is released from a sterilized environment prior to actuation. The penetrating member is moved to the launch position to be operatively coupled to the penetrating member driver.

In another embodiment of the present invention, a method provides a penetrating member driver. A visual display is installed on the penetrating member driver. The display is coupled to a processor and relays penetrating member information selected from lancing performance or lancing setting.

In another embodiment of the present invention, a method provides a cartridge that has a plurality of penetrating members. A sterility barrier is penetrated. The barrier is moved clear of a path of an active one of the penetrating members. A frictional coupling is formed with the active one of the penetrating members. The active one of the penetrating members is actuated.

In another embodiment of the present invention, a method provides a cartridge that has a plurality of bare lancets. A frictional coupling is formed with the active one of the bare lancets. The active one of the penetrating members is actuated.

A further understanding of the nature and advantages of the invention will become apparent by reference to the remaining portions of the specification and drawings.

BRIEF DESCRIPTION OF THE DRAWINGS

FIG. 12 is a cross-sectional view of an embodiment having features of the invention.

FIG. 13 is a cross-sectional view of an embodiment having features of the invention in operation.

FIG. 14 is a cross-sectional view illustrating a low-friction coating applied to one penetrating member contact surface.

FIG. 15 is a cross-sectional view illustrating a coating applied to one penetrating member contact surface which increases friction and improves the microscopic contact area between the penetrating member and the penetrating member contact surface.

DESCRIPTION OF THE SPECIFIC EMBODIMENTS

Figure 1:
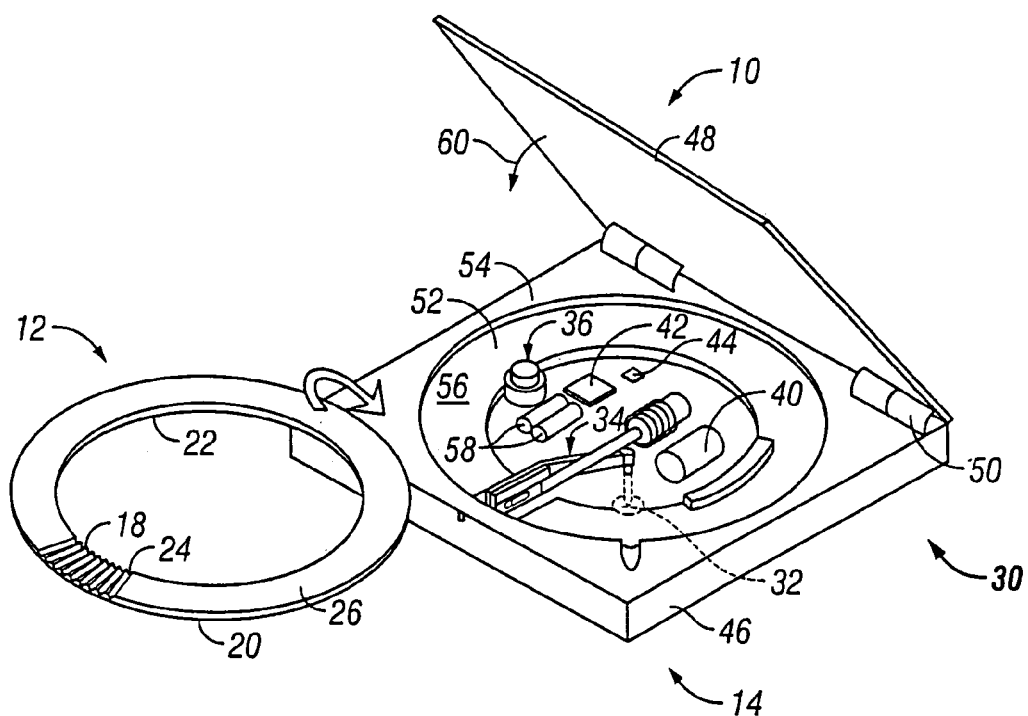
FIG. 1 is a perspective view illustrating a system, according to an embodiment for use in piercing skin to obtain a blood sample.

The present invention provides a multiple sensor solution for body fluid sampling. Specifically, some embodiments of the present invention provides a multiple sensor and multiple lancet solution to measuring analyte levels in the body. The invention may use a high density design. It may use lancets of smaller size than known lancets. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It must be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

"Analyte sensor" refers to any use, singly or in combination, of chemical test reagents and methods, electrical test circuits and methods, physical test components and methods, optical test components and methods, and biological test reagents and methods to yield information about a blood sample. Such methods are well known in the art and may be based on teachings of, e.g. Tietz Textbook of Clinical Chemistry, 3d Ed., Sec. V, pp. 776-78 (Burtis & Ashwood, Eds., W.B. Saunders Company, Philadelphia, 1999); U.S. Pat. No. 5,997,817 to Chrismore et al. (Dec. 7, 1999); U.S. Pat. No. 5,059,394 to Phillips et al. (Oct. 22, 1991); U.S. Pat. No. 5,001,054 to Wagner et al. (Mar. 19, 1991); and U.S. Pat. No. 4,392,933 to Nakamura et al. (Jul. 12, 1983), the teachings of which are hereby incorporated by reference, as well as others. Analyte sensor may include sensors in the sample test chamber that test electrochemical properties of the blood, or they may include optical means for sensing optical properties of the blood (e.g. oxygen saturation level), or they may include biochemical reagents (e.g. antibodies) to sense properties (e.g. presence of antigens) of the blood. Said analyte sensor may be present at, e.g., a "test site" or an "analytical site." The analyte sensor may comprise biosensing or reagent material that will react with an analyte in the blood (e.g. glucose) so that an appropriate signal correlating with the presence of the analyte is generated and can be read by the reader apparatus. Analyte sensor are "associated with" a chamber or other structure when the analyte sensor participates in the function of providing an appropriate signal about the blood sample to the reader device. Analyte sensor may also include nanowire sensors as described herein. Analyte sensor may use potentiometric, coulometric, or other method useful for detection of analyte levels.

FIGS. 1-11 of the accompanying drawings illustrates one embodiment of a system 10 for piercing skin to obtain a blood sample. The system 10 may include a replaceable cartridge 12 and an apparatus 14 for removably receiving the cartridge 12 and for manipulating components of the cartridge 12.

Figure 2:
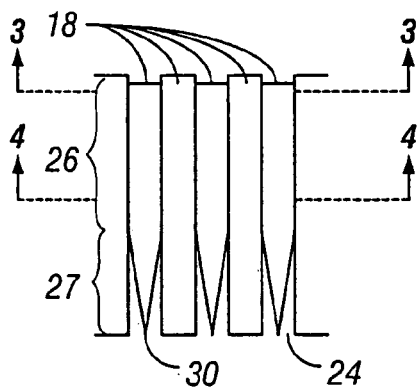
FIG. 2 is a plan view of a portion of a replaceable penetrating member cartridge forming part of the system.
Figure 3:
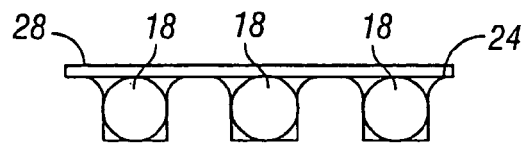
FIG. 3 is a cross-sectional end view on 3-3 in FIG. 2.
Figure 4:
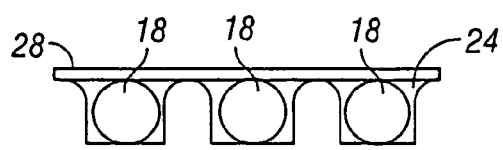
FIG. 4 is a cross-sectional end view on 4-4 in FIG. 2.

Referring jointly to FIGS. 1 and 2, the cartridge 12 may include a plurality of penetrating members 18. The cartridge 12 may be in the form of a circular disc and has an outer circular surface 20 and an opening forming an inner circular surface 22. A plurality of grooves 24 are formed in a planar surface 26 of the cartridge 12. Each groove 24 is elongated and extends radially out from a center point of the cartridge 12. Each groove 24 is formed through the outer circular surface 20. Although not shown, it should be understood that the grooves 24 are formed over the entire circumference of the planar surface 26. As shown in FIGS. 3 and 4, each groove 24 is relatively narrow closer to the center point of the cartridge 12 and slightly wider further from the center point. These grooves 24 may be molded into the cartridge 12, machined into the cartridge, or formed using other methods useful in the manufacture of medical devices.

In the present embodiment, each penetrating member 18 has an elongated body 26 and a sharpened distal end 27 having a sharp tip 30. The penetrating member 18 may have a circular in cross-section with a diameter in this embodiment of about 0.315 mm. All outer surfaces of the penetrating member 18 may have the same coefficient of friction. The penetrating member may be, but is not necessarily, a bare lancet. The lancet is "bare", in the sense that no raised formations or molded parts are formed thereon that are complementarily engageable with another structure. Traditional lancets include large plastic molded parts that are used to facilitate engagement. Unfortunately, such attachments add size and cost. In the most basic sense, a bare lancet or bare penetrating member is an elongate wire having sharpened end. If it is of sufficiently small diameter, the tip may be penetrating without having to be sharpened. A bare lancet may be bent and still be considered a bare lancet. The bare lancet in one embodiment may be made of one material.

In the present embodiment, each penetrating member 18 is located in a respective one of the grooves 24. The penetrating members 18 have their sharpened distal ends 27 pointed radially out from the center point of the cartridge 12. A proximal end of each penetrating member 15 may engage in an interference fit with opposing sides of a respective groove 24 as shown in FIG. 3. Other embodiments of the cartridge 12 may not use such an interference fit. For example, they may use a fracturable adhesive to releasably secure the penetrating member 18 to the cartridge 12. As shown in FIG. 4, more distal portions of the penetrating member 18 are not engaged with the opposing sides of the groove 24 due to the larger spacing between the sides.

The cartridge 12 may further include a sterilization barrier 28 attached to the upper surface 26. The sterilization barrier 28 is located over the penetrating members 18 and serves to insulate the penetrating members 18 from external contaminants. The sterilization barrier 28 is made of a material that can easily be broken when an edge of a device applies a force thereto. The sterilization barrier 28 alone or in combination with other barriers may be used to create a sterile environment about at least the tip of the penetrating member prior to lancing or actuation. The sterilization barrier 28 may be made of a variety of materials such as but not limited to metallic foil, aluminum foil, paper, polymeric material, or laminates combining any of the above. Other details of the sterilization barrier are detailed herein.

In the present embodiment, the apparatus 14 may include a housing 30, an initiator button 32, a penetrating member movement subassembly 34, a cartridge advance subassembly 36, batteries 38, a capacitor 40, a microprocessor controller 42, and switches 44. The housing 30 may have a lower portion 46 and a lid 48. The lid 48 is secured to the lower portion 46 with a hinge 50. The lower portion 46 may have a recess 52. A circular opening 54 in the lower portion 46 defines an outer boundary of the recess 52 and a level platform 56 of the lower portion 46 defines a base of the recess 52.

In use, the lid 48 of the present embodiment is pivoted into a position as shown in FIG. 1. The cartridge 12 is flipped over and positioned in the recess 52. The planar surface 26 rests against the level platform 56 and the circular opening 54 contacts the outer circular surface 20 to prevent movement of the cartridge 12 in a plane thereof. The lid 48 is then pivoted in a direction 60 and closes the cartridge 12.

Figure 5:
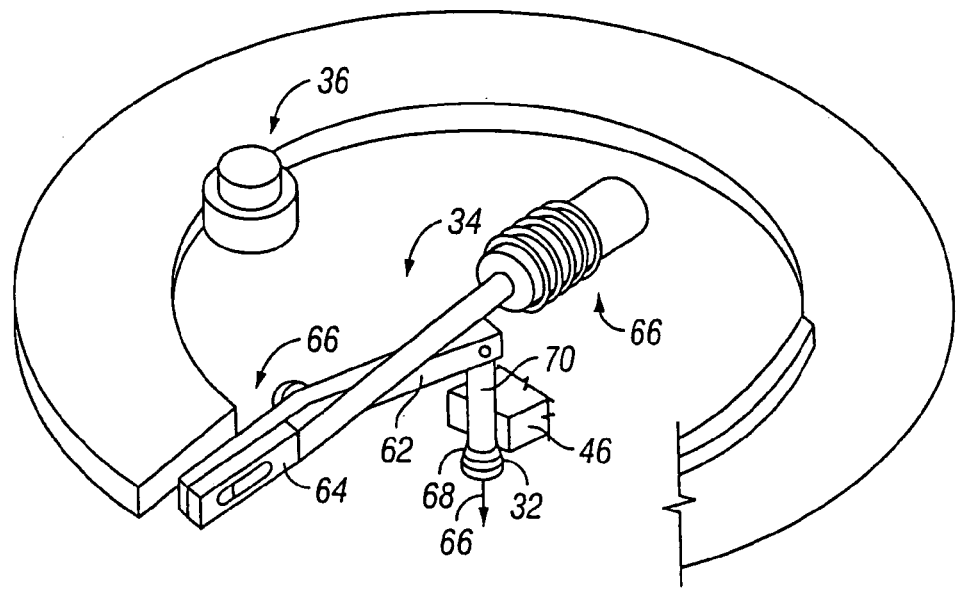
FIG. 5 is a perspective view of an apparatus forming part of the system and used for manipulating components of the cartridge, illustrating pivoting of a penetrating member accelerator in a downward direction.

Referring to the embodiment shown in FIG. 5, the penetrating member movement subassembly 34 includes a lever 62, a penetrating member accelerator 64, a linear actuator 66, and a spring 68. Other suitable actuators including but not limited to rotary actuators are described in commonly assigned, copending U.S. patent application Ser. No. 10/127,395 filed Apr. 19, 2002. The lever 62 may be pivotably secured to the lower portion 46. The button 32 is located in an accessible position external of the lower portion 46 and is connected by a shaft 70 through the lower portion 46 to one end of the lever 62. The penetrating member accelerator 64 is mounted to an opposing end of the lever 62. A user depresses the button 32 in an upward direction 66 so that the shaft 70 pivots the end of the lever 62 to which it is connected in an upward direction. The opposing end of the lever pivots in a downward direction 66. The spring 46 is positioned between the button 32 and the base 40 and compresses when the button 32 is depressed to create a force that tends to move the button 32 down and pivot the penetrating member accelerator upward in a direction opposite to the direction 64.

Figure 6A:
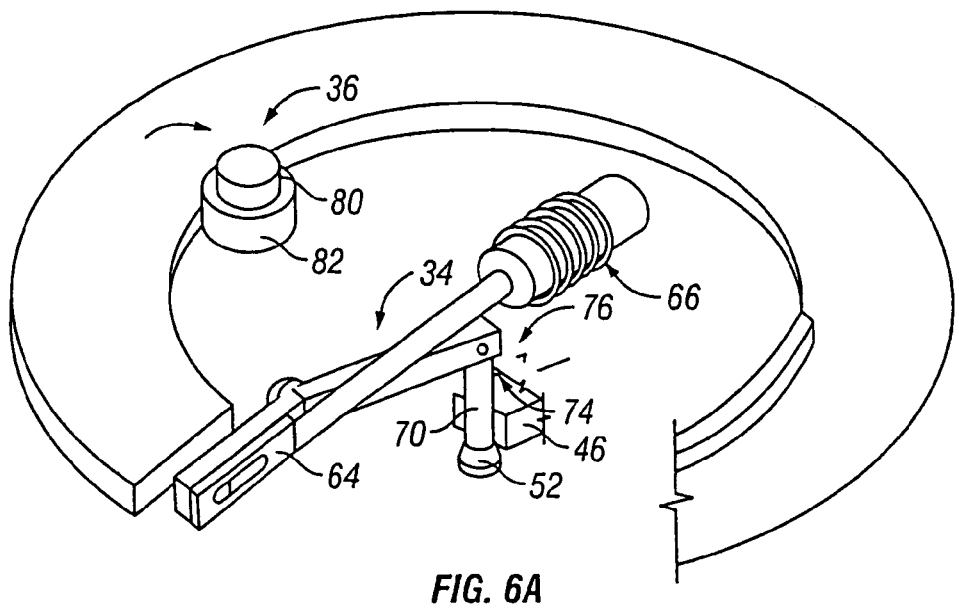
FIG. 6A is a view similar to FIG. 5, illustrating how the cartridge is rotated or advanced.
Figure 6B:
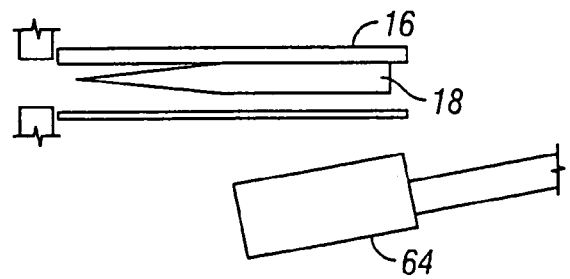
FIG. 6B is a cross-sectional side view illustrating how the penetrating member accelerator allows for the cartridge to be advanced.

Referring to FIGS. 6A and 6B in this particular embodiment, the movement of the button into the position shown in FIG. 5 also causes contact between a terminal 74 on the shaft 20 with a terminal 70 secured to the lower portion 46. Contact between the terminals 74 and 76 indicates that the button 32 has been fully depressed. With the button 32 depressed, the cartridge 12 can be rotated without interference by the penetrating member actuator 64. To this effect, the cartridge advancer subsystem 36 includes a pinion gear 80 and a stepper motor 82. The stepper motor 82 is secured to the lower portion 46. The pinion gear 80 is secured to the stepper motor 82 and is rotated by the stepper motor 82. Teeth on the pinion gear 80 engage with teeth on the inner circular surface 22 of the cartridge 12. Rotation of the pinion gear 80 causes rotation of the cartridge 12 about the center point thereof. Each time that the terminals 74 and 76 make contact, the stepper motor 82 is operated to rotate the cartridge 12 through a discrete angle equal to an angular spacing from a centerline of one of the penetrating members 18 to a centerline of an adjacent penetrating member. A select penetrating member 18 is so moved over the penetrating member accelerator 64, as shown in FIG. 6B. Subsequent depressions of the button 32 will cause rotation of subsequent adjacent penetrating members 18 into a position over the penetrating member accelerator 64.

Figure 7A:
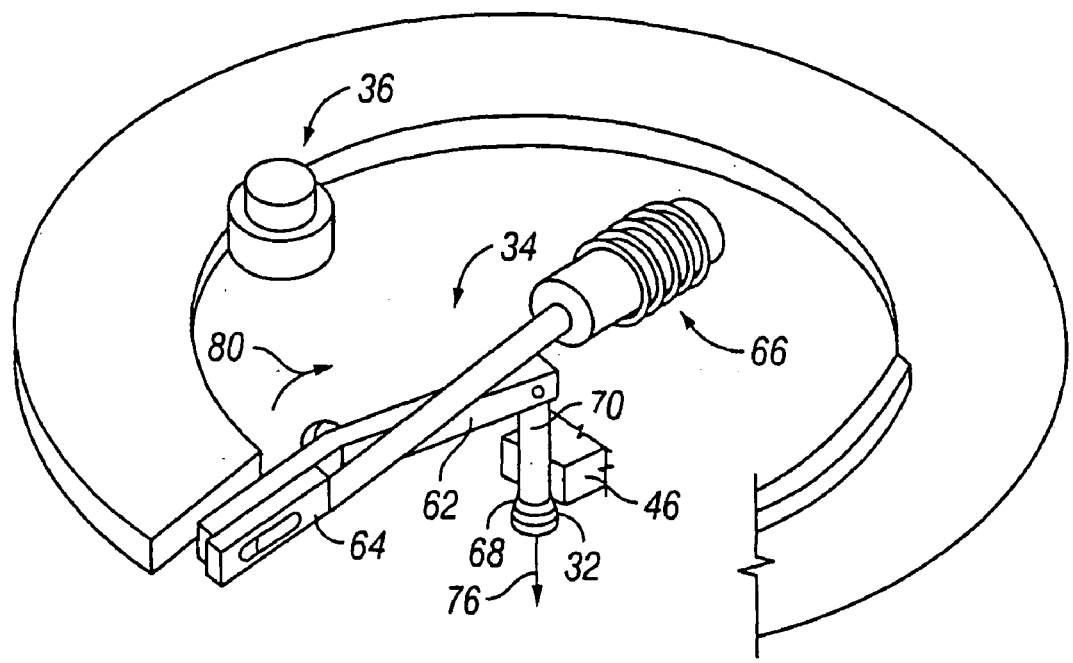
FIGS. 7A and 7B are views similar to FIGS. 6A and 6B, respectively, illustrating pivoting of the penetrating member accelerator in an opposite direction to engage with a select one of the penetrating members in the cartridge.
Figure 7B:
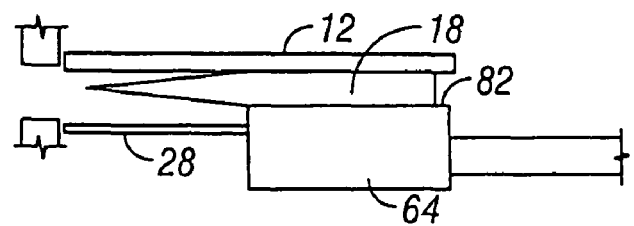

The user then releases pressure from the button, as shown in FIG. 7A. The force created by the spring 68 or other resilient member moves the button 32 in a downward direction 76. The shaft 70 is pivotably secured to the lever 62 so that the shaft 70 moves the end of the lever 62 to which it is connected down. The opposite end of the lever 62 pivots the penetrating member accelerator 64 upward in a direction 80. As shown in FIG. 7B, an edge 82 of the penetrating member accelerator 64 breaks through a portion of the sterilization barrier 28 and comes in to physical contact with a lower side surface of the penetrating member 18.

Figure 8A:
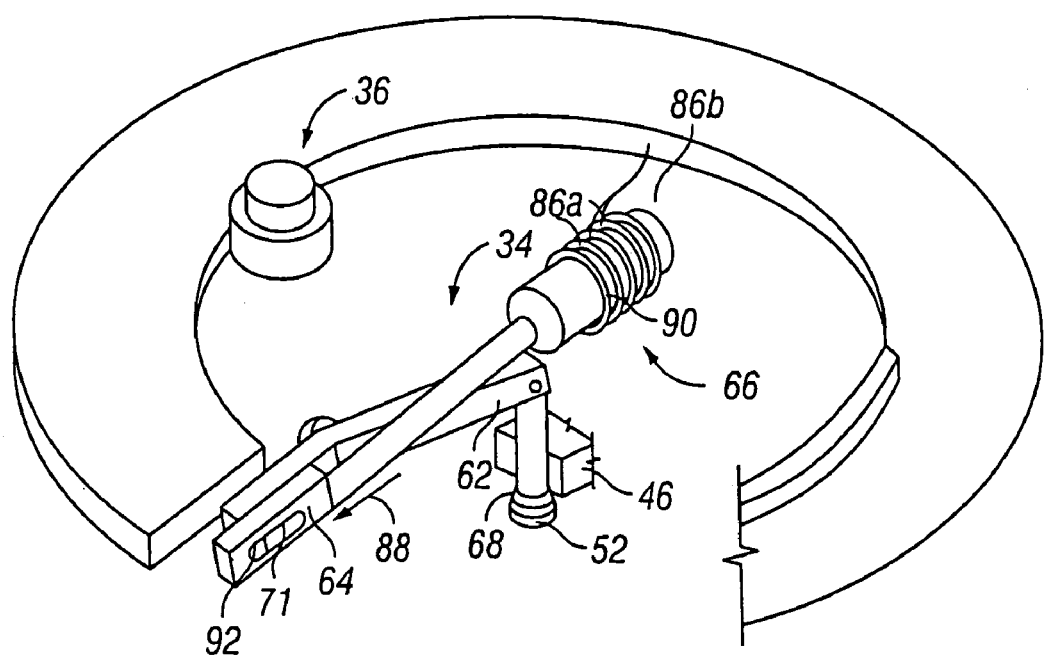
FIGS. 8A and 8B are views similar to FIGS. 7A and 7B, respectively, illustrating how the penetrating member accelerator moves the selected penetrating member to pierce skin.
Figure 8B:
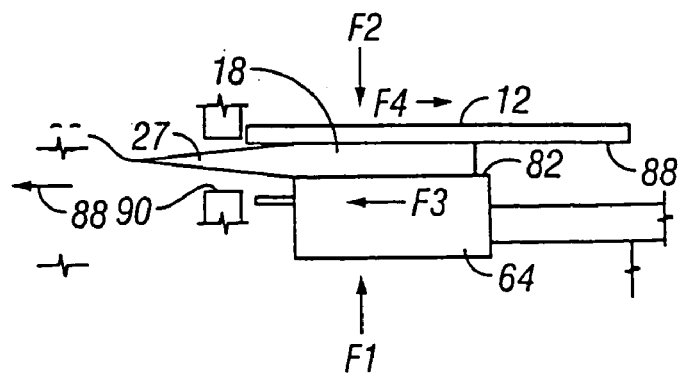

Referring to FIG. 8A, the linear actuator 66 includes separate advancing coils 86A and retracting coils 86B, and a magnetizable slug 90 within the coils 86A and 86B. The coils 86A and 86B are secured to the lower portion of 46, and the slug 90 can move within the coils 86A and 88B. Once the penetrating member accelerator 64 is located in the position shown in FIGS. 7A and 7B, electric current is provided to the advancing coils 86 only. The current in the advancing coils 86 creates a force in a direction 88 on the slug 90 according to conventional principles relating to electromagnetics.

A bearing 91 is secured to the lever and the penetrating member accelerator 64 has a slot 92 over the bearing 91. The slot 92 allows for the movement of the penetrating member accelerator 64 in the direction 88 relative to the lever 62, so that the force created on the slug moves the penetrating member accelerator 64 in the direction 88.

The spring 68 is not entirely relaxed, so that the spring 68, through the lever 62, biases the penetrating member accelerator 64 against the lower side surface of the penetrating member 18 with a force F1. The penetrating member 18 rests against a base 88 of the cartridge 12. An equal and opposing force F2 is created by the base 88 on an upper side surface of the penetrating member 18.

The edge 82 of the penetrating member accelerator 64 has a much higher coefficient of friction than the base 88 of the cartridge 12. The higher coefficient of friction of the edge contributes to a relatively high friction force F3 on the lower side surface of the penetrating member 18. The relatively low coefficient of friction of the base 88 creates a relatively small friction force F4 on the upper side surface of the penetrating member 18. A difference between the force F3 and F4 is a resultant force that accelerates the penetrating member in the direction 88 relative to the cartridge 12. The penetrating member is moved out of the interference fit illustrated in FIG. 3. The bare penetrating member 18 is moved without the need for any engagement formations on the penetrating member. Current devices, in contrast, often make use a plastic body molded onto each penetrating member to aid in manipulating the penetrating members. Movement of the penetrating member 18 moves the sharpened end thereof through an opening 90 in a side of the lower portion 46. The sharp end 30 of the penetrating member 18 is thereby moved from a retracted and safe position within the lower portion 46 into a position wherein it extends out of the opening 90. Accelerated, high-speed movement of the penetrating member is used so that the sharp tip 30 penetrates skin of a person. A blood sample can then be taken from the person, typically for diabetic analysis.

Figure 9A:
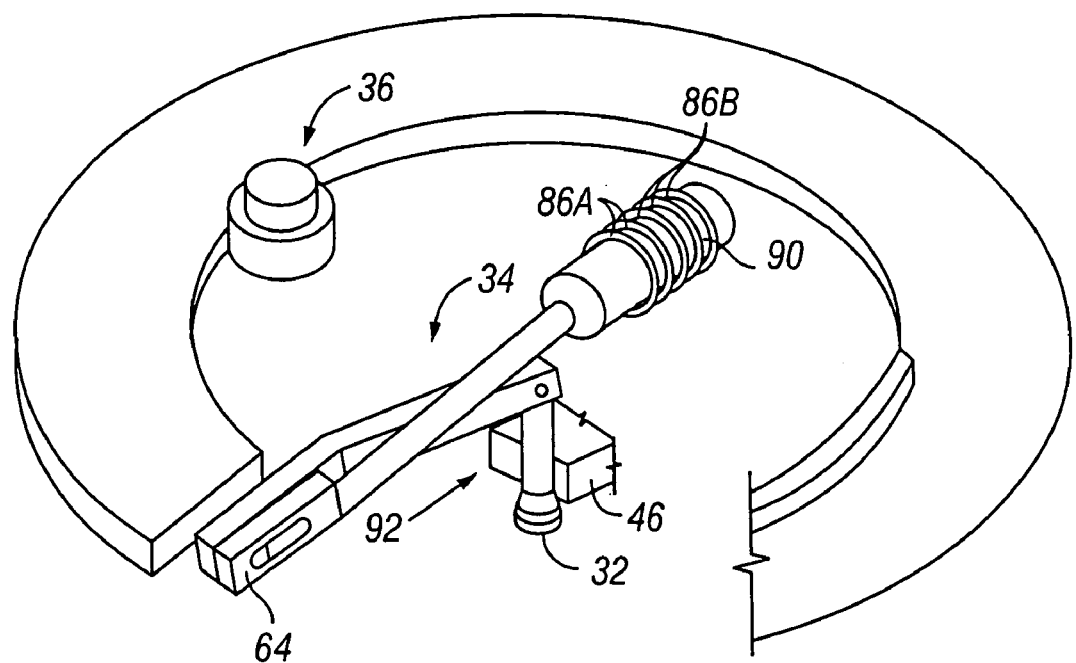
FIGS. 9A and 9B are views similar to FIGS. 8A and 8B, respectively, illustrating how the penetrating member accelerator returns the penetrating member to its original position.
Figure 9B:
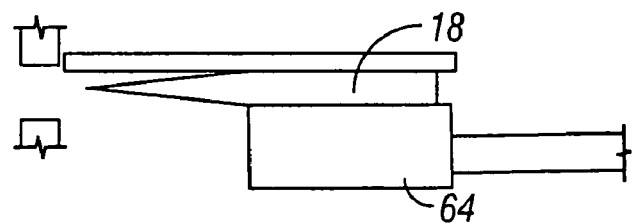

Reference is now made to FIGS. 9A and 9B. After the penetrating member is accelerated (for example, but not limitation, less than 0.25 seconds thereafter), the current to the accelerating coils 86A is turned off and the current is provided to the retracting coils 86B. The slug 90 moves in an opposite direction 92 together with the penetrating member accelerator 64. The penetrating member accelerator 64 then returns the used penetrating member into its original position, i.e., the same as shown in FIG. 7B.

Subsequent depression of the button as shown in FIG. 5 will then cause one repetition of the process described, but with an adjacent sterile penetrating member. Subsequent sterile penetrating members can so be used until all the penetrating members have been used, i.e., after one complete revolution of the cartridge 12. In this embodiment, a second revolution of the cartridge 12 is disallowed to prevent the use of penetrating members that have been used in a previous revolution and have become contaminated. The only way in which the user can continue to use the apparatus 14 is by opening the lid 48 as shown in FIG. 1, removing the used cartridge 12, and replacing the used cartridge with another cartridge. A sensor (not shown) detects whenever a cartridge is removed and replaced with another cartridge. Such a sensor may be but is not limited to an optical sensor, an electrical contact sensor, a bar code reader, or the like.

Figure 10:
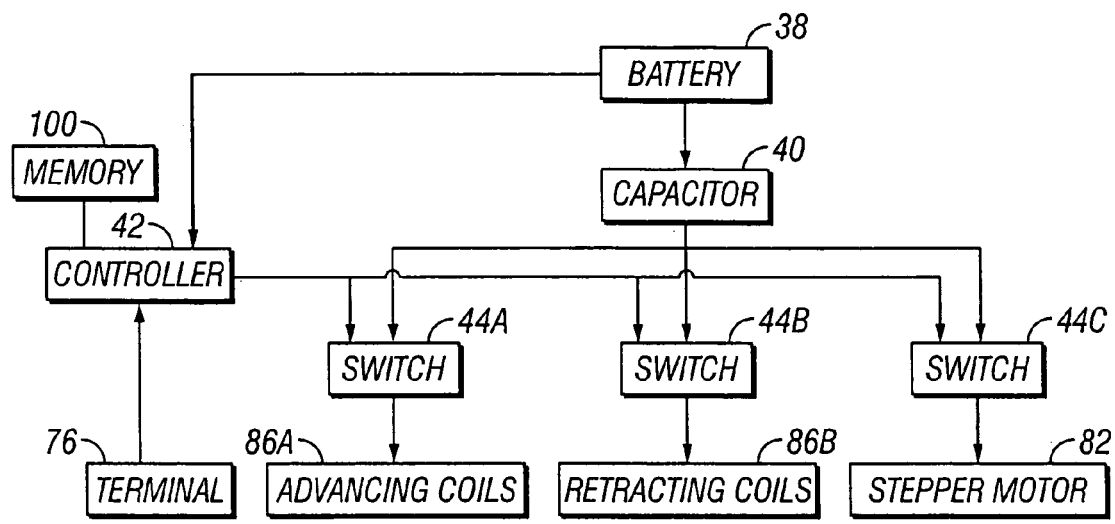
FIG. 10 is a block diagram illustrating functional components of the apparatus.

FIG. 10 illustrates the manner in which the electrical components may be functionally interconnected for the present embodiment. The battery 38 provides power to the capacitor 40 and the controller 42. The terminal 76 is connected to the controller 42 so that the controller recognizes when the button 32 is depressed. The capacitor to provide power (electric potential and current) individually through the switches (such as field-effect transistors) to the advancing coils 86A, retracting coils 86B and the stepper motor 82. The switches 44A, B, and C are all under the control of the controller 42. A memory 100 is connected to the controller. A set of instructions is stored in the memory 100 and is readable by the controller 42. Further functioning of the controller 42 in combination with the terminal 76 and the switches 44A, B, and C should be evident from the foregoing description.

Figure 11:
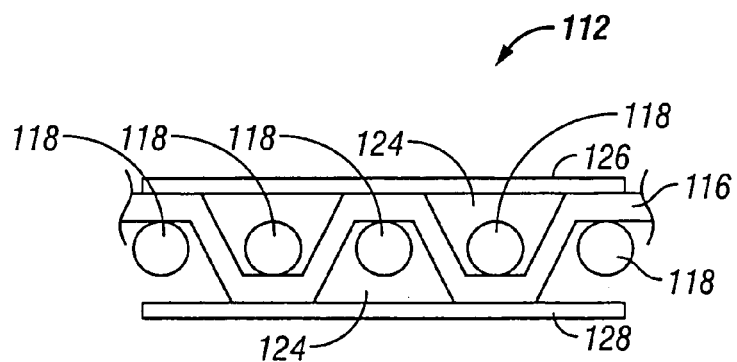
FIG. 11 is an end view illustrating a cartridge according to an optional embodiment that allows for better adhesion of sterilization barriers.

FIG. 11 illustrates a configuration for another embodiment of a cartridge having penetrating members. The cartridge 112 has a corrugated configuration and a plurality of penetrating members 118 in grooves 124 formed in opposing sides of the cartridge 112. Sterilization barriers 126 and 128 are attached over the penetrating members 118 at the top and the penetrating members 118 at the bottom, respectively. Such an arrangement provides large surfaces for attachment of the sterilization barriers 126 and 128. All the penetrating members 18 on the one side are used first, whereafter the cartridge 112 is turned over and the penetrating members 118 on the other side are used. Additional aspects of such a cartridge are also discussed in FIGS. 42-44.

Referring now to FIGS. 12-13, a friction based method of coupling with and driving bare lancets or bare penetrating members will be described in further detail. Any embodiment of the present invention disclosed herein may be adapted to use these methods. As seen in FIG. 12, surface 201 is physically in contact with penetrating member 202. Surface 203 is also physically in contact with penetrating member 202. In the present embodiment of the invention, surface 201 is stainless steel, penetrating member 202 is stainless steel, and surface 203 is polytetrafluoroethylene-coated stainless steel.

FIG. 13 illustrates one embodiment of the friction based coupling in use. Normal force 206 may be applied vertically to surface 201, pressing it against penetrating member 202. Penetrating member 202 is thereby pressed against surface 203. Normal force 206 is transmitted through surface 201 and penetrating member 202 to also act between penetrating member 202 and surface 203. Surface 203 is held rigid or stationary with respect to a target of the lancet. Using the classical static friction model, the maximum frictional force between surface 201 and penetrating member 202 is equal to the friction coefficient between surface 201 and penetrating member 202 multiplied by the normal force between surface 201 and penetrating member 202. In this embodiment, the maximum frictional force between surface 203 and penetrating member 202 is equal to the coefficient of friction between the surface 203 and the penetrating member 202 multiplied by the normal force between the surface 203 and the penetrating member 202. Because friction coefficient between surface 203 and penetrating member 202 is less than friction coefficient between surface 201 and penetrating member 202, the interface between surface 201 and penetrating member 202 can develop a higher maximum static friction force than can the interface between surface 203 and penetrating member 202.

Driving force as indicated by arrow 207 is applied to surface 201 perpendicular to normal force 206. The sum of the forces acting horizontally on surface 201 is the sum of driving force 207 and the friction force developed at the interface of surface 201 and penetrating member 202, which acts in opposition to driving force 207. Since the coefficient of friction between surface 203 and penetrating member 202 is less than the coefficient of friction between surface 201 and penetrating member 202, penetrating member 202 and surface 201 will remain stationary with respect to each other and can be considered to behave as one piece when driving force 207 just exceeds the maximum frictional force that can be supported by the interface between surface 203 and penetrating member 202. Surface 201 and penetrating member 202 can be considered one piece because the coefficient of friction between surface 201 and penetrating member 202 is high enough to prevent relative motion between the two.

In one embodiment, the coefficient of friction between surface 201 and penetrating member 202 is approximately 0.8 corresponding to the coefficient of friction between two surfaces of stainless steel, while the coefficient of friction between surface 203 and penetrating member 202 is approximately 0.04, corresponding to the coefficient of friction between a surface of stainless steel and one of polytetrafluoroethylene. Normal force 206 has a value of 202 Newtons. Using these values, the maximum frictional force that the interface between surface 201 and penetrating member 202 can support is 1.6 Newtons, while the maximum frictional force that the interface between surface 203 and penetrating member 202 can support is 0.08 Newtons. If driving force 207 exceeds 0.08 Newtons, surface 201 and penetrating member 202 will begin to accelerate together with respect to surface 203. Likewise, if driving force 207 exceeds 1.6 Newtons and penetrating member 202 encounters a rigid barrier, surface 201 would move relative to penetrating member 202.

Another condition, for example, for surface 201 to move relative to penetrating member 202 would be in the case of extreme acceleration. In an embodiment, penetrating member 202 has a mass of $8.24 \times 10^{-6}$ kg. An acceleration of 194,174 m/s2 of penetrating member 202 would therefore be required to exceed the frictional force between penetrating member 202 and surface 201, corresponding to approximately 19,800 g's. Without being bound to any particular embodiment or theory of operation, other methods of applying friction base coupling may also be used. For example, the penetrating member 202 may be engaged by a coupler using a interference fit to create the frictional engagement with the member.

FIG. 14 illustrates a polytetrafluoroethylene coating on stainless steel surface 203 in detail. It should be understood that the surface 203 may be coated with other materials such as but not limited to Telfon®, silicon, polymer or glass. The coating may cover all of the penetrating member, only the proximal portions, only the distal portions, only the tip, only some other portion, or some combination of some or all of the above. FIG. 15 illustrates a doping of lead applied to surface 201, which conforms to penetrating member 202 microscopically when pressed against it. Both of these embodiments and other coated embodiments of a penetrating member may be used with the actuation methods described herein.

The shapes and configurations of surface 201 and surface 102 could be some form other than shown in FIGS. 12-15. For example, surface 201 could be the surface of a wheel, which when rotated causes penetrating member 202 to advance or retract relative to surface 203. Surface 201 could be coated with another conformable material besides lead, such as a plastic. It could also be coated with particles, such as diamond dust, or given a surface texture to enhance the friction coefficient of surface 201 with penetrating member 202. Surface 202 could be made of or coated with diamond, fluorinated ethylene propylene, perfluoroalkoxy, a copolymer of ethylene and tetrafluoroethylene, a copolymer of ethylene and chlorotrifluoroethylene, or any other material with a coefficient of friction with penetrating member 202 lower than that of the material used for surface 201.

Figure 16:
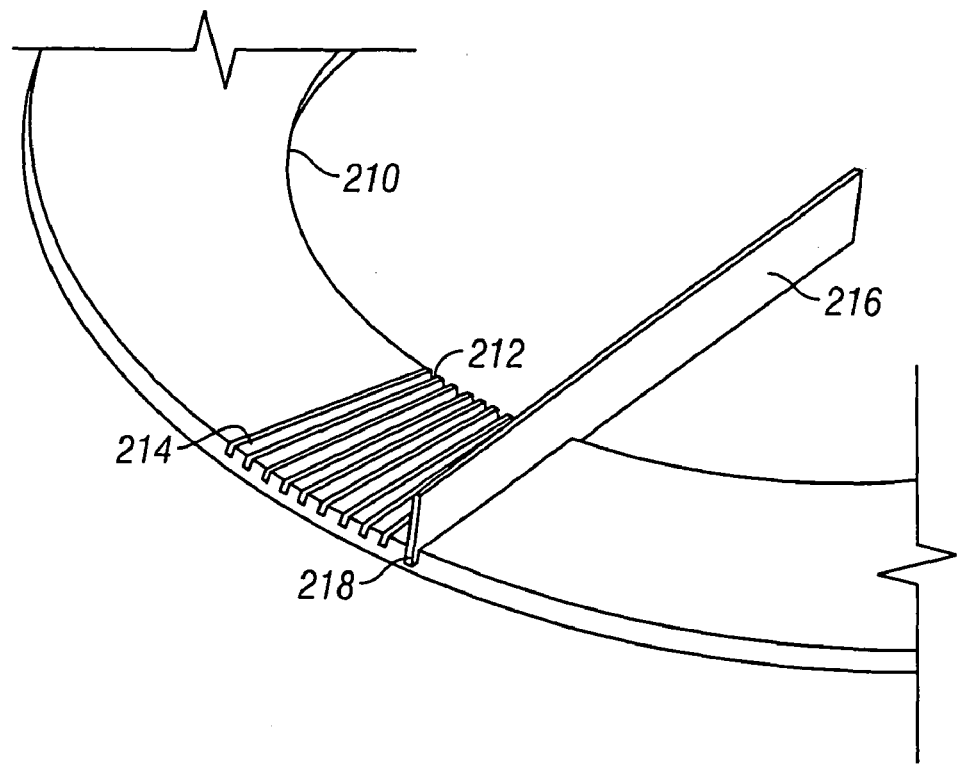
FIG. 16 illustrates a portion of a penetrating member cartridge having an annular configuration with a plurality of radially oriented penetrating member slots and a distal edge of a drive member disposed in one of the penetrating member slots.

Referring to FIG. 16, a portion of a base plate 210 of an embodiment of a penetrating member cartridge is shown with a plurality of penetrating member slots 212 disposed in a radial direction cut into a top surface 214 of the base plate. A drive member 216 is shown with a distal edge 218 disposed within one of the penetrating member slots 212 of the base plate 210. The distal edge 218 of the drive member 216 is configured to slide within the penetrating member slots 212 with a minimum of friction but with a close fit to minimize lateral movement during a lancing cycle.

Figure 17:
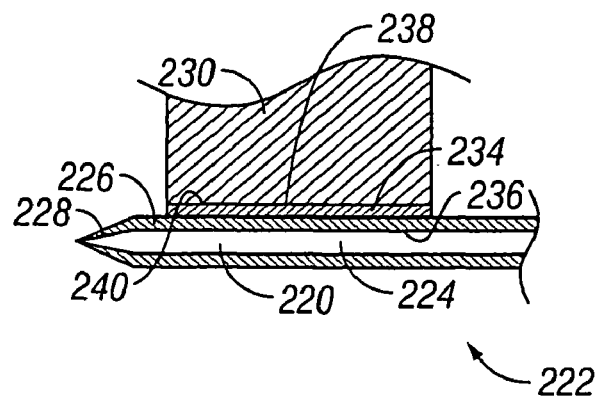
FIG. 17 is an elevational view in partial longitudinal section of a coated penetrating member in contact with a coated penetrating member contact surface.

FIG. 17 shows a distal portion 220 of a coated penetrating member 222 in partial longitudinal section. The coated penetrating member 222 has a core portion 224, a coating 226 and a tapered distal end portion 228. A portion of a coated drive member 230 is shown having a coating 234 with penetrating member contact surface 236. The penetrating member contact surface 236 forms an interface 238 with an outer surface 240 of the coated penetrating member 222. The interface 238 has a characteristic friction coefficient that will depend in part on the choice of materials for the penetrating member coating 226 and the drive member coating 234. If silver is used as the penetrating member and drive member coating 226 and 236, this yields a friction coefficient of about 1.3 to about 1.5. Other materials can be used for coatings 226 and 236 to achieve the desired friction coefficient. For example, gold, platinum, stainless steel and other materials may be used for coatings 226 and 236. It may be desirable to use combinations of different materials for coatings 226 and 236. For example, an embodiment may include silver for a penetrating member coating 226 and gold for a drive member coating. Some embodiments of the interface 238 can have friction coefficients of about 1.15 to about 5.0, specifically, about 1.3 to about 2.0.

Embodiments of the penetrating member 222 can have an outer transverse dimension or diameter of about 200 to about 400 microns, specifically, about 275 to about 325 microns. Embodiments of penetrating member 222 can have a length of about 10 to about 30 millimeters, specifically, about 15 to about 25 millimeters. Penetrating member 222 can be made from any suitable high strength alloy such as stainless steel or the like.

Figure 18:
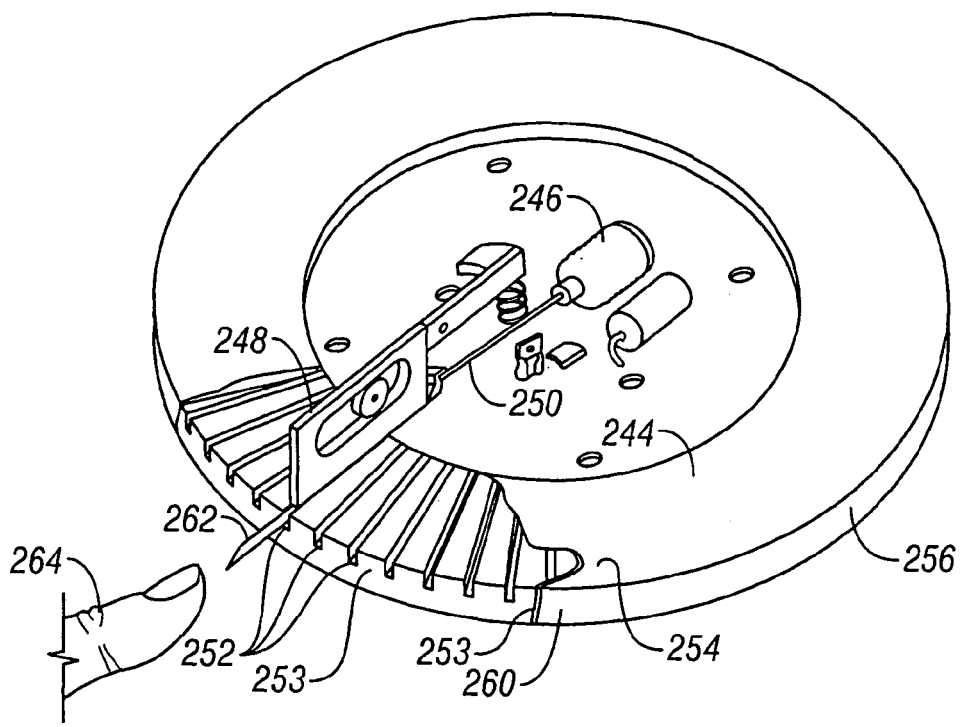
FIG. 18 illustrates an embodiment of a lancing device having features of the invention.

FIG. 18 is a perspective view of a lancing device 242 having features of the invention. A penetrating member cartridge 244 is disposed about a driver 246 that is coupled to a drive member 248 by a coupler rod 250. The penetrating member cartridge 244 has a plurality of penetrating member slots 252 disposed in a radial configuration in a top surface 254 a base plate 256 of the penetrating member cartridge 244. The distal ends 253 of the penetrating member slots 252 are disposed at an outer surface 260 of the base plate 256. A fracturable sterility barrier 258, shown partially cut away, is disposed on the top surface 254 of base plate 256 over the plurality of penetrating member slots 252. The sterility barrier 258 is also disposed over the outer surface 260 of the base plate 256 in order to seal the penetrating member slots from contamination prior to a lancing cycle. A distal portion of a penetrating member 262 is shown extending radially from the penetrating member cartridge 244 in the direction of a patient's finger 264.

Figure 19:
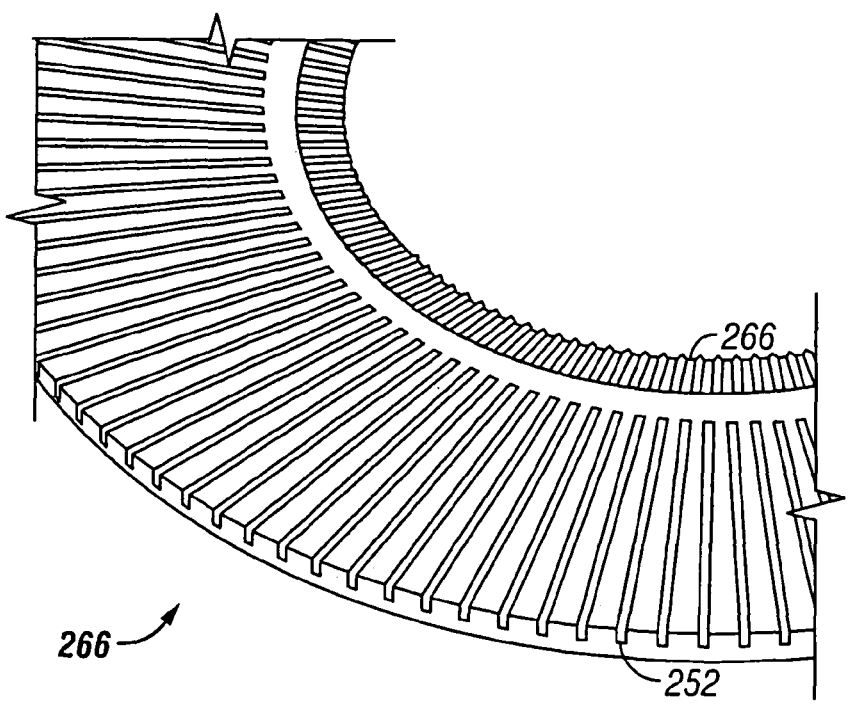
FIG. 19 is a perspective view of a portion of a penetrating member cartridge base plate having a plurality of penetrating member slots and drive member guide slots disposed radially inward of and aligned with the penetrating member slots.

FIG. 19 illustrates a portion of the base plate 256 used with the lancing device 242 in more detail and without sterility barrier 258 in place (for ease of illustration). The base plate 256 includes a plurality of penetrating member slots 252 which are in radial alignment with corresponding drive member slots 266. The drive member slots 266 have an optional tapered input configuration that may facilitate alignment of the drive member 248 during downward movement into the drive member slot 266 and penetrating member slot 252. Penetrating member slots 252 are sized and configured to accept a penetrating member 262 disposed therein and allow axial movement of the penetrating member 262 within the penetrating member slots 252 without substantial lateral movement.

Referring again to FIG. 18, in use, the present embodiment of penetrating member cartridge 242 is placed in an operational configuration with the driver 246. A lancing cycle is initiated and the drive member 248 is brought down through the sterility barrier 258 and into a penetrating member slot 252. A penetrating member contact surface of the drive member then makes contact with an outside surface of the penetrating member 262 and is driven distally toward the patient's finger 264 as described above with regard to the embodiment discussed in FIG. 20. The friction coefficient between the penetrating member contact surface of the drive member 248 and the penetrating member 262 is greater than the friction coefficient between the penetrating member 262 and an interior surface of the penetrating member slots 252. As such, the drive member 248 is able to drive the penetrating member 262 distally through the sterility barrier 258 and into the patient's finger 264 without any relative movement or substantial relative movement between the drive member 248 and the penetrating member 262.

Figure 20:
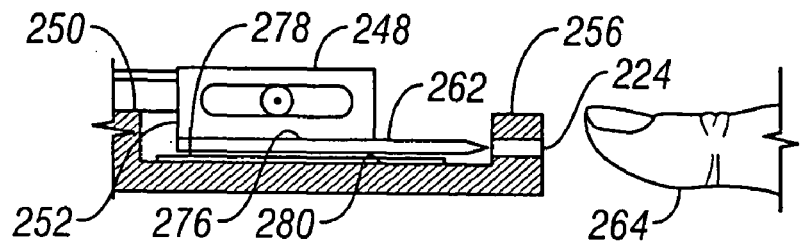
FIGS. 20-22 illustrate a penetrating member cartridge in section, a drive member, a penetrating member and the tip of a patient's finger during three sequential phases of a lancing cycle.
Figure 21:
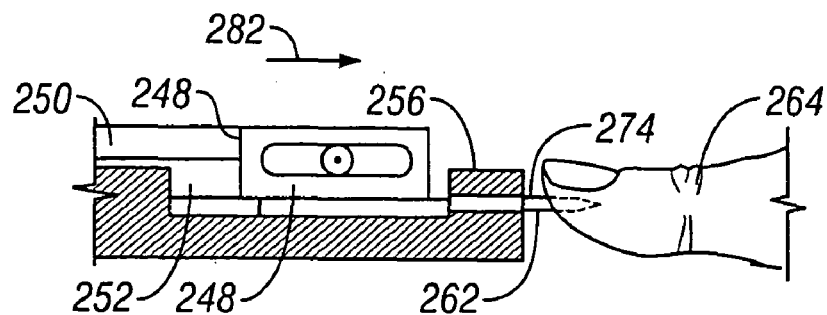
Figure 22:
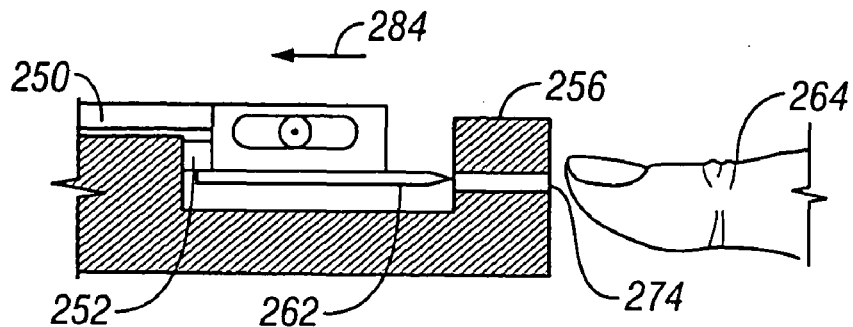
Figure 23:
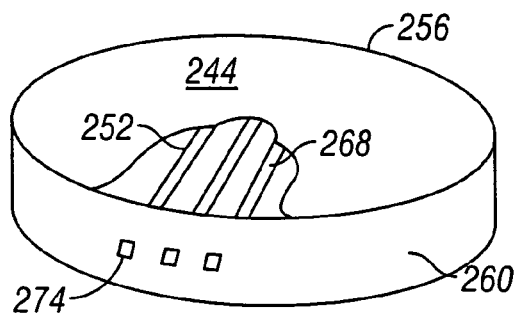
FIG. 23 illustrates an embodiment of a penetrating member cartridge having features of the invention.
Figure 24:
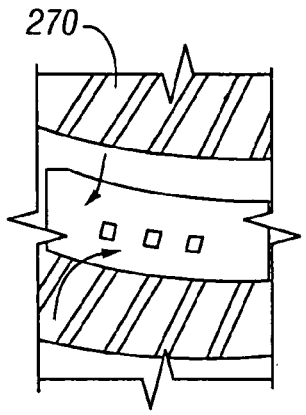
FIG. 24 is an exploded view of a portion of the penetrating member cartridge of FIG. 12.

Referring to FIGS. 20-22, a lancing cycle sequence is shown for a lancing device 242 with another embodiment of a penetrating member cartridge 244 as shown in FIGS. 23 and 24. The base plate 256 of the penetrating member cartridge 242 shown in FIGS. 23 and 24 has a plurality of penetrating member slots 252 with top openings 268 that do not extend radially to the outer surface 260 of the base plate 256. In this way, the penetrating member slots 252 can be sealed with a first sterility barrier 270 disposed on the top surface 254 of the base plate 256 and a second sterility barrier 272 disposed on the outer surface 260 of the base plate 256. Penetrating member outlet ports 274 are disposed at the distal ends of the penetrating member slots 252.

Referring again to FIG. 20, the penetrating member 262 is shown in the proximally retracted starting position within the penetrating member slot 252. The outer surface of the penetrating member 276 is in contact with the penetrating member contact surface 278 of the drive member 248. The friction coefficient between the penetrating member contact surface 278 of the drive member 248 and the outer surface 276 of the penetrating member 262 is greater than the friction coefficient between the penetrating member 262 and an interior surface 280 of the penetrating member slots 252. A distal drive force as indicated by arrow 282 in FIG. 10 is then applied via the drive coupler 250 to the drive member 248 and the penetrating member is driven out of the penetrating member outlet port 274 and into the patient's finger 264. A proximal retraction force, as indicated by arrow 284 in FIG. 22, is then applied to the drive member 248 and the penetrating member 262 is withdrawn from the patient's finger 264 and back into the penetrating member slot 252.

Figure 25:
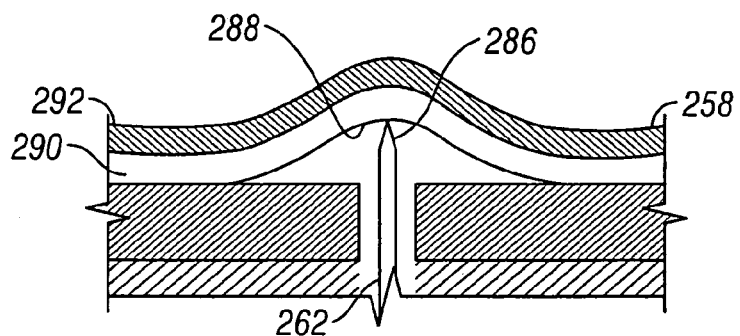
FIGS. 25 and 26 illustrate a multiple layer sterility barrier disposed over a penetrating member slot being penetrated by the distal end of a penetrating member during a lancing cycle.
Figure 26:
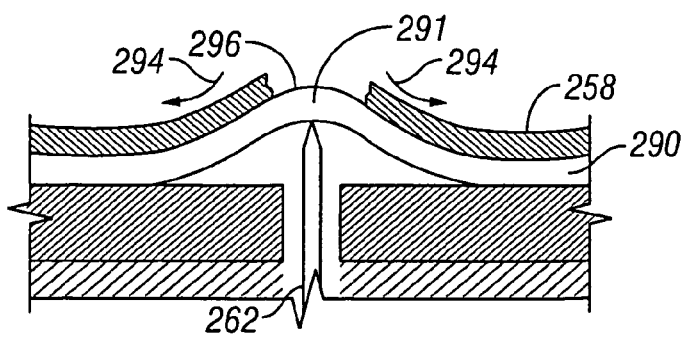

FIGS. 25 and 26 illustrate an embodiment of a multiple layer sterility barrier 258 in the process of being penetrated by a penetrating member 62. It should be understood that this barrier 258 may be adapted for use with any embodiment of the present invention. The sterility barrier 258 shown in FIGS. 25 and 26 is a two layer sterility barrier 258 that facilitates maintaining sterility of the penetrating member 262 as it passes through and exits the sterility barrier 258. In FIG. 25, the distal end 286 of the penetrating member 262 is applying an axial force in a distal direction against an inside surface 288 of a first layer 290 of the sterility barrier 258, so as to deform the first layer 290 of the sterility barrier 258. The deformation 291 of the first layer 290 in turn applies a distorting force to the second layer 292 of the sterility barrier 258. The second layer of the sterility barrier is configured to have a lower tensile strength that the first layer 290. As such, the second layer 292 fails prior to the first layer 290 due to the strain imposed on the first layer 290 by the distal end 286 of the penetrating member 262, as shown in FIG. 26. After the second layer 292 fails, it then retracts from the deformed portion 291 of the first layer 290 as shown by arrows 294 in FIG. 26. As long as the inside surface 288 and outside surface 296 of the first layer 290 are sterile prior to failure of the second layer 292, the penetrating member 262 will remain sterile as it passes through the first layer 290 once the first layer eventually fails. Such a multiple layer sterility barrier 258 can be used for any of the embodiments discussed herein. The multiple layer sterility barrier 258 can also include three or more layers.

Figure 27:
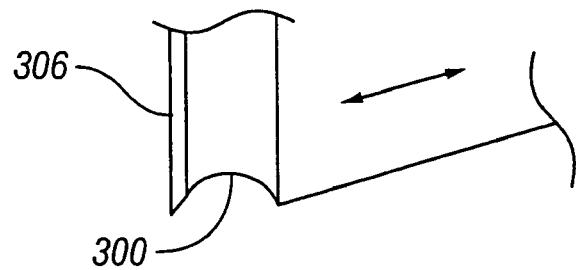
FIGS. 27 and 28 illustrate an embodiment of a drive member coupled to a driver wherein the drive member includes a cutting member having a sharpened edge which is configured to cut through a sterility barrier of a penetrating member slot during a lancing cycle in order for the drive member to make contact with the penetrating member.
Figure 28:
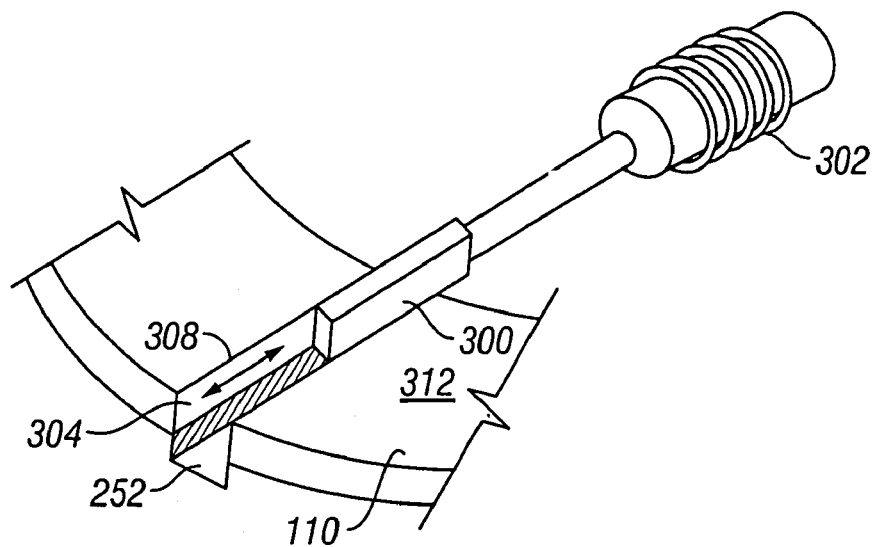

Referring to FIGS. 27 and 28, an embodiment of a drive member 300 coupled to a driver 302 wherein the drive member 300 includes a cutting member 304 having a sharpened edge 306 which is configured to cut through a sterility barrier 258 of a penetrating member slot 252 during a lancing cycle in order for the drive member 300 to make contact with a penetrating member. An optional lock pin 308 on the cutting member 304 can be configured to engage the top surface 310 of the base plate 312 in order to prevent distal movement of the cutting member 304 with the drive member 300 during a lancing cycle.

Figure 29:
FIGS. 29 and 30 illustrate an embodiment of a penetrating member slot in longitudinal section having a ramped portion disposed at a distal end of the penetrating member slot and a drive member with a cutting edge at a distal end thereof for cutting through a sterility barrier during a lancing cycle.
Figure 30:
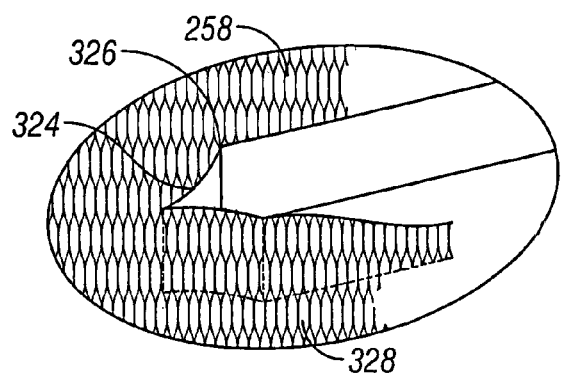

FIGS. 29 and 30 illustrate an embodiment of a penetrating member slot 316 in longitudinal section having a ramped portion 318 disposed at a distal end 320 of the penetrating member slot. A drive member 322 is shown partially disposed within the penetrating member slot 316. The drive member 322 has a cutting edge 324 at a distal end 326 thereof for cutting through a sterility barrier 328 during a lancing cycle. FIG. 30 illustrates the cutting edge 324 cutting through the sterility barrier 328 during a lancing cycle with the cut sterility barrier 328 peeling away from the cutting edge 324.

Figure 31:
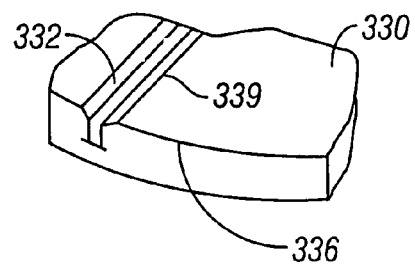
FIGS. 31-34 illustrate drive member slots in a penetrating member cartridge wherein at least a portion of the drive member slots have a tapered opening which is larger in transverse dimension at the top of the drive member slot than at the bottom of the drive member slot.
Figure 32:
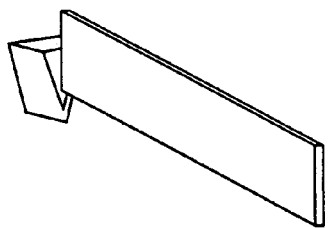
Figure 33:
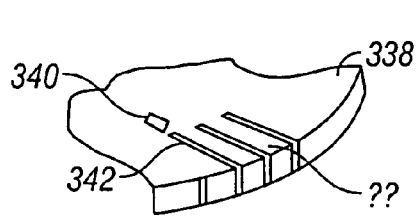
Figure 34:
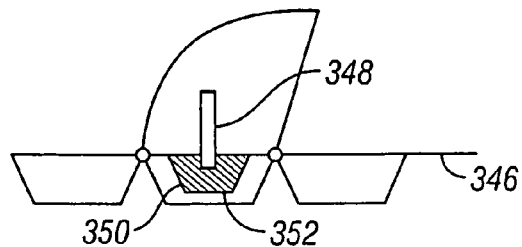

FIGS. 31-34 illustrate drive member slots in a base plate 330 of a penetrating member cartridge wherein at least a portion of the drive member slots have a tapered opening which is larger in transverse dimension at a top surface of the base plate than at the bottom of the drive member slot. FIG. 31 illustrates a base plate 330 with a penetrating member slot 332 that is tapered at the input 334 at the top surface 336 of the base plate 330 along the entire length of the penetrating member slot 332. In such a configuration, the penetrating member slot and drive member slot (not shown) would be in communication and continuous along the entire length of the slot 332. As an optional alternative, a base plate 338 as shown in FIGS. 32 and 33 can have a drive member slot 340 that is axially separated from the corresponding penetrating member slot 342. With this configuration, the drive member slot 340 can have a tapered configuration and the penetrating member slot 342 can have a straight walled configuration. In addition, this configuration can be used for corrugated embodiments of base plates 346 as shown in FIG. 34. In FIG. 34, a drive member 348 is disposed within a drive member slot 350. A penetrating member contact surface 352 is disposed on the drive member 348. The contact surface 352 has a tapered configuration that will facilitate lateral alignment of the drive member 348 with the drive member slot 350.

Figure 35:
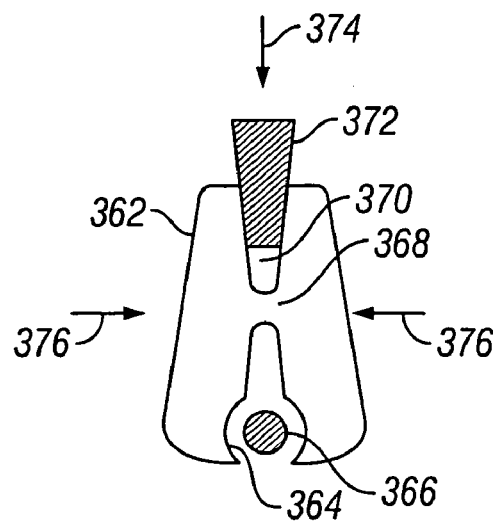
FIGS. 35-37 illustrate an embodiment of a penetrating member cartridge and penetrating member drive member wherein the penetrating member drive member has a contoured jaws configured to grip a penetrating member shaft.
Figure 36:
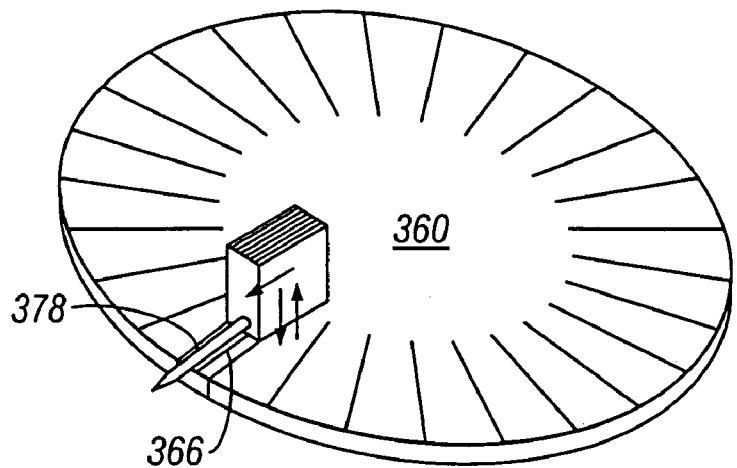
Figure 37:
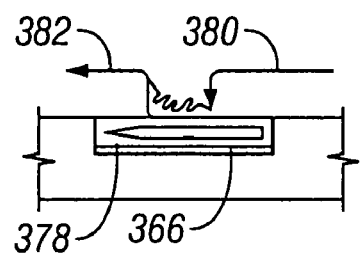

FIGS. 35-37 illustrate an embodiment of a penetrating member cartridge 360 and drive member 362 wherein the drive member 362 has contoured jaws 364 configured to grip a penetrating member shaft 366. In FIG. 35, the drive member 362 and penetrating member shaft 366 are shown in transverse cross section with the contoured jaws 364 disposed about the penetrating member shaft 366. A pivot point 368 is disposed between the contoured jaws 364 and a tapered compression slot 370 in the drive member 362. A compression wedge 372 is shown disposed within the tapered compression slot 370. Insertion of the compression wedge 372 into the compression slot 370 as indicated by arrow 374, forces the contoured jaws 364 to close about and grip the penetrating member shaft 366 as indicated by arrows 376.

FIG. 36 shows the drive member 362 in position about a penetrating member shaft 366 in a penetrating member slot 378 in the penetrating member cartridge 360. The drive member can be actuated by the methods discussed above with regard to other drive member and driver embodiments. FIG. 37 is an elevational view in longitudinal section of the penetrating member shaft 166 disposed within the penetrating member slot 378. The arrows 380 and 382 indicate in a general way, the path followed by the drive member 362 during a lancing cycle. During a lancing cycle, the drive member comes down into the penetrating member slot 378 as indicated by arrow 380 through an optional sterility barrier (not shown). The contoured jaws of the drive member then clamp about the penetrating member shaft 366 and move forward in a distal direction so as to drive the penetrating member into the skin of a patient as indicated by arrow 382.

Figure 38:
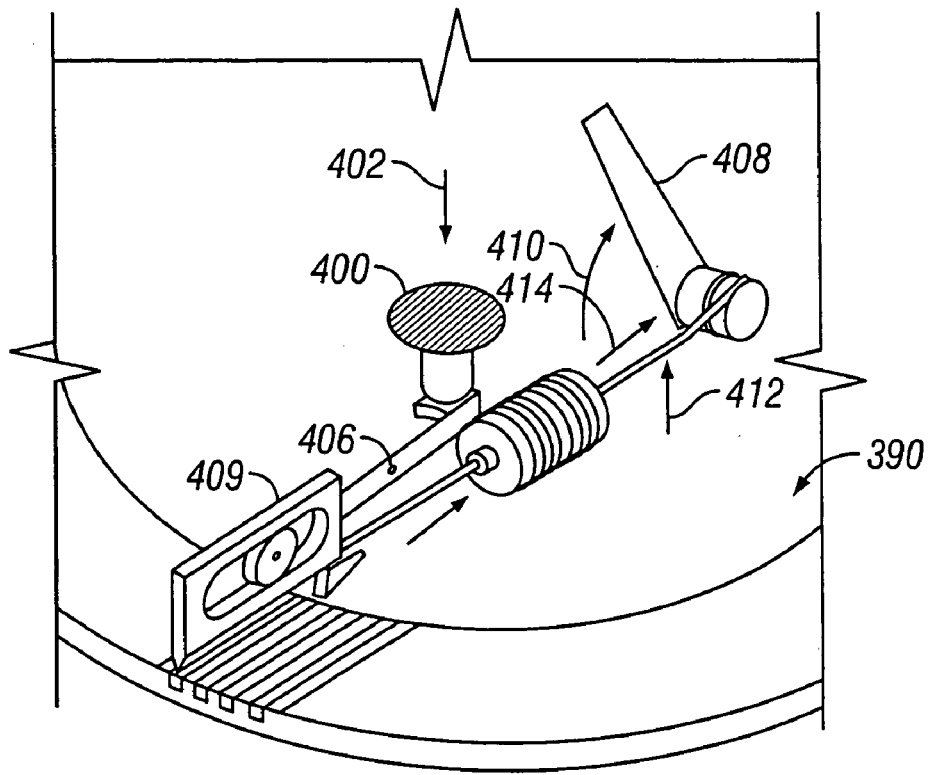
FIGS. 38 and 39 show a portion of a lancing device having a lid that can be opened to expose a penetrating member cartridge cavity for removal of a used penetrating member cartridge and insertion of a new penetrating member cartridge.
Figure 39:
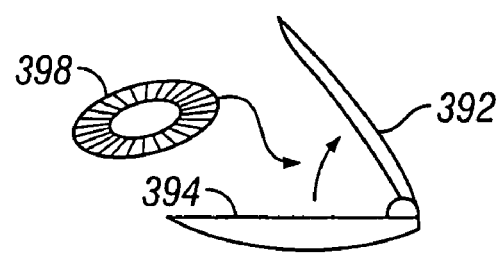

FIGS. 38 and 39 show a portion of a lancing device 390 having a lid 392 that can be opened to expose a penetrating member cartridge cavity 394 for removal of a used penetrating member cartridge 396 and insertion of a new penetrating member cartridge 398. Depression of button 400 in the direction indicated by arrow 402 raises the drive member 404 from the surface of the penetrating member cartridge 396 by virtue of lever action about pivot point 406. Raising the lid 392 actuates the lever arm 408 in the direction indicated by arrow 410 which in turn applies a tensile force to cable 412 in the direction indicated by arrow 414. This action pulls the drive member back away from the penetrating member cartridge 396 so that the penetrating member cartridge 396 can be removed from the lancing device 390. A new penetrating member cartridge 398 can then be inserted into the lancing device 390 and the steps above reversed in order to position the drive member 404 above the penetrating member cartridge 398 in an operational position.

Figure 40:
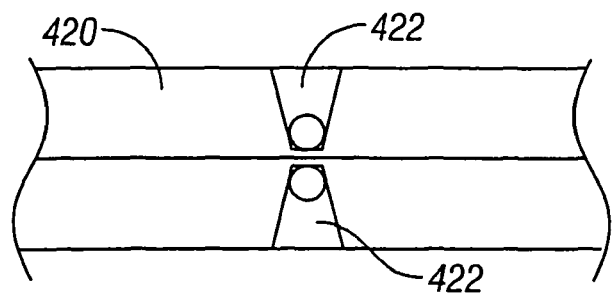
FIGS. 40 and 41 illustrate a penetrating member cartridge that has penetrating member slots on both sides.
Figure 41:
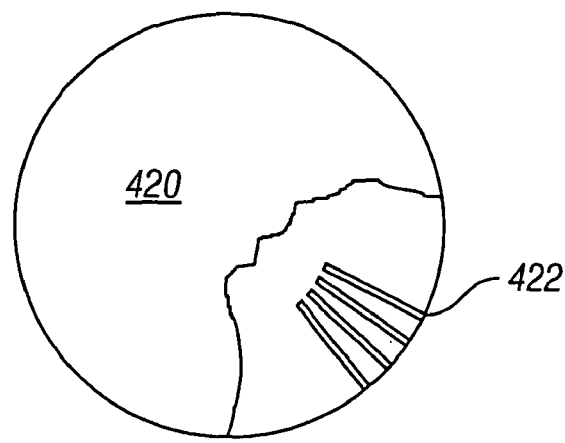

FIGS. 40 and 41 illustrate a penetrating member cartridge 420 that has penetrating member slots 422 on a top side 424 and a bottom side 426 of the penetrating member cartridge 420. This allows for a penetrating member cartridge 420 of a diameter D to store for use twice the number of penetrating members as a one sided penetrating member cartridge of the same diameter D.

Figure 42:
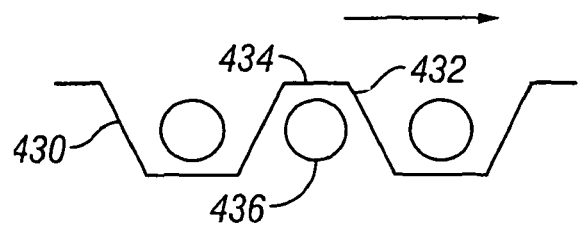
FIGS. 42-44 illustrate end and perspective views of a penetrating member cartridge having a plurality of penetrating member slots formed from a corrugated surface of the penetrating member cartridge.
Figure 43:
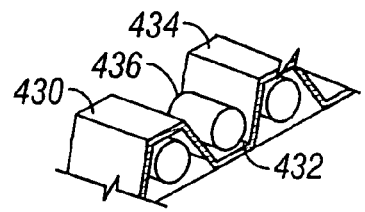
Figure 44:
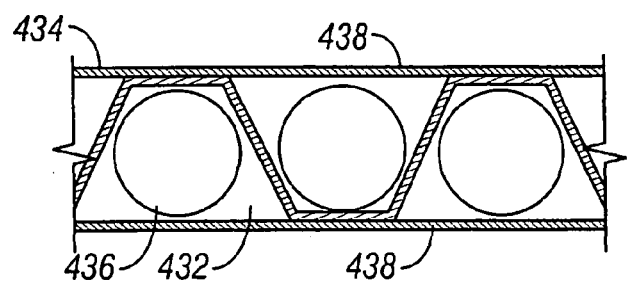

FIGS. 42-44 illustrate end and perspective views of a penetrating member cartridge 430 having a plurality of penetrating member slots 432 formed from a corrugated surface 434 of the penetrating member cartridge 430. Penetrating members 436 are disposed on both sides of the penetrating member cartridge 430. A sterility barrier 438 is shown disposed over the penetrating member slots 432 in FIG. 44.

Figure 45:
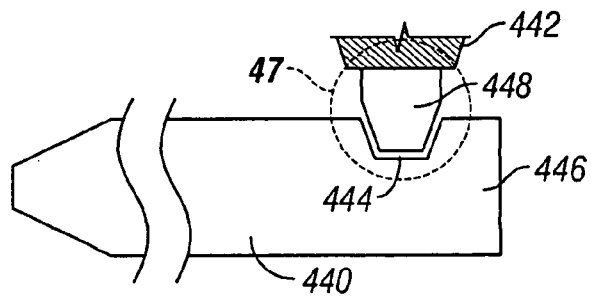
FIGS. 45-48 illustrate embodiments of a penetrating member and drive member wherein the penetrating member has a slotted shaft and the drive member has a protuberance configured to mate with the slot in the penetrating member shaft.
Figure 46:
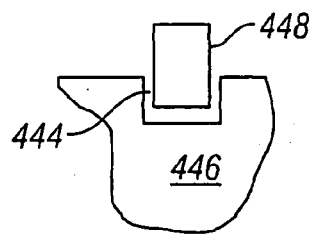
Figure 47:
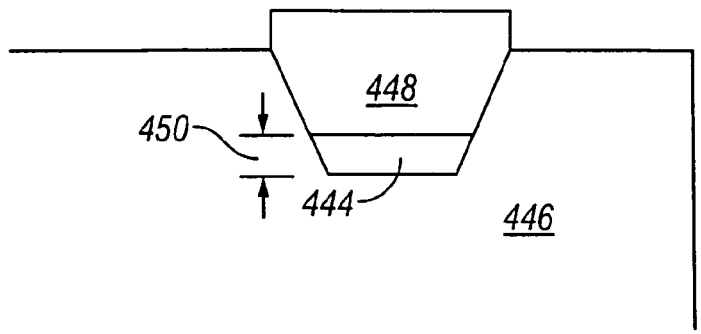

FIGS. 45-48 illustrate embodiments of a penetrating member 440 and drive member 442 wherein the penetrating member 440 has a transverse slot 444 in the penetrating member shaft 446 and the drive member 442 has a protuberance 448 configured to mate with the transverse slot 444 in the penetrating member shaft 446. FIG. 45 shows a protuberance 448 having a tapered configuration that matches a tapered configuration of the transverse slot 444 in the penetrating member shaft 446. FIG. 46 illustrates an optional alternative embodiment wherein the protuberance 448 has straight walled sides that are configured to match the straight walled sides of the transverse slot 444 shown in FIG. 46. FIG. 47 shows a tapered protuberance 448 that is configured to leave an end gap 450 between an end of the protuberance 448 and a bottom of the transverse slot in the penetrating member shaft 446.

Figure 48:
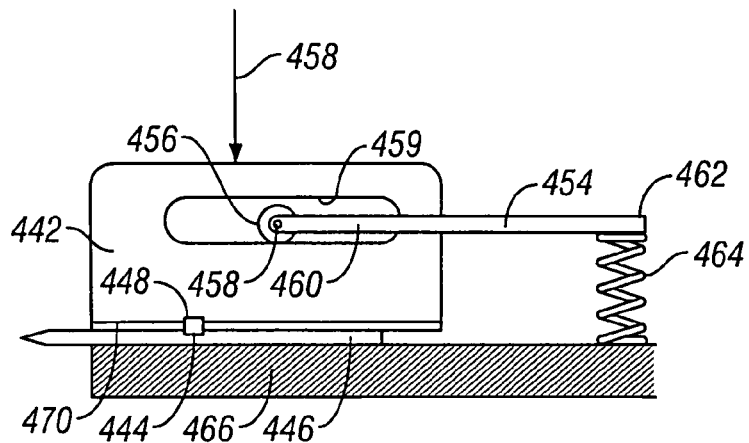

FIG. 48 illustrates a mechanism 452 to lock the drive member 442 to the penetrating member shaft 446 that has a lever arm 454 with an optional bearing 456 on the first end 458 thereof disposed within a guide slot 459 of the drive member 442. The lever arm 454 has a pivot point 460 disposed between the first end 458 of the lever arm 454 and the second end 462 of the lever arm 454. A biasing force is disposed on the second end 462 of the lever arm 454 by a spring member 464 that is disposed between the second end 462 of the lever arm 454 and a base plate 466. The biasing force in the direction indicated by arrow 468 forces the penetrating member contact surface 470 of the drive member 442 against the outside surface of the penetrating member 446 and, in addition, forces the protuberance 448 of the drive member 442 into the transverse slot 444 of the penetrating member shaft 446.

Figure 49:
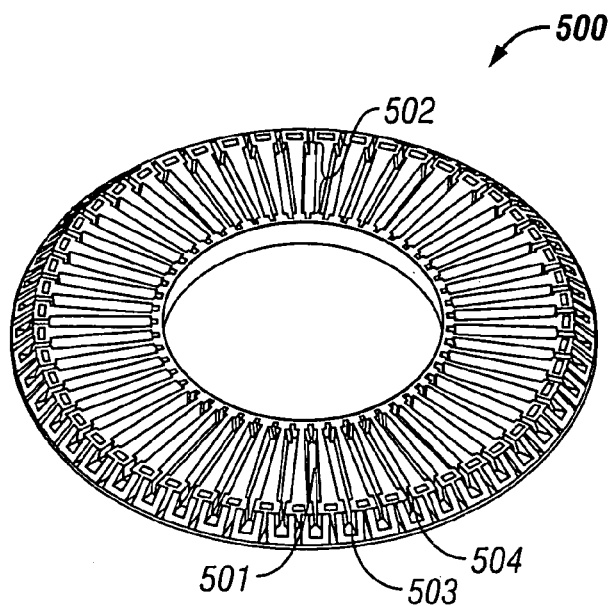
FIG. 49 is a perspective view of a cartridge according to the present invention.

Referring now to FIG. 49, another embodiment of a replaceable cartridge 500 suitable for housing a plurality of individually moveable penetrating members (not shown) will be described in further detail. Although cartridge 500 is shown with a chamfered outer periphery, it should also be understood that less chamfered and unchamfered embodiments of the cartridge 500 may also be adapted for use with any embodiment of the present invention disclosed herein. The penetrating members slidably coupled to the cartridge may be a bare lancet or bare elongate member without outer molded part or body pieces as seen in conventional lancet. The bare design reduces cost and simplifies manufacturing of penetrating members for use with the present invention. The penetrating members may be retractable and held within the cartridge so that they are not able to be used again. The cartridge is replaceable with a new cartridge once all the piercing members have been used. The lancets or penetrating members may be fully contained in the used cartridge so at to minimize the chance of patient contact with such waste.

Figure 50:
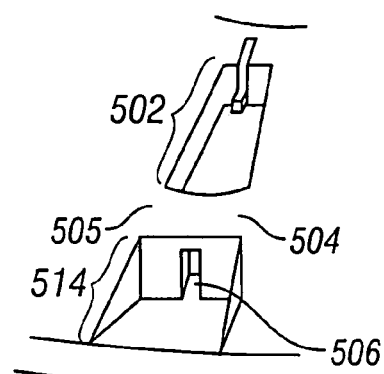
FIGS. 50 and 51 show close-ups of outer peripheries various cartridges.
Figure 51:
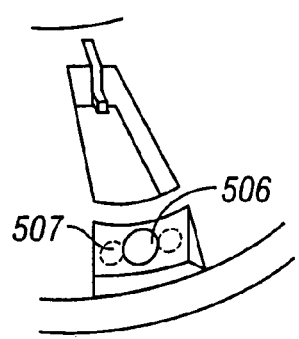

As can be seen in FIG. 49, the cartridge 500 may include a plurality of cavities 501 for housing a penetrating member. In this embodiment, the cavity 501 may have a longitudinal opening 502 associated with the cavity. The cavity 501 may also have a lateral opening 503 allowing the penetrating member to exit radially outward from the cartridge. As seen in FIG. 49, the outer radial portion of the cavity may be narrowed. The upper portion of this narrowed area may also be sealed or swaged to close the top portion 505 and define an enclosed opening 506 as shown in FIG. 50. Optionally, the narrowed area 504 may retain an open top configuration, though in some embodiments, the foil over the gap is unbroken, preventing the penetrating member from lifting up or extending upward out of the cartridge. The narrowed portion 504 may act as a bearing and/or guide for the penetrating member. FIG. 51 shows that the opening 506 may have a variety of shapes such as but not limited to, circular, rectangular, triangular, hexagonal, square, or combinations of any or all of the previous shapes. Openings 507 (shown in phantom) for other microfluidics, capillary tubes, or the like may also be incorporated in the immediate vicinity of the opening 506. In some optional embodiments, such openings 507 may be configured to surround the opening 506 in a concentric or other manner.

Figure 52:
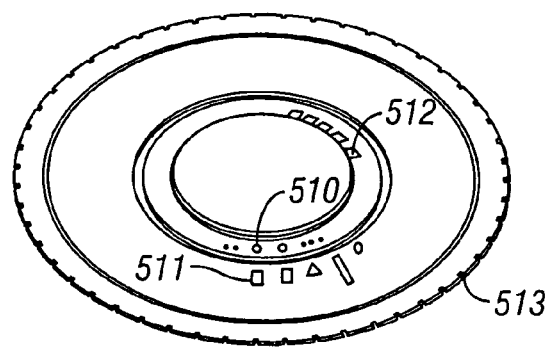
FIG. 52 is a perspective view of an underside of a cartridge.

Referring now to FIG. 52, the underside of a cartridge 500 will be described in further detail. This figures shows many features on one cartridge 500. It should be understood that a cartridge may include some, none, or all of these features, but they are shown in FIG. 52 for ease of illustration. The underside may include indentations or holes 510 close to the inner periphery for purpose of properly positioning the cartridge to engage a penetrating member gripper and/or to allow an advancing device (shown in FIGS. 56B and 56C) to rotate the cartridge 500. Indentations or holes 511 may be formed along various locations on the underside of cartridge 500 and may assume various shapes such as but not limited to, circular, rectangular, triangular, hexagonal, square, or combinations of any or all of the previous shapes. Notches 512 may also be formed along the inner surface of the cartridge 500 to assist in alignment and/or rotation of the cartridge. It should be understood of course that some of these features may also be placed on the topside of the cartridge in areas not occupied by cavities 501 that house the penetrating members. Notches 513 may also be incorporated along the outer periphery of the cartridge. These notches 513 may be used to gather excess material from the sterility barrier 28 (not shown) that may be used to cover the angled portion 514 of the cartridge. In the present embodiment, the cartridge has a flat top surface and an angled surface around the outside. Welding a foil type sterility barrier over that angled surface, the foil folds because of the change in the surfaces which is now at 45 degrees. This creates excess material. The grooves or notches 513 are there as a location for that excess material. Placing the foil down into those grooves 513 which may tightly stretch the material across the 45 degree angled surface. Although in this embodiment the surface is shown to be at 45 degrees, it should be understood that other angles may also be used. For example, the surface may be at any angle between about 3 degrees to 90 degrees, relative to horizontal. The surface may be squared off. The surface may be unchamfered. The surface may also be a curved surface or it may be combinations of a variety of angled surfaces, curved and straights surfaces, or any combination of some or all of the above.

Referring now to FIGS. 53-54, the sequence in which the cartridge 500 is indexed and penetrating members are actuated will now be described. It should be understood that some steps described herein may be combined or taken out of order without departing from the spirit of the invention. These sequence of steps provides vertical and horizontal movement used with the present embodiment to load a penetrating member onto the driver.

As previously discussed, each cavity on the cartridge may be individually sealed with a foil cover or other sterile enclosure material to maintain sterility until or just before the time of use. In the present embodiment, penetrating members are released from their sterile environments just prior to actuation and are loaded onto a launcher mechanism for use. Releasing the penetrating member from the sterile environment prior to launch allows the penetrating member in the present embodiment to be actuated without having to pierce any sterile enclosure material which may dull the tip of the penetrating member or place contaminants on the member as it travels towards a target tissue. A variety of methods may be used accomplish this goal.

Figure 53A:
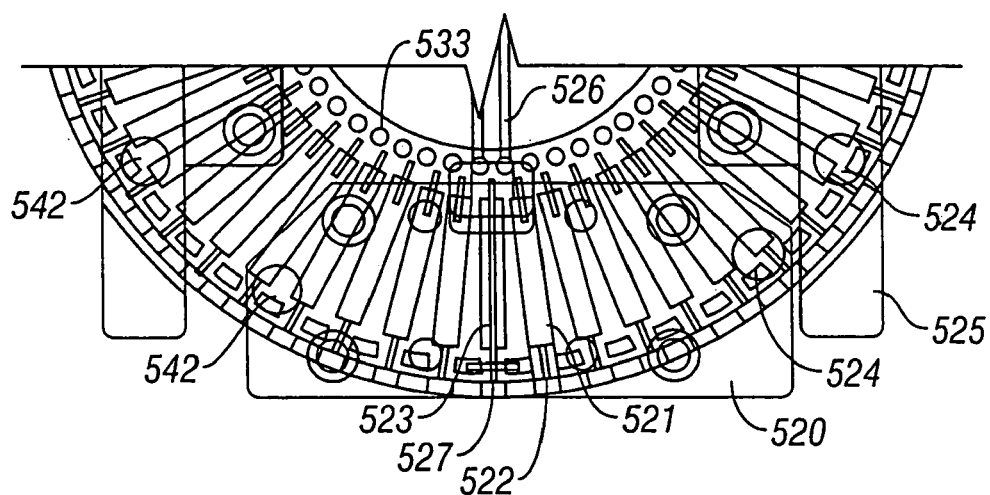
FIG. 53A shows a top down view of a cartridge and the punch and pusher devices.
Figure 53B:
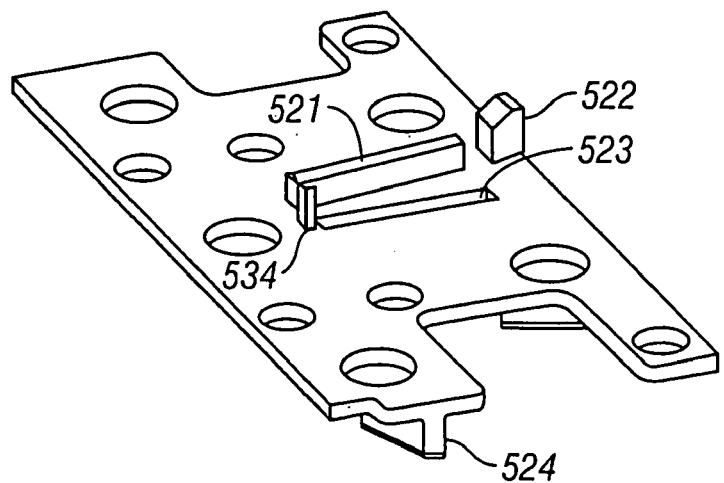
FIG. 53B is a perspective view of one embodiment of a punch plate.
Figure 54A:
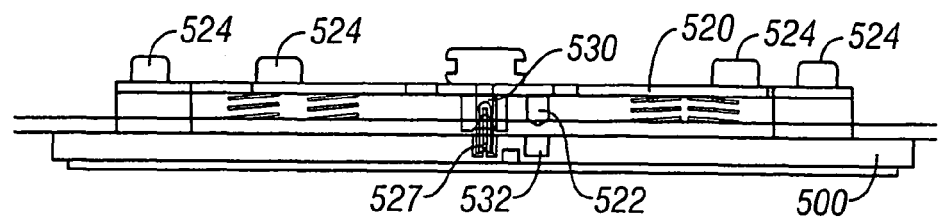
FIGS. 54A-54G show a sequence of motion for the punch plate, the cartridge, and the cartridge pusher.

FIG. 53A shows one embodiment of penetrating member release device, which in this embodiment is a punch plate 520 that is shown in a see-through depiction for ease of illustration. The punch plate 520 may include a first portion 521 for piercing sterile material covering the longitudinal opening 502 and a second portion 522 for piercing material covering the lateral opening 503. A slot 523 allows the penetrating member gripper to pass through the punch plate 520 and engage a penetrating member housed in the cartridge 500. The second portion 522 of the punch plate down to engage sterility barrier angled at about a 45 degree slope. Of course, the slope of the barrier may be varied. The punch portion 522 first contacts the rear of the front pocket sterility barrier and as it goes down, the cracks runs down each side and the barrier is pressed down to the bottom of the front cavity. The rear edge of the barrier first contacted by the punch portion 522 is broken off and the barrier is pressed down, substantially cleared out of the way. These features may be more clearly seen in FIG. 53B. The punch portion 521 may include a blade portion down the centerline. As the punch comes down, that blade may be aligned with the center of the cavity, cutting the sterility barrier into two pieces. The wider part of the punch 521 then pushes down on the barrier so the they align parallel to the sides of the cavity. This creates a complete and clear path for the gripper throughout the longitudinal opening of the cavity. Additionally, as seen in FIGS. 53B and 54A, a plurality of protrusion 524 are positioned to engage a cam (FIG. 55A) which sequences the punching and other vertical movement of punch plate 520 and cartridge pusher 525. The drive shaft 526 from a force generator (not shown) which is used to actuate the penetrating member 527.

Referring now to FIGS. 54A-F, the release and loading of the penetrating members are achieved in the following sequence. FIG. 54A shows the release and loading mechanism in rest state with a dirty bare penetrating member 527 held in a penetrating member gripper 530. This is the condition of the device between lancing events. When the time comes for the patient to initiate another lancing event, the used penetrating member is cleared and a new penetrating member is loaded, just prior to the actual lancing event. The patient begins the loading of a new penetrating member by operating a setting lever to initiate the process. The setting lever may operate mechanically to rotate a cam (see FIG. 55A) that moves the punch plate 520 and cartridge pusher 525. In other embodiments, a stepper motor or other mover such as but not limited to, a pneumatic actuator, hydraulic actuator, or the like are used to drive the loading sequence.

Figure 54B:
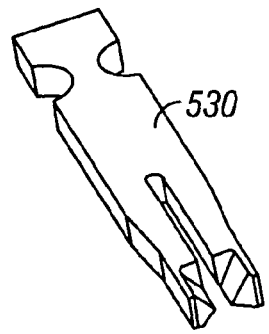

FIG. 54B shows one embodiment of penetrating member gripper 530 in more detail. The penetrating member gripper 530 may be in the form of a tuning fork with sharp edges along the inside of the legs contacting the penetrating member. In some embodiments, the penetrating member may be notched, recessed, or otherwise shaped to receive the penetrating member gripper. As the gripper 530 is pushed down on the penetrating member, the legs are spread open elastically to create a frictional grip with the penetrating member such as but not limited to bare elongate wires without attachments molded or otherwise attached thereon. In some embodiments, the penetrating member is made of a homogenous material without any additional attachments that are molded, adhered, glued or otherwise added onto the penetrating member.

In some embodiments, the gripper 530 may cut into the sides of the penetrating member. The penetrating member in one embodiment may be about 300 microns wide. The grooves that form in the side of the penetrating member by the knife edges are on the order of about 5-10 microns deep and are quite small. In this particular embodiment, the knife edges allow the apparatus to use a small insertion force to get the gripper onto the penetrating member, compared to the force to remove the penetrating member from the gripper the longitudinal axis of an elongate penetrating member. Thus, the risk of a penetrating member being detached during actuation are reduced. The gripper 530 may be made of a variety of materials such as, but not limited to high strength carbon steel that is heat treated to increased hardness, ceramic, substrates with diamond coating, composite reinforced plastic, elastomer, polymer, and sintered metals. Additionally, the steel may be surface treated. The gripper 130 may have high gripping force with low friction drag on solenoid or other driver.

Figure 54C:
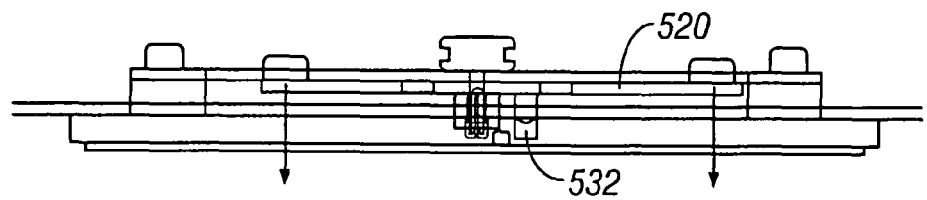

As seen in FIG. 54C, the sequence begins with punch plate 520 being pushed down. This results in the opening of the next sterile cavity 532. In some embodiment, this movement of punch plate 520 may also result in the crimping of the dirty penetrating member to prevent it from being used again. This crimping may result from a protrusion on the punch plate bending the penetrating member or pushing the penetrating member into a groove in the cartridge that hold the penetrating member in place through an interference fit. As seen in FIGS. 53B and 54C, the punch plate 520 has a protrusion or punch shaped to penetrate a longitudinal opening 502 and a lateral opening 503 on the cartridge. The first portion 521 of the punch that opens cavity 532 is shaped to first pierce the sterility barrier and then push, compresses, or otherwise moves sterile enclosure material towards the sides of the longitudinal opening 502. The second portion 522 of the punch pushes down the sterility barrier at lateral opening or penetrating member exit 503 such that the penetrating member does not pierce any materials when it is actuated toward a tissue site.

Figure 54D:
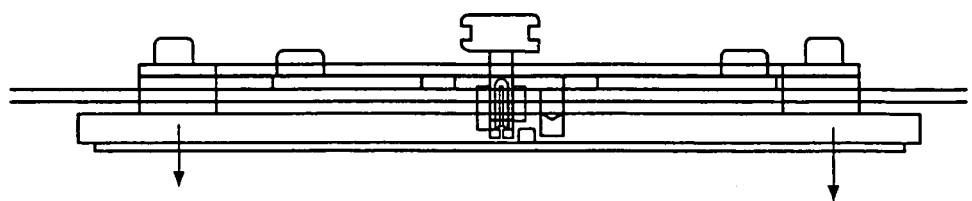

Referring now to FIG. 54D, the cartridge pusher 525 is engaged by the cam 550 (not shown) and begins to push down on the cartridge 500. The punch plate 520 also travels downward with the cartridge 500 until it is pushed down to it maximum downward position, while the penetrating member gripper 530 remains vertically stationary. This joint downward motion away from the penetrating member gripper 530 will remove the penetrating member from the gripper. The punch plate 520 essentially pushes against the penetrating member with protrusion 534 (FIG. 55A), holding the penetrating member with the cartridge, while the cartridge 500 and the punch plate 520 is lowered away from the penetrating member gripper 530 which in this embodiment remains vertically stationary. This causes the stripping of the used penetrating member from the gripper 530 (FIG. 45D) as the cartridge moves relative to the gripper.

Figure 54E:
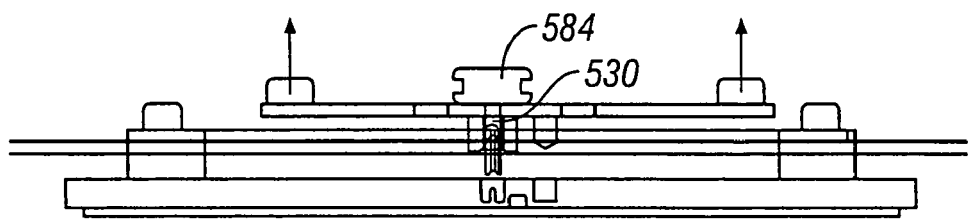
Figure 54F:
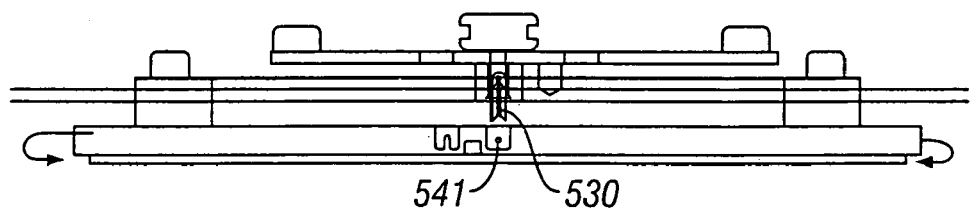

At this point as seen in FIG. 54E, the punch plate 520 retracts upward and the cartridge 500 is pushed fully down, clear of the gripper 530. Now cleared of obstructions and in a rotatable position, the cartridge 500 increments one pocket or cavity in the direction that brings the newly released, sterile penetrating member in cavity 532 into alignment with the penetrating member gripper 530, as see in FIG. 54F. The rotation of the cartridge occurs due to fingers engaging the holes or indentations 533 on the cartridge, as seen in FIG. 54A. In some embodiments, these indentations 533 do not pass completely through cartridge 500. In other embodiments, these indentations are holes passing completely through. The cartridge has a plurality of little indentations 533 on the top surface near the center of the cartridge, along the inside diameter. In the one embodiment, the sterility barrier is cut short so as not to cover these plurality of indentations 533. It should be understood of course that these holes may be located on bottom, side or other accessible surface. These indentations 533 have two purposes. The apparatus may have one or a plurality of locator pins, static pins, or other keying feature that dos not move. In this embodiment, the cartridge will only set down into positions where the gripper 530 is gripping the penetrating member. To index the cassette, the cartridge is lifted off those pins or other keyed feature, rotated around, and dropped onto those pins for the next position. The rotating device is through the use of two fingers: one is a static pawl and the other one is a sliding finger. They engage with the holes 533. The fingers are driven by a slider that may be automatically actuated or actuated by the user. This may be occur mechanically or through electric or other powered devices. Halfway through the stroke, a finger may engage and rotate around the cartridge. A more complete description can be found with text associated with FIGS. 56B-56C.

Figure 54G:
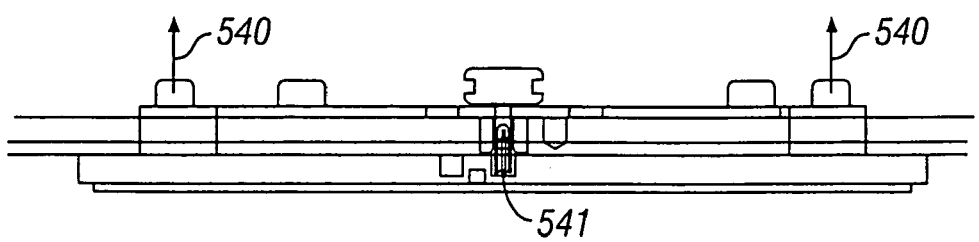

Referring now to FIG. 54G, with the sterile penetrating member in alignment, the cartridge 500 is released as indicated by arrows 540 and brought back into contact with the penetrating member gripper 530. The new penetrating member 541 is inserted into the gripper 530, and the apparatus is ready to fire once again. After launch and in between lancing events for the present embodiment, the bare lancet or penetrating member 541 is held in place by gripper 530, preventing the penetrating member from accidentally protruding or sliding out of the cartridge 500.

Figure 55A:
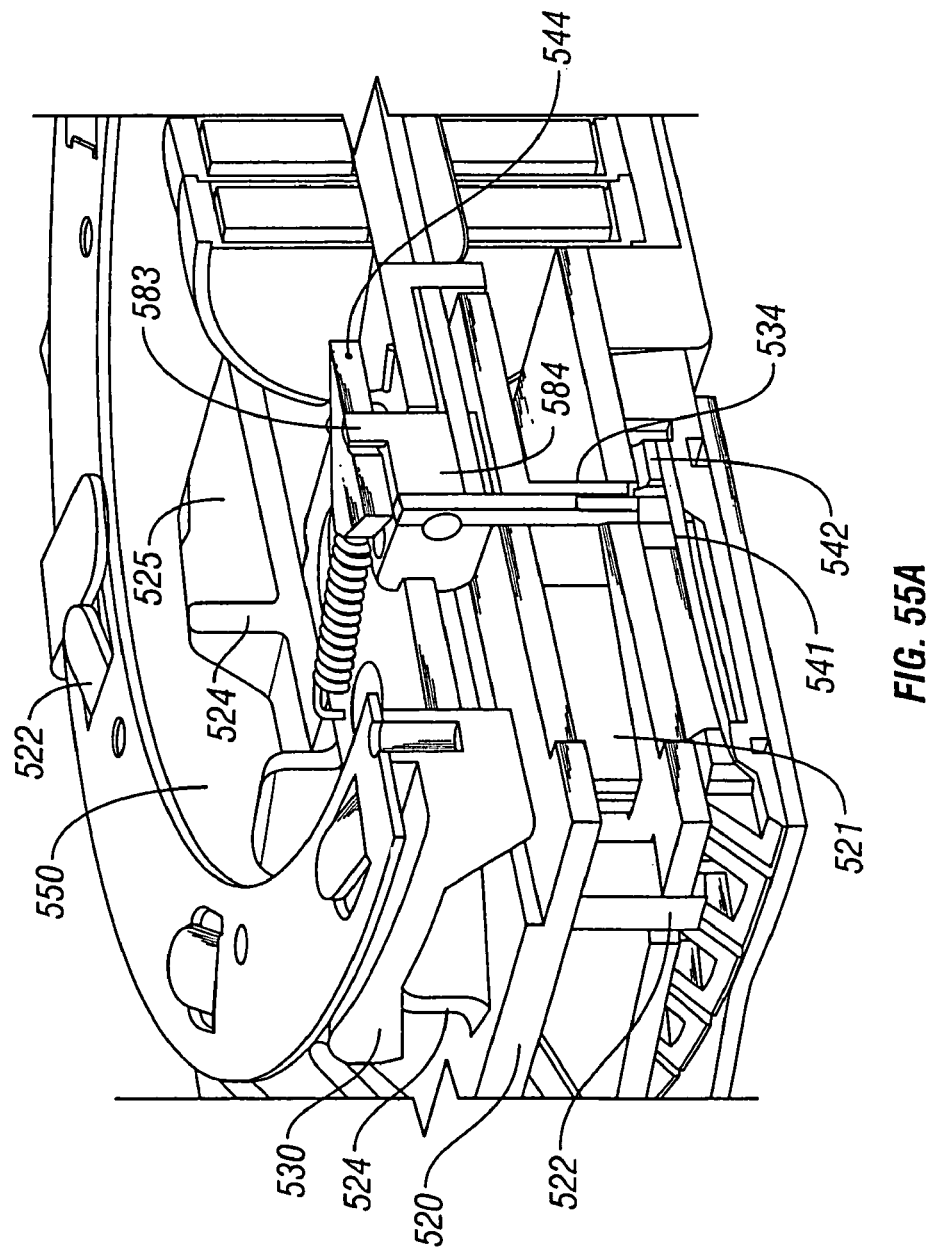
FIGS. 55A-55B show cross-sections of the system according to the present invention.
Figure 55B:
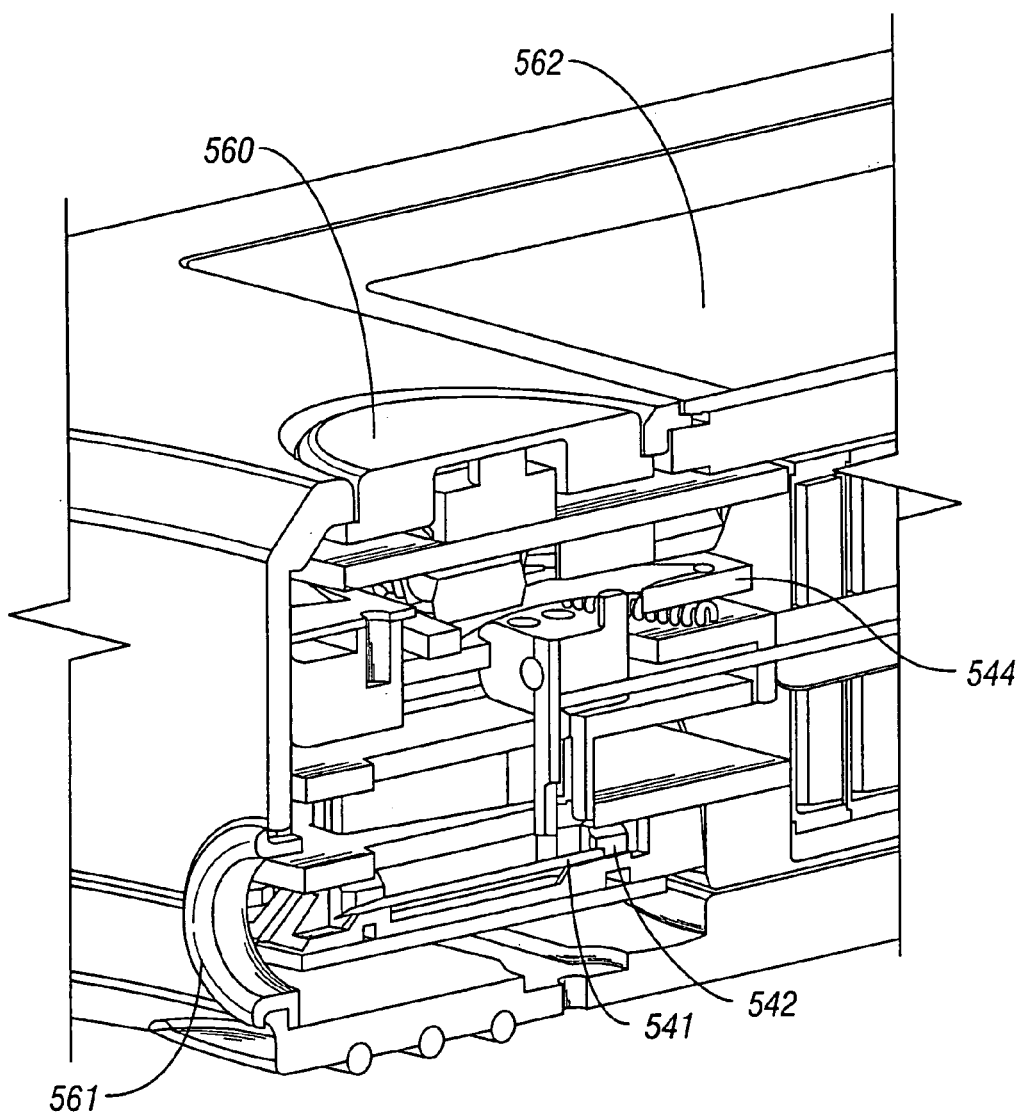

It should be understood of course, that variations can be added to the above embodiment without departing from the spirit of the invention. For example, the penetrating member 541 may be placed in a parked position in the cartridge 500 prior to launch. As seen in FIG. 55A, the penetrating member is held by a narrowed portion 542 of the cartridge, creating an interference fit which pinches the proximal end of the penetrating member. Friction from the molding or cartridge holds the penetrating member during rest, preventing the penetrating member from sliding back and forth. Of course, other methods of holding the penetrating member may also be used. As seen in FIG. 55B prior to launch, the penetrating member gripper 530 may pull the penetrating member 541 out of the portion 542. The penetrating member 541 may remain in this portion until actuated by the solenoid or other force generator coupled to the penetrating member gripper. A cam surface 544 may be used to pull the penetrating member out of the portion 542. This mechanical cam surface may be coupled to the mechanical slider driven by the patient, which may be considered a separate force generator. Thus, energy from the patient extracts the penetrating member and this reduces the drain on the device's battery if the solenoid or electric driver were to pull out the penetrating member. The penetrating member may be moved forward a small distance (on the order of about 1 mm or less) from its parked position to pull the penetrating member from the rest position gripper. After penetrating tissue, the penetrating member may be returned to the cartridge and eventually placed into the parked position. This may also occur, though not necessarily, through force provided by the patient. In one embodiment, the placing of the lancet into the parked position does not occur until the process for loading a new penetrating member is initiated by the patient. In other embodiments, the pulling out of the parked position occurs in the same motion as the penetrating member actuation. The return into the parked position may also be considered a continuous motion.

FIG. 55A also shows one embodiment of the cam and other surfaces used to coordinate the motion of the punch plate 520. For example, cam 550 in this embodiment is circular and engages the protrusions 524 on the punch plate 520 and the cartridge pusher 525. FIG. 55A also more clearly shows protrusion 534 which helps to hold the penetrating member in the cartridge 500 while the penetrating member gripper 530 pulls away from the member, relatively speaking. A ratchet surface 552 that rotates with the cam 550 may be used to prevent the cam from rotating backwards. The raising and lower of cartridge 500 and punch plate 50 used to load/unload penetrating members may be mechanically actuated by a variety of cam surfaces, springs, or the like as may be determined by one skilled in the art. Some embodiments may also use electrical or magnetic device to perform the loading, unloading, and release of bare penetrating members. Although the punch plate 520 is shown to be punching downward to displace, remove, or move the foil or other sterile environment enclosure, it should be understood that other methods such as stripping, pulling, tearing, or some combination of one or more of these methods may be used to remove the foil or sterile enclosure. For example, in other embodiments, the punch plate 520 may be located on an underside of the cartridge and punch upward. In other embodiments, the cartridge may remain vertically stationary while other parts such as the penetrating member gripper and punch plate move to load a sterile penetrating member on to the penetrating member gripper.

FIG. 55B also shows other features that may be included in the present apparatus. A fire button 560 may be included for the user to actuate the penetrating member. A front end interface 561 may be included to allow a patient to seat their finger or other target tissue for lancing. The interface 561 may be removable to be cleaned or replaced. A visual display 562 may be included to show device status, lancing performance, error reports, or the like to the patient.

Figure 56A:
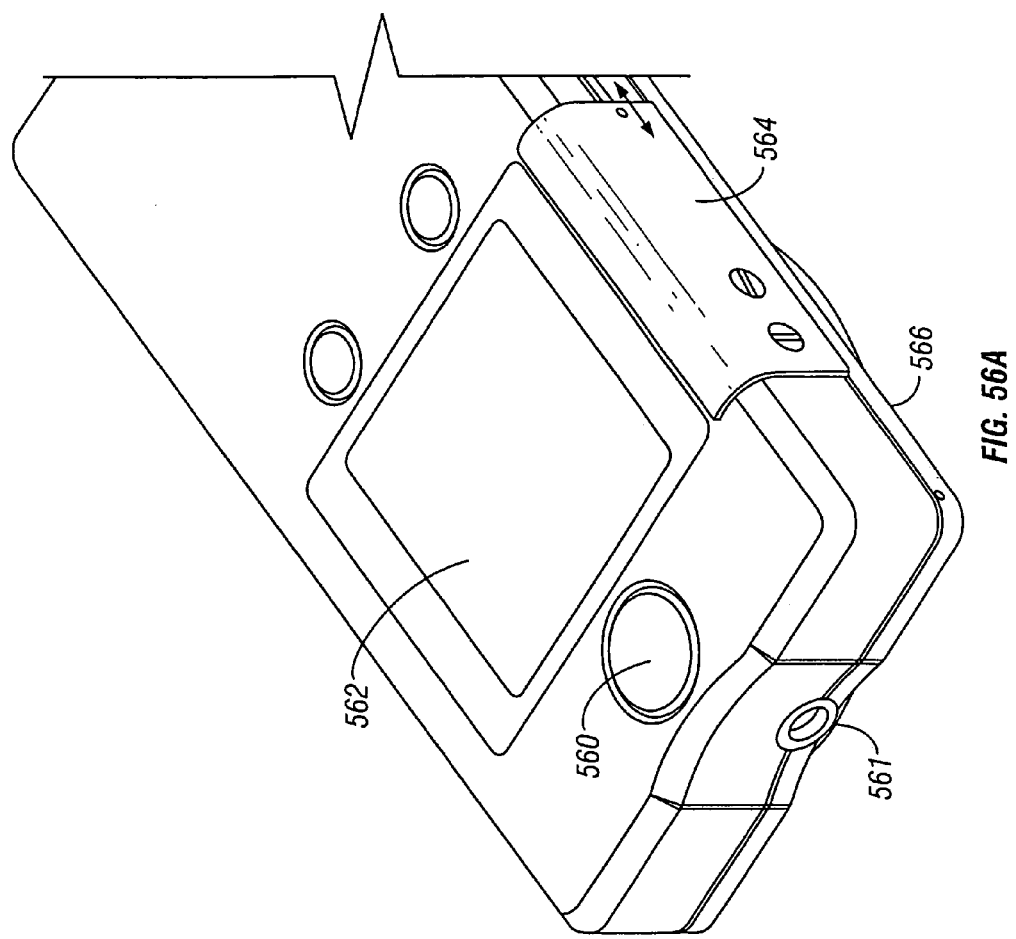
FIG. 56A shows a perspective view of the system according to the present invention.

Referring now to FIG. 56A, a mechanical slider 564 used by the patient to load new penetrating member may also be incorporated on the housing. The slider 564 may also be coupled to activate an LCD or visual display on the lancing apparatus. In addition to providing a source of energy to index the cartridge, the slider 564 may also switch the electronics to start the display. The user may use the display to select the depth of lancing or other feature. The display may go back to sleep again until it is activated again by motion of the slider 564. The underside the housing 566 may also be hinged or otherwise removable to allow the insertion of cartridge 500 into the device. The cartridge 500 may be inserted using technology current used for insertion of a compact disc or other disc into a compact disc player. In one embodiment, there may be a tray which is deployed outward to receive or to remove a cartridge. The tray may be withdrawn into the apparatus where it may be elevated, lowered, or otherwise transported into position for use with the penetrating member driver. In other embodiments, the apparatus may have a slot into which the cartridge is partially inserted at which point a mechanical apparatus will assist in completing insertion of the cartridge and load the cartridge into proper position inside the apparatus. Such device is akin to the type of compact disc player found on automobiles. The insertions/ejection and loading apparatus of these compact disc players uses gears, pulleys, cables, trays, and/or other parts that may be adapted for use with the present invention.

Figure 56B:
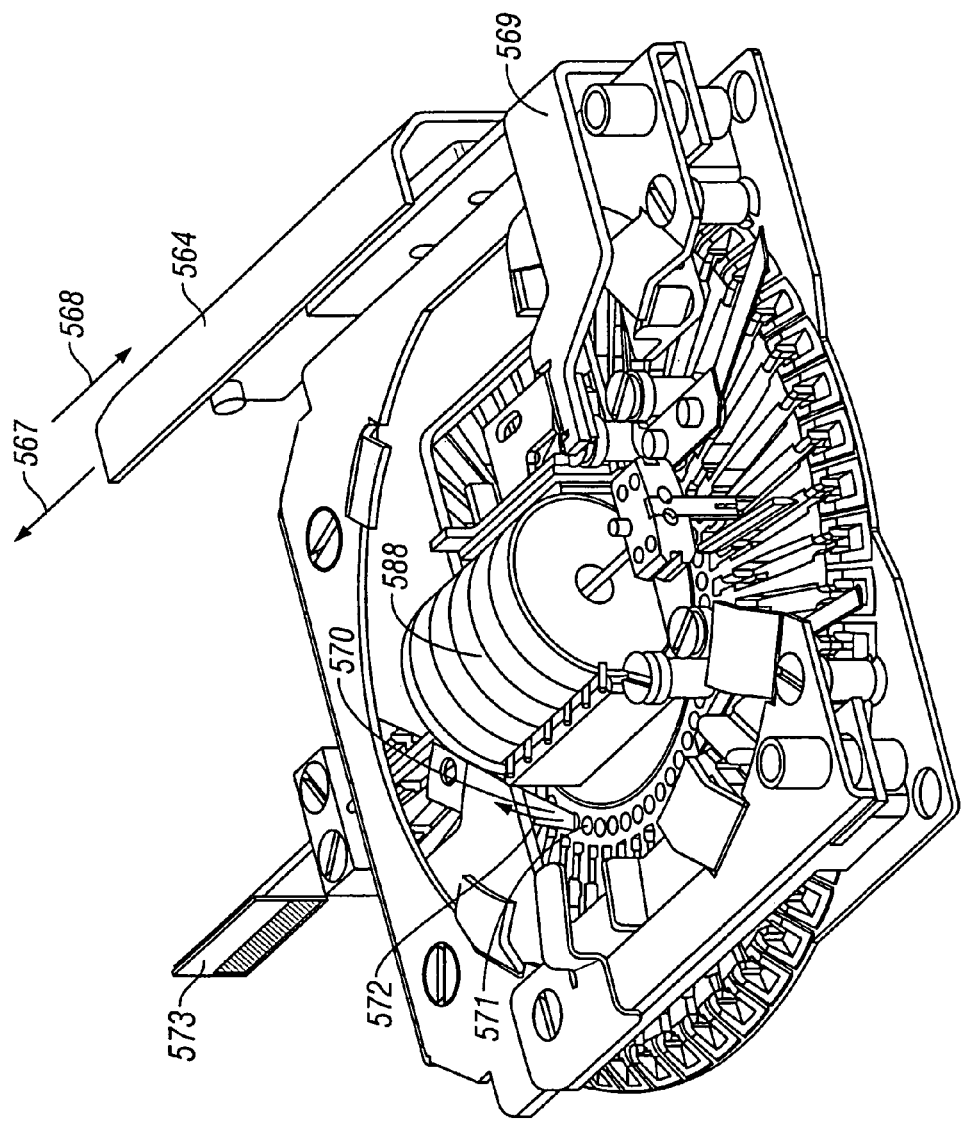
FIGS. 56B-56D are cut-away views showing mechanisms within the present invention.
Figure 66:
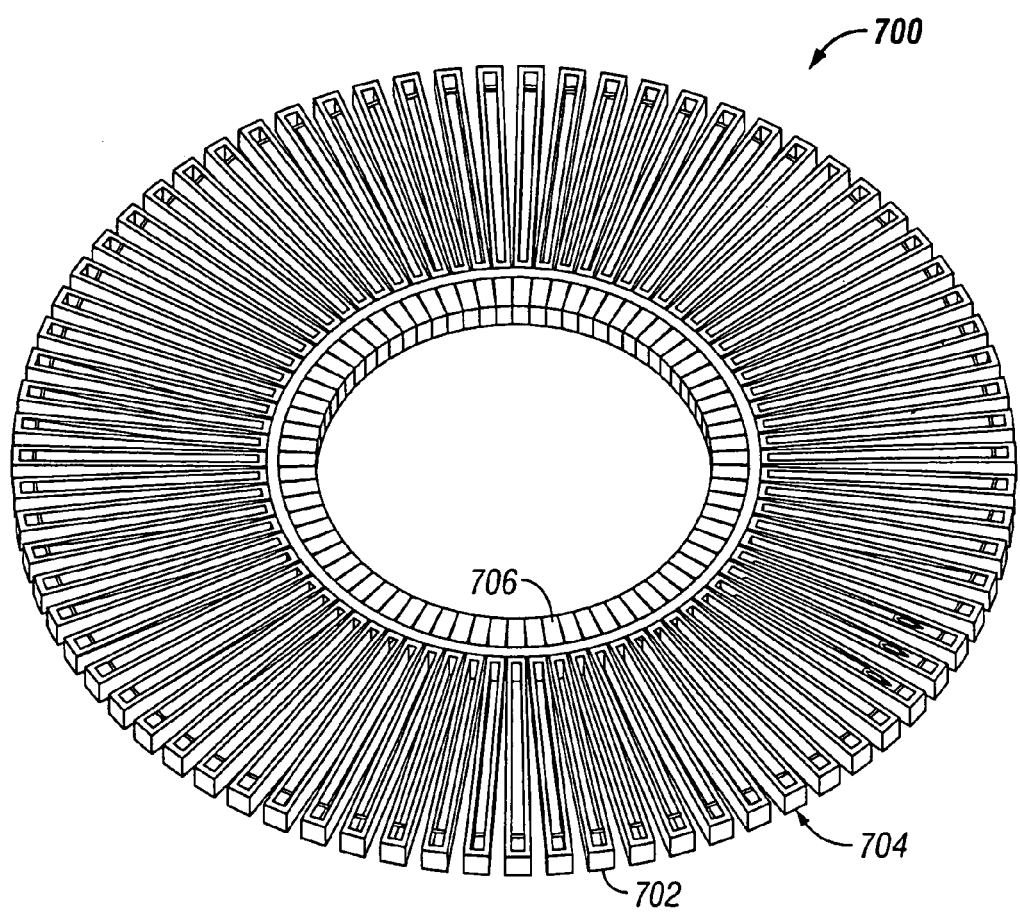
FIG. 66-68 shows a still further embodiment of a cartridge according to the present invention.

Referring now to FIG. 56B, a more detailed view of one embodiment of the slider 564 is provided. In this embodiment, the slider 564 will move initially as indicated by arrow 567. To complete the cycle, the patient will return the slider to its home position or original starting position as indicated by arrow 568. The slider 564 has an arm 569 which moves with the slider to rotate the cam 550 and engage portions 522. The motion of the slider 564 is also mechanically coupled to a finger 570 which engage the indentations 571 on cartridge 500. The finger 570 is synchronized to rotate the cartridge 500 by pulling as indicated by arrow 572 in the same plane as the cartridge. It should be understood that in some embodiments, the finger 570 pushes instead of pulls to rotate the cartridge in the correct direction. The finger 570 may also be adapted to engage ratchet surfaces 706 as seen in FIG. 66 to rotate a cartridge. The finger 570 may also incorporate vertical motion to coordinate with the rising and lowering of the cartridge 500. The motion of finger 570 may also be powered by electric actuators such as a stepper motor or other device useful for achieving motion. FIG. 56B also shows a portion of the encoder 573 used in position sensing.

Figure 56C:
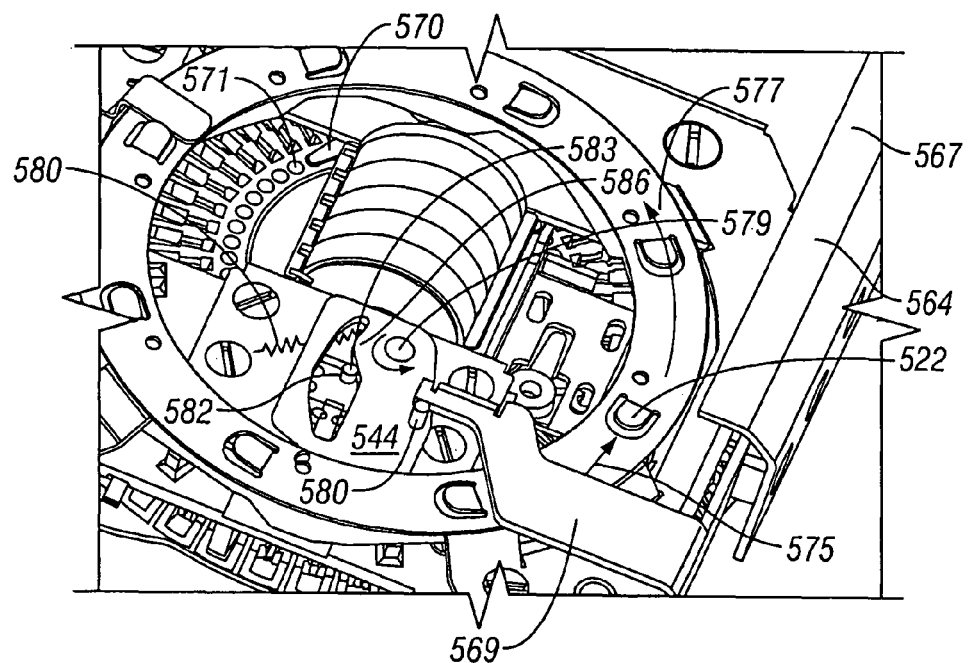

Referring now to FIG. 56C, a still further view of the slider 564 and arm 569 is shown. The arm 569 moves to engage portion 522 as indicated by arrow 575 and this causes the cam 550 to rotate as indicated by arrow 577. In this particular embodiment, the cam 550 rotates about ⅛ of an rotation with each pull of the slider 564. When the slider 564 is return to its home or start position, the arm 569 rides over the portion 522. The movement of the slider also allows the cam surface 544 to rotate about pivot point 579. A resilient member 580 may be coupled to the cam surface 544 to cause it to rotate counterclockwise when the arm 569 moves in the direction of arrow 567. The pin 580 will remain in contact with the arm 569. As the cam surface 544 rotates a first surface 582 will contact the pin 583 on the gripper block 584 and pull the pin 583 back to park a penetrating member into a coupling or narrowed portion 542 of the cartridge 500 as seen in FIG. 55A. As the arm 569 is brought back to the home position, the cam surface 544 rotates back and a second surface 586 that rotates clockwise and pushes the penetrating member forward to be released from the narrowed portion 542 resulting in a position as seen in FIG. 55B. It should be understood that in some embodiments, the release and/or parking of lancet from portion 542 may be powered by the driver 588 without using the mechanical assistance from cam surface 544.

Figure 56D:
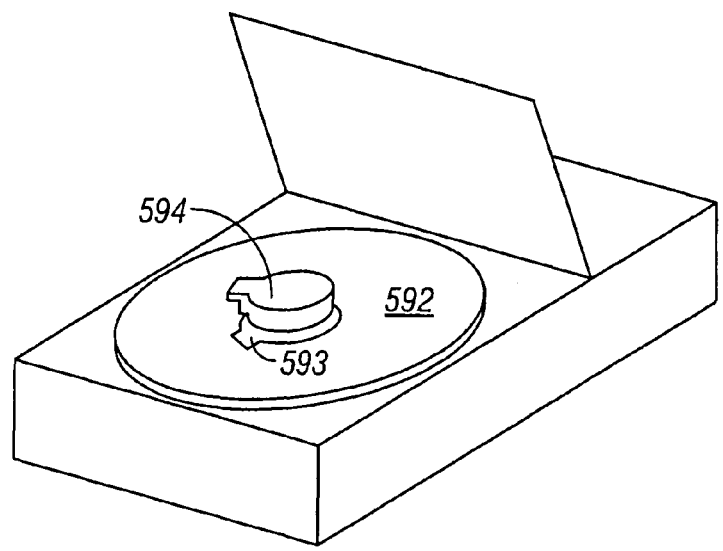

In another embodiment of the cartridge device, a mechanical feature may be included on the cartridge so that there is only one way to load it into the apparatus. For example, in one embodiment holding 50 penetrating members, the cartridge may have 51 pockets or cavities. The 51$^{st}$ pocket will go into the firing position when the device is loaded, thus providing a location for the gripper to rest in the cartridge without releasing a penetrating member from a sterile environment. The gripper 530 in that zeroth position is inside the pocket or cavity and that is the reason why one of the pockets may be empty. Of course, some embodiments may have the gripper 530 positioned to grip a penetrating member as the cartridge 500 is loaded into the device, with the patient lancing themselves soon afterwards so that the penetrating member is not contaminated due to prolonged exposure outside the sterile enclosure. That zeroth position may be the start and finish position. The cartridge may also be notched to engaged a protrusion on the apparatus, thus also providing a method for allowing the penetrating member to loaded or unloaded only in one orientation. Essentially, the cartridge 500 may be keyed or slotted in association with the apparatus so that the cartridge 500 can only be inserted or removed at one orientation. For example as seen in FIG. 56D, the cartridge 592 may have a keyed slot 593 that matches the outline of a protrusion 594 such that the cartridge 592 may only be removed upon alignment of the slot 593 and protrusion 594 upon at the start or end positions. It should be understood that other keyed technology may be used and the slot or key may be located on an outer periphery or other location on the cartridge 592 in manner useful for allowing insertion or removal of the cartridge from only one or a select number of orientations.

Figure 57:
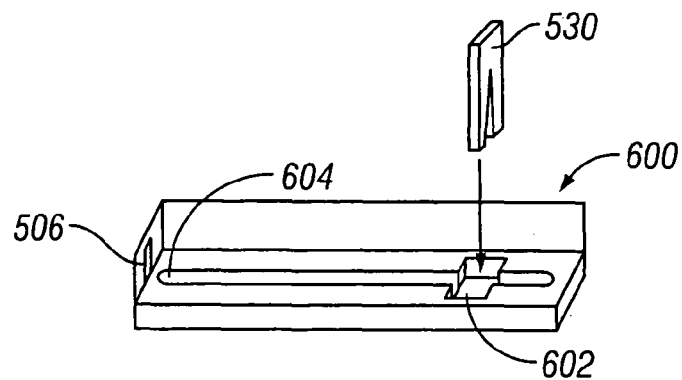
FIGS. 57-65B show optional embodiments according to the present invention.

Referring now to FIG. 57, a cross-section of another embodiment of a cavity 600 housing a penetrating member is shown. The cavity 600 may include a depression 602 for allowing the gripper 530 to penetrate sufficiently deeply into the cavity to frictionally engage the penetrating member 541. The penetrating member may also be housed in a groove 604 that holds the penetrating member in place prior to and after actuation. The penetrating member 541 is lifted upward to clear the groove 604 during actuation and exits through opening 506.

Figure 58:
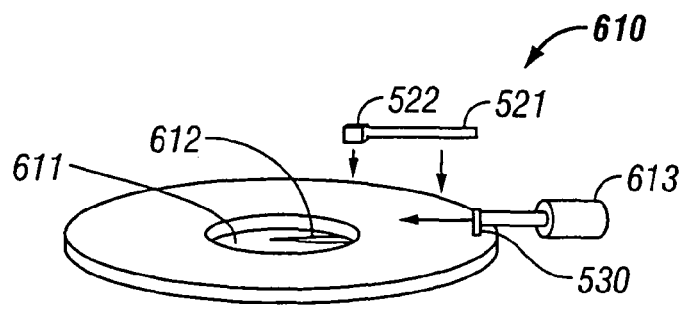

Referring now to FIG. 58, another variation on the system according to the present invention will now be described. FIG. 58 shows a lancing system 610 wherein the penetrating members have their sharpened tip pointed radially inward. The finger or other tissue of the patient is inserted through the center hole 611 to be pierced by the member 612. The penetrating member gripper 530 coupled to drive force generator 613 operate in substantially the same manner as described in FIGS. 54A-G. The punch portions 521 and 522 operate in substantially the same manner to release the penetrating members from the sterile enclosures. The punch portion 522 may be placed on the inner periphery of the device, where the penetrating member exit is now located, so that sterile enclosure material is cleared out of the path of the penetrating member exit.

Figure 59:
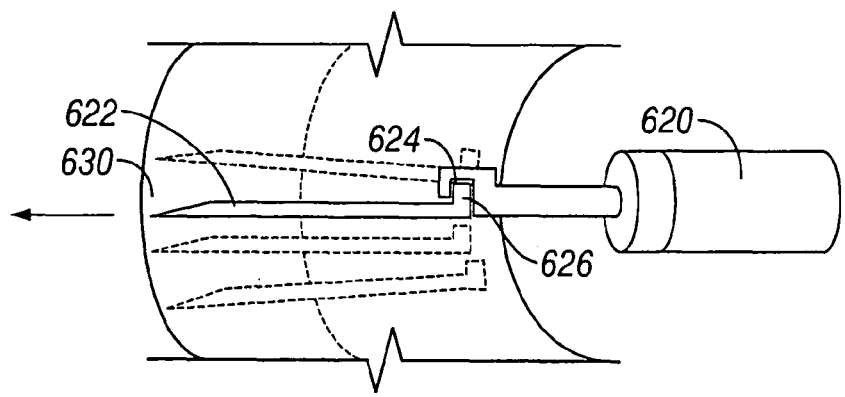

Referring now to FIG. 59, a still further variation on the lancing system according to the present invention will now be described. In the embodiments shown in FIGS. 53-54, the penetrating member gripper 530 approaches the penetrating member from above and at least a portion of the drive system is located in a different plane from that of the cartridge 500. FIG. 59 shows an embodiment where the penetrating member driver 620 is in substantially the same plane as the penetrating member 622. The coupler 624 engages a bent or L shaped portion 626 of the member 622. The cartridge 628 can rotate to engage a new penetrating member with the coupler 624 without having to move the cartridge or coupler vertically. The next penetrating member rotates into position in the slot provided by the coupler 624. A narrowed portion of the cartridge acts as a penetrating member guide 630 near the distal end of the penetrating member to align the penetrating member as it exits the cartridge.

Figure 60A:
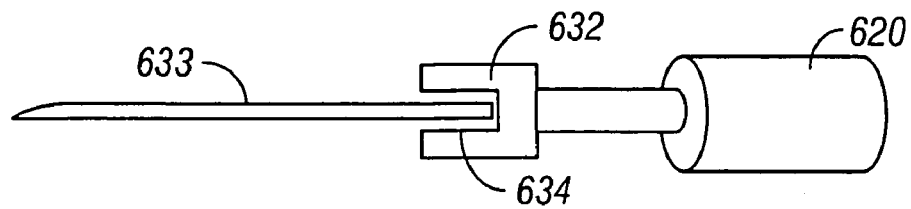
Figure 60B:
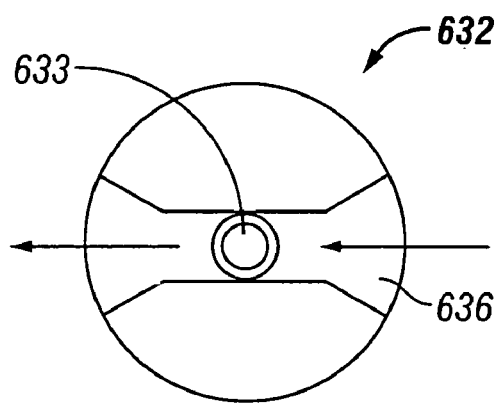
Figure 60C:
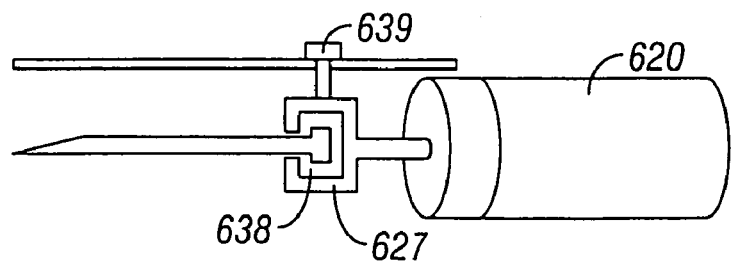

The coupler 624 may come in a variety of configurations. For example, FIG. 60A shows a coupler 632 which can engage a penetrating member 633 that does not have a bent or L-shaped portion. A radial cartridge carrying such a penetrating member 633 may rotate to slide penetrating member into the groove 634 of the coupler 632. FIG. 60B is a front view showing that the coupler 632 may include a tapered portion 636 to guide the penetrating member 633 into the slot 634. FIG. 60C shows an embodiment of the driver 620 using a coupler 637 having a slot 638 for receiving a T-shaped penetrating member. The coupler 637 may further include a protrusion 639 that may be guided in an overhead slot to maintain alignment of the drive shaft during actuation.

Figure 61:
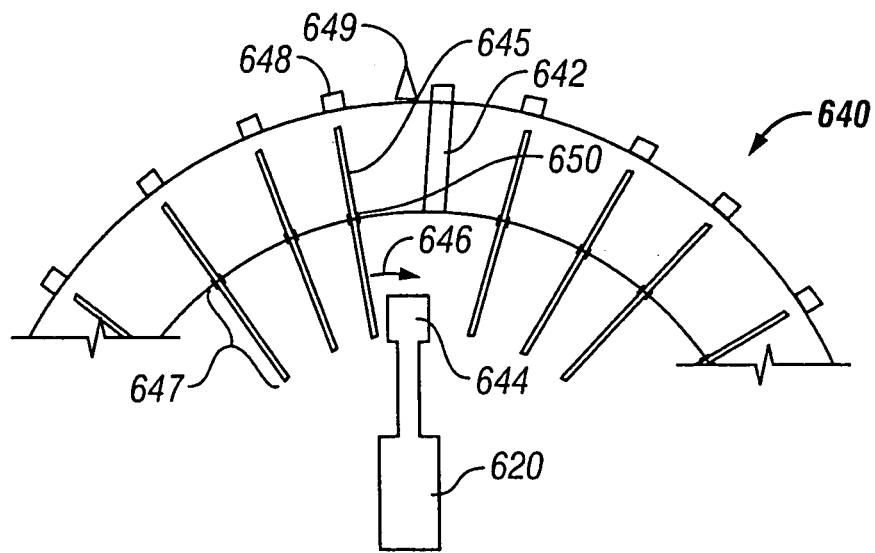

Referring now to FIG. 61, a cartridge 640 for use with an in-plane driver 620 is shown. The cartridge 640 includes an empty slot 642 that allows the cartridge to be placed in position with the driver 620. In this embodiment, the empty slot 642 allows the coupler 644 to be positioned to engage an unused penetrating member 645 that may be rotated into position as shown by arrow 646. As seen in FIG. 61, the cartridge 640 may also be designed so that only the portion of the penetrating member that needs to remain sterile (i.e. the portions that may actually be penetrating into tissue) are enclosed. As seen in FIG. 61, a proximal portion 647 of the penetrating member is exposed. This exposed proximal portion may be about 70% of the penetrating member. In other embodiments it may be between about 69% to about 5% of the penetrating member. The cartridge 640 may further include, but not necessarily, sealing protrusions 648. These protrusions 648 are releasably coupled to the cartridge 640 and are removed from the cartridge 640 by remover 649 as the cartridge rotates to place penetrating member 645 into the position of the active penetrating member. The sterile environment is broken prior to actuation of the member 645 and the member does not penetrate sterile enclosure material that may dull the tip of the penetrating member during actuation. A fracturable seal material 650 may be applied to the member to seal against an inner peripheral portion of the cartridge.

Figure 62:
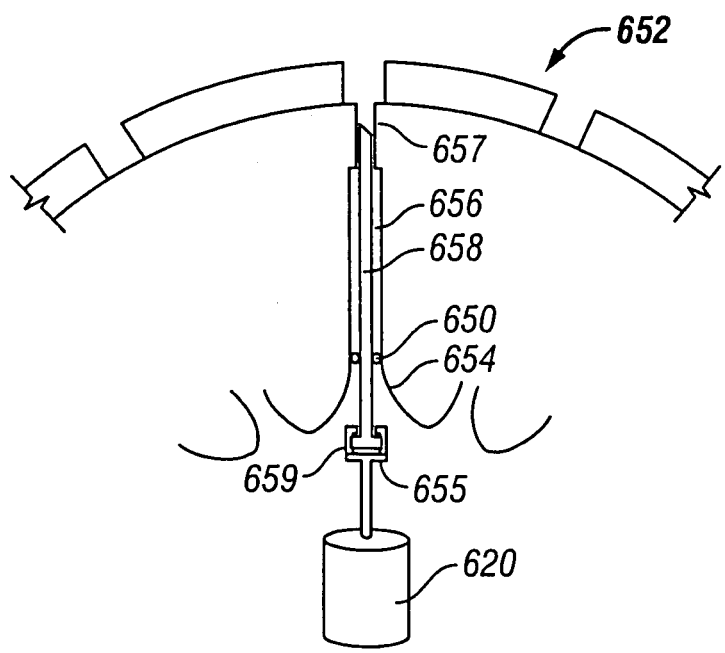

Referring now to FIG. 62, a still further embodiment of a cartridge for use with the present invention will be described. This cartridge 652 includes a tapered portion 654 for allowing the coupler 655 to enter the cavity 656. A narrowed portion 657 guides the penetrating member 658. The coupler 655 may have, but does not necessarily have, movable jaws 659 that engage to grip the penetrating member 658. Allowing the coupler to enter the cavity 656 allows the alignment of the penetrating member to be better maintained during actuation. This tapered portion 654 may be adapted for use with any embodiment of the cartridge disclosed herein.

Figure 63:
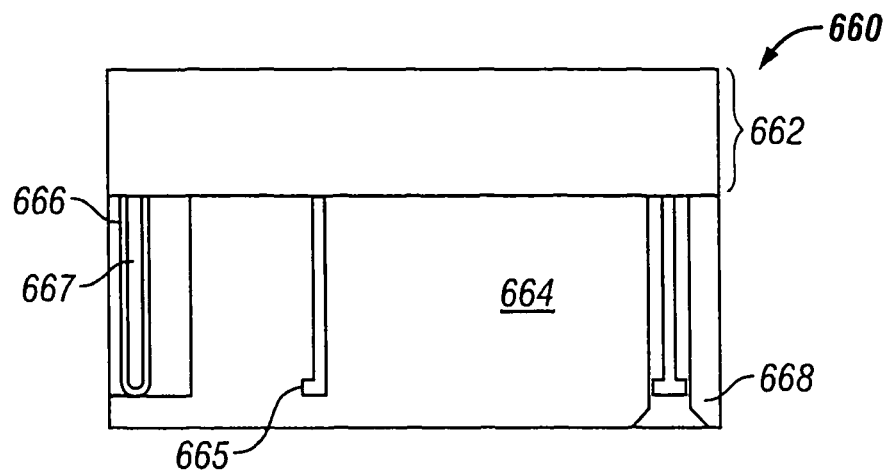

Referring now to FIG. 63, a linear cartridge 660 for use with the present invention will be described. Although the present invention has been shown in use with radial cartridges, the lancing system may be adapted for use with cartridges of other shapes. FIGS. 79-83 show other cartridges of varying shapes adaptable for use with the present invention. FIG. 63 illustrates a cartridge 660 with only a portion 662 providing sterile protection for the penetrating members. The cartridge 660, however, provides a base 664 on which a penetrating member 665 can rest. This provides a level of protection of the penetrating member during handling. The base 664 may also be shaped to provide slots 666 in which a penetrating member 667 may be held. The slot 666 may also be adapted to have a tapered portion 668. These configurations may be adapted for use with any of the embodiments disclosed herein, such as the cartridge 652.

Figure 64A:
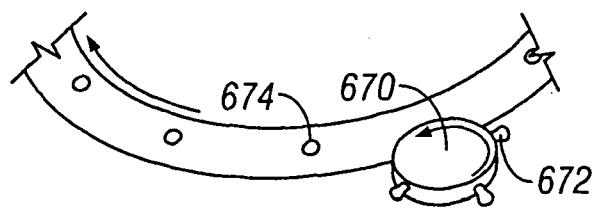
Figure 64B:
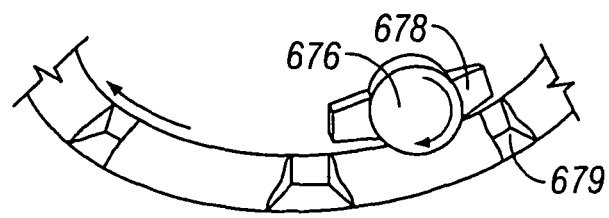
Figure 64C:
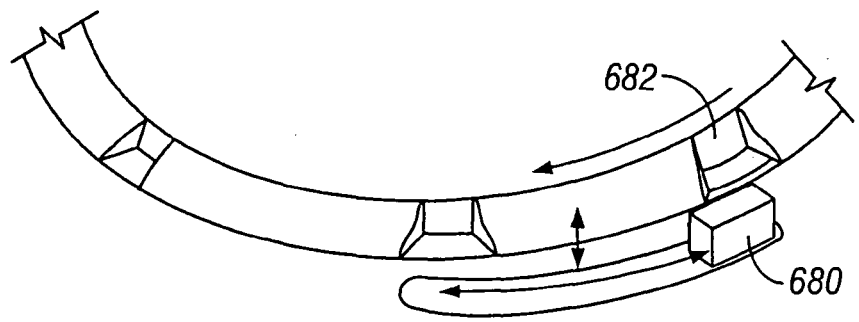

Referring now to FIGS. 64A-64C, a variety of different devices are shown for releasing the sterility seal covering a lateral opening 503 on the cartridge 500. FIG. 64A shows a rotating punch device 670 that has protrusions 672 that punch out the sterility barrier creating openings 674 from which a penetrating member can exit without touching the sterility barrier material. FIG. 64B shows a vertically rotating device 676 with shaped protrusions 678 that punch down the sterility barrier 679 as it is rotated to be in the active, firing position. FIG. 64C shows a punch 680 which is positioned to punch out barrier 682 when the cartridge is lowered onto the punch. The cartridge is rotated and the punch 680 rotates with the cartridge. After the cartridge is rotated to the proper position and lifted up, the punch 680 is spring loaded or otherwise configured to return to the position to engage the sterility barrier covering the next unused penetrating member.

Figure 65A:
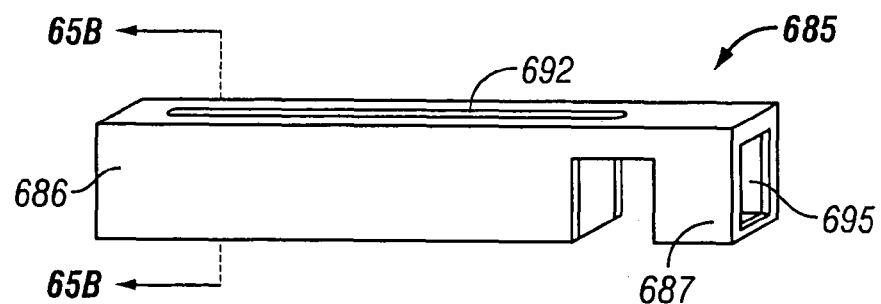
Figure 65B:
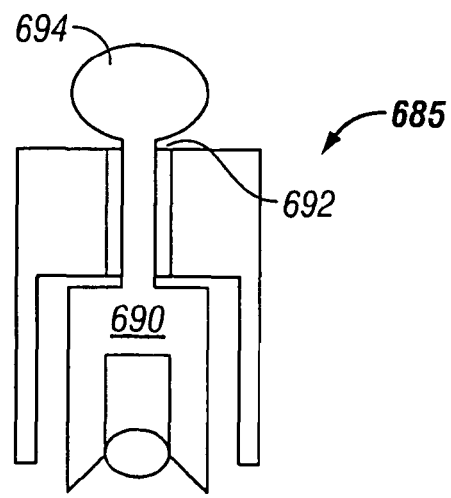

Referring now to FIGS. 65A-65B, another type of punch mechanism for use with a punch plate 520 will now be described. The device shown in FIGS. 53-54 shows a mechanism that first punches and then rotates or indexes the released penetrating member into position. In this present embodiment, the cartridge is rotated first and then the gripper and punch may move down simultaneously. FIG. 65A shows a punch 685 having a first portion 686 and a second portion 687. As seen in cross-sectional view of FIG. 65B, the penetrating member gripper 690 is located inside the punch 685. Thus the penetrating of the sterility barrier is integrated into the step of engaging the penetrating member with the gripper 690. The punch 685 may include a slot 692 allowing a portion 694 of the gripper 690 to extend upward. A lateral opening 695 is provided from which a penetrating member may exit. In some embodiments, the punch portion 687 is not included with punch 686, instead relying on some other mechanism such as those shown in FIGS. 64A-64C to press down on barrier material covering a lateral opening 503.

Referring now to FIG. 66, a still further embodiment of a cartridge according to the present invention will be described.

Figure 67:
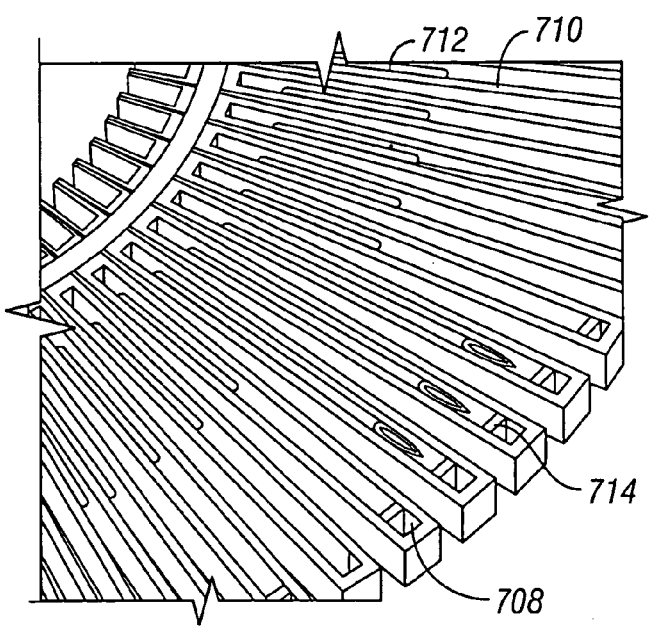
Figure 68:
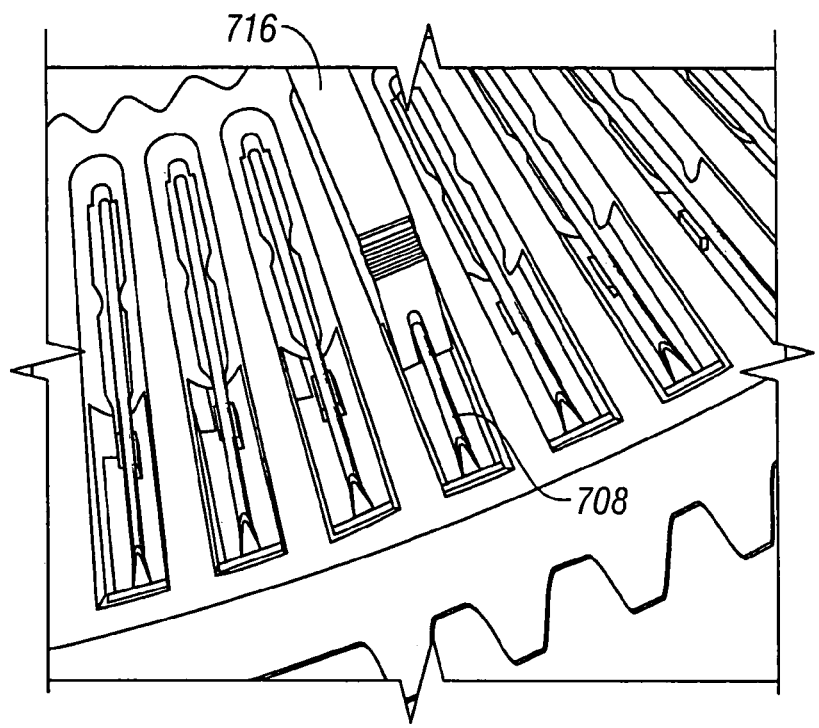

FIG. 66 shows a cartridge 700 with a plurality of cavities 702 and individual deflectable portions or fingers 704. The ends of the protective cavities 702 may be divided into individual fingers (such as one for each cavity) on the outer periphery of the disc. Each finger 704 may be individually sealed with a foil cover (not shown for ease of illustration) to maintain sterility until the time of use. Along the inner periphery of the cartridge 700 are raised step portions 706 to create a ratchet type mechanism. As seen in FIG. 67, a penetrating member 708 may be housed in each cavity. The penetrating member may rest on a raised portion 710. A narrowed portion 712 pinches the proximal portions of the penetration member 708. Each cavity may include a wall portion 714 into which the penetrating member 708 may be driven after the penetrating member has been used. FIG. 68 shows the penetrating member gripper 716 lowered to engage a penetrating member 708. For ease of illustration, a sterility barrier covering each of the cavities is not shown.

Figure 69A:
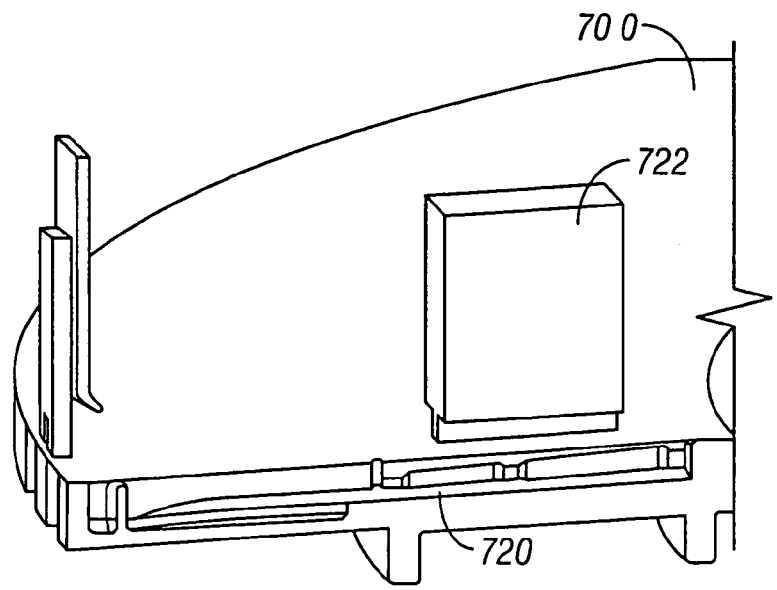
FIGS. 69A-69L show the sequence of motions associated with an optional embodiment of a cartridge according to the present invention.

Referring now to FIGS. 69A-69L, the sequence of steps for actuating a penetrating member in a cartridge 700 will be described. It should be understood that in other embodiments, steps may be combined or reduced without departing from the sprit of the present invention. The last penetrating member to be used may be left in a retracted position, captured by a gripper 716. The end of the protective cavity 704 may be deflected downward by the previous actuation. The user may operate a mechanism such as but not limited to a thumbwheel, lever, crank, slider, etc. . . . that advances a new penetrating member 720 into launch position as seen in FIG. 69A. The mechanism lifts a bar that allows the protective cavity to return to its original position in the plane of the disc.

Figure 69B:
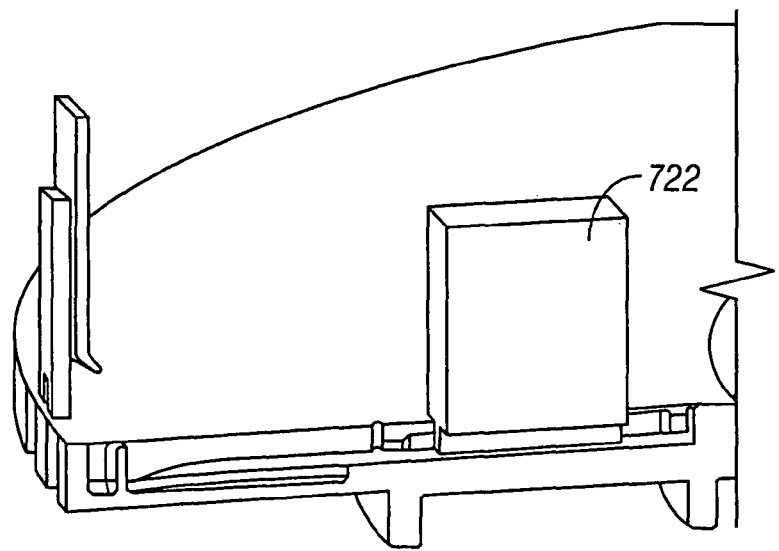

In this embodiment as shown in FIG. 69B, the penetrating member guide 722 presses through foil in rear of pocket to "home" penetrating member and control vertical clearance. For ease of illustration, actuation devices for moving the penetrating member guide 722 and other mechanisms are not shown. They may be springs, cams, or other devices that can lower and move the components shown in these figures. In some embodiments, the cartridge 700 may be raised or lowered to engage the penetrating member guide 722 and other devices.

Figure 69C:
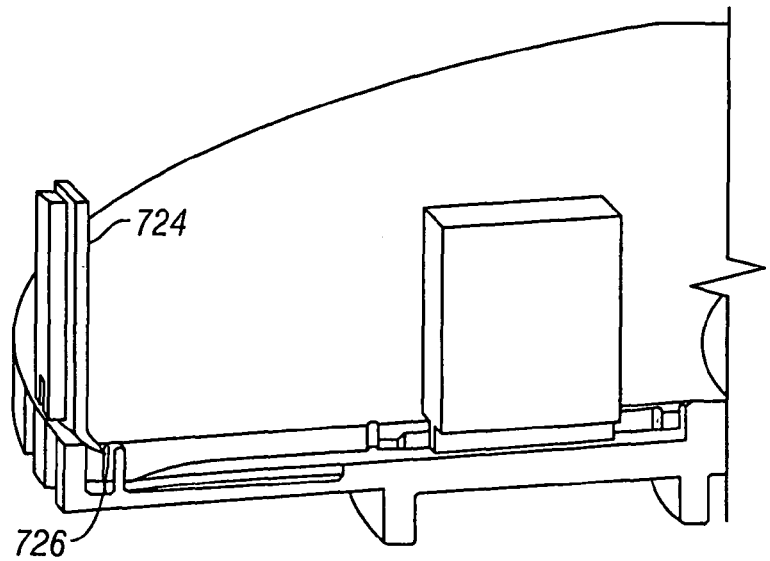

As seen in FIG. 69C, the plough or sterile enclosure release device 724 is lowered to engage the cartridge 700. In some embodiments, the disc or cartridge 700 may raised part way upward until a plough or plow blade 724 pierces the sterility barrier 726 which may be a foil covering.

Figure 69D:
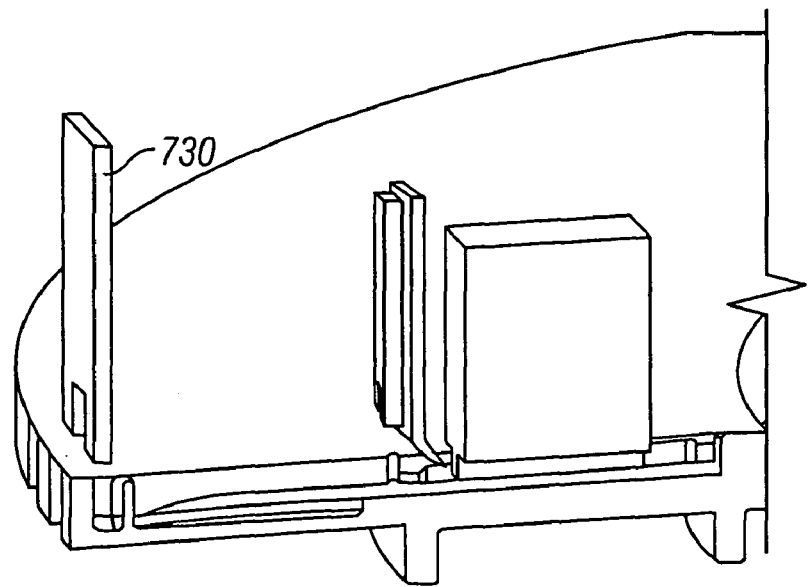

Referring now to FIG. 69D, the plough 724 clears foil from front of pocket and leaves it attached to cartridge 700. The plough 724 is driven radially inward, cutting open the sterility barrier and rolling the scrap into a coil ahead of the plough. Foil naturally curls over and forms tight coil when plough lead angle is around 55 degs to horizontal. If angle of the plough may be between about 60-40 degs, preferably closer to 55 degs. In some embodiments, the foil may be removed in such a manner that the penetrating member does not need to pierce any sterile enclosure materials during launch.

Figure 69E:
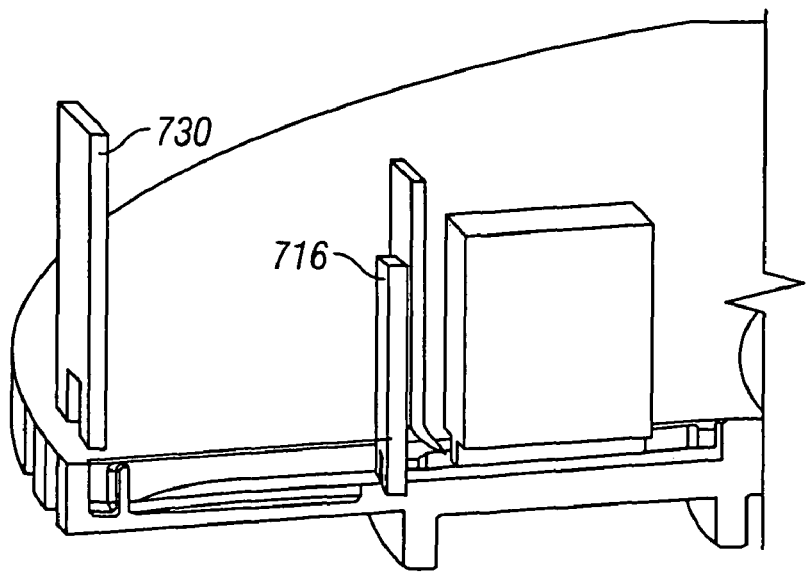

Referring now to FIG. 69E, the gripper 716 may be lowered to engage the bare penetrating member or piercing member 720. Optionally, the disc or cartridge 8000 may be raised until the penetrating member 720 is pressed firmly into the gripper 716. Although not shown in the present figure, the penetrating member driver or actuator of the present embodiment may remain in the same horizontal plane as the penetrating member.

Figure 69F:
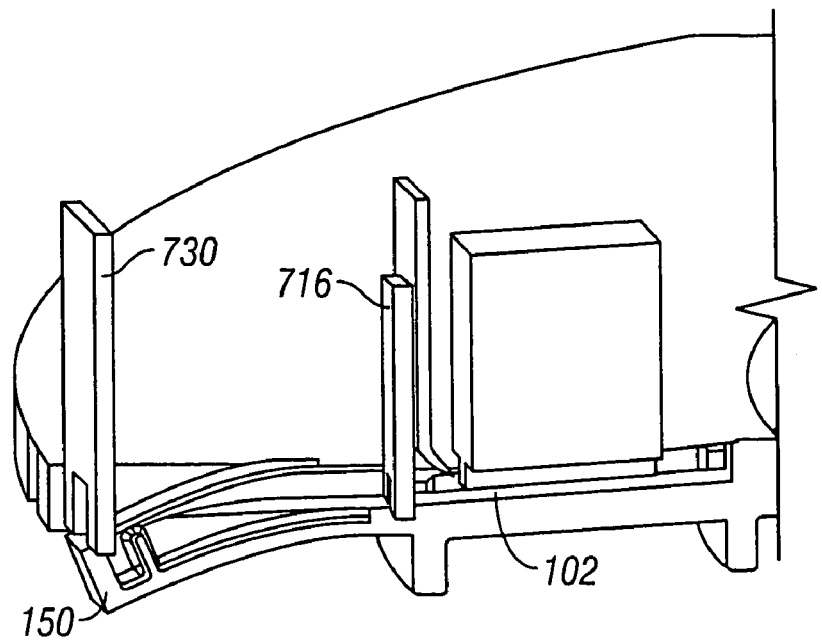

As seen in FIG. 69F, a bar 730 may be pressed downward on the outer end 732 of the protective cavity to deflect it so it is clear of the path of the penetrating member. In the present embodiment, the bar 730 is shaped to allow the bare penetrating member 720 to pass through. It should be understood that other shapes and orientations of the bar (such as contacting only one side or part of end 732) may be used to engage the end 732.

Figure 69G:
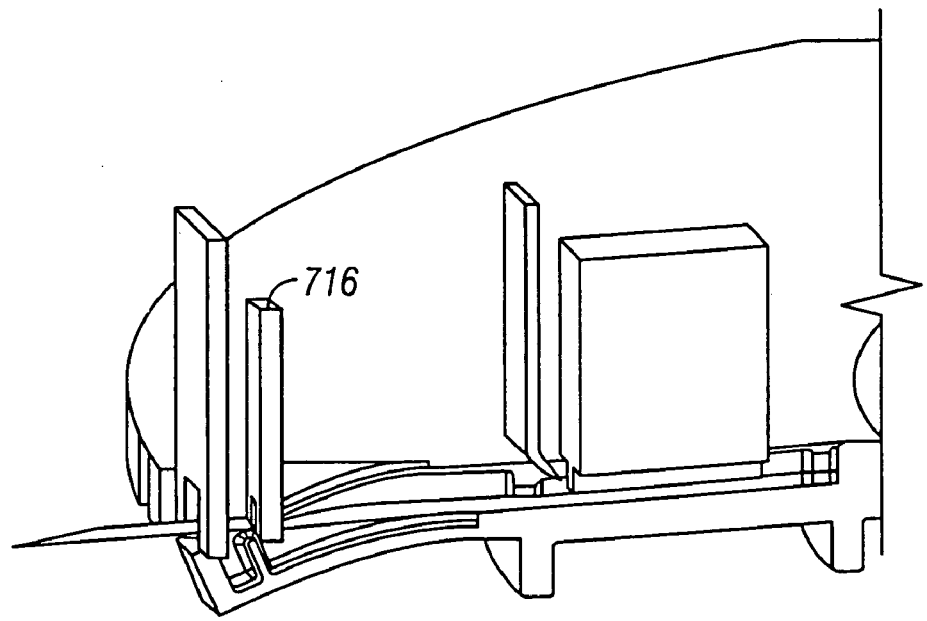

Referring now to FIG. 69G, an electrical solenoid or other electronic or feedback controllable drive may actuate the gripper 716 radially outward, carrying the bare penetrating member 720 with it. The bare penetrating member projects from the protective case and into the skin of a finger or other tissue site that has been placed over the aperture of the actuator assembly. Suitable penetrating member drivers are described in commonly assigned, copending U.S. patent application Ser. No. 10/127,395 filed Apr. 19, 2002.

Figure 69H:
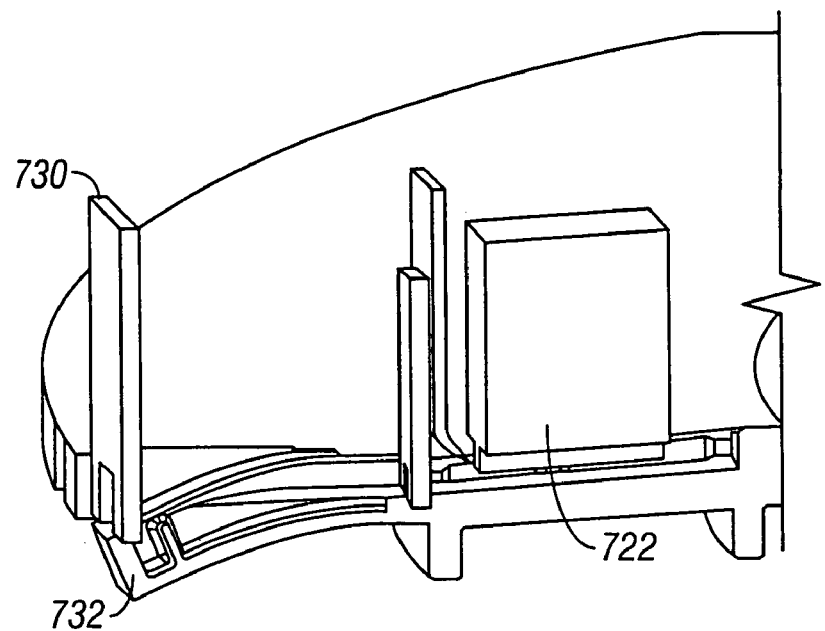

Referring now to FIG. 69H, the solenoid or other suitable penetrating member driver retracts the bare penetrating member 720 into a retracted position where it parks until the beginning of the next lancing cycle.

Figure 69I:
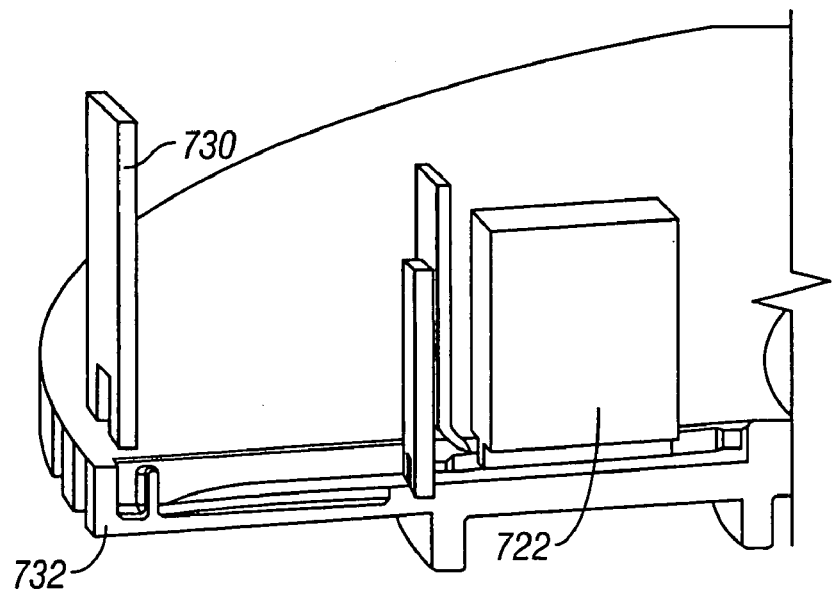

Referring now to FIG. 69I, bar 730 may be released so that the end 150 returns to an in-plane configuration with the cartridge 800.

Figure 69J:
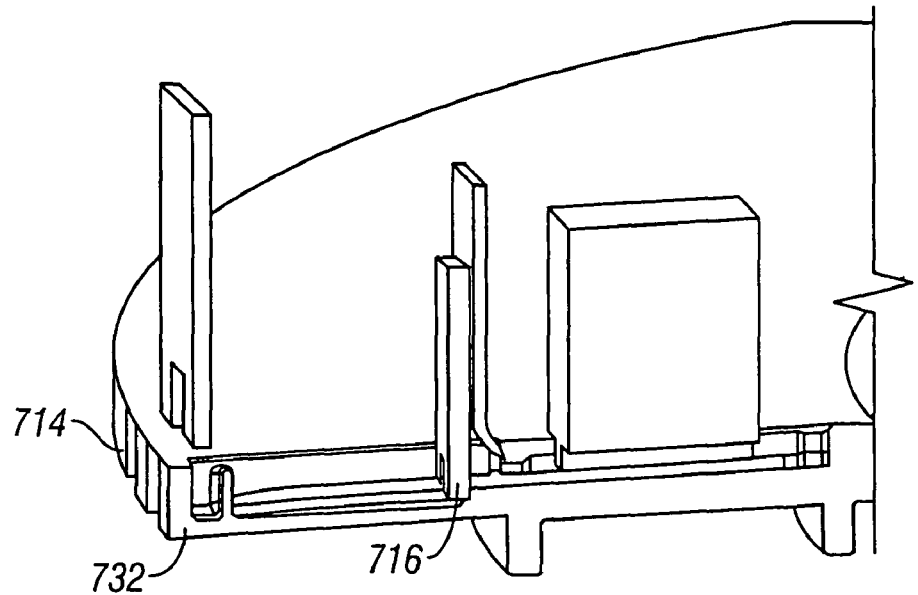

As seen in FIG. 69J, the gripper 716 may drive a used bare penetrating member radially outward until the sharpened tip is embedded into a plastic wall 714 at or near the outward end 732 of the cavity thus immobilizing the contaminated penetrating member.

Figure 69K:
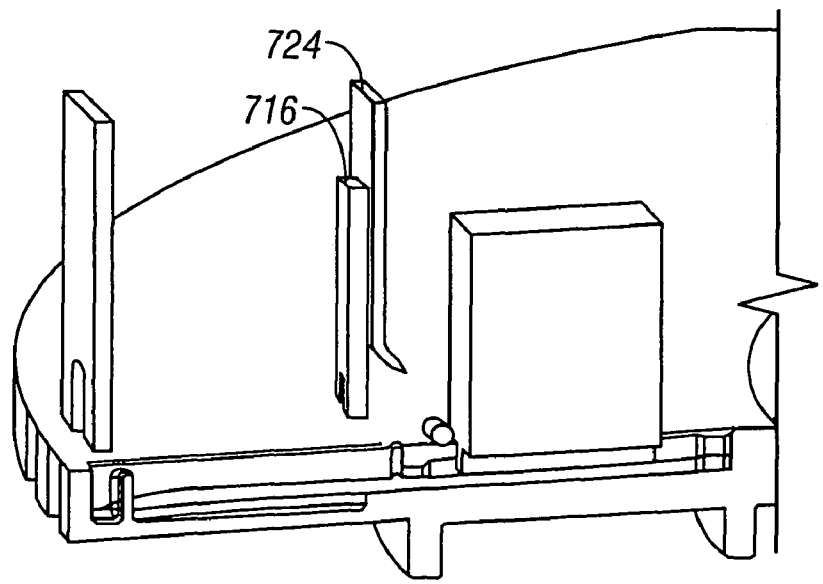
Figure 69L:
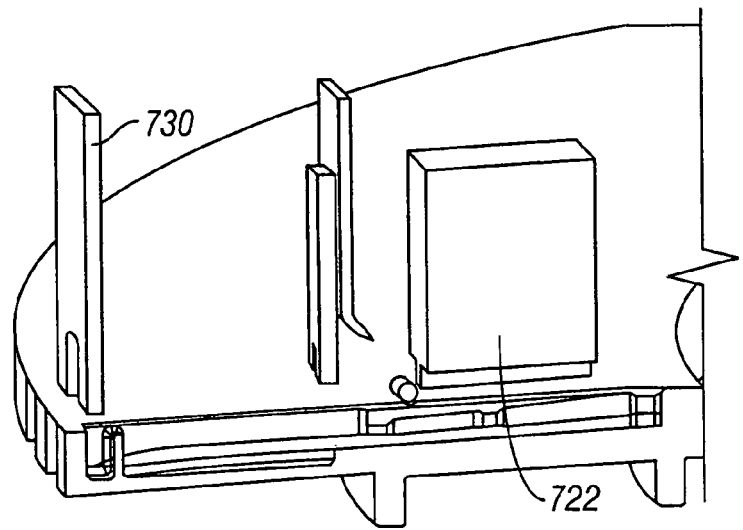

As seen in FIGS. 69K and 69L, the plough 724, the gripper 716, and penetrating member guide 722 may all be disengaged from the bare penetrating member 720. Optionally, it should be understood that the advance mechanism may lower the cartridge 700 from the gripper 716. The used penetrating member, restrained by the tip embedded in plastic, and by the cover foil at the opposite end, is stripped from the gripper. The disc or cartridge 700 may be rotated until a new, sealed; sterile penetrating member is in position under the launch mechanism.

Figure 70:
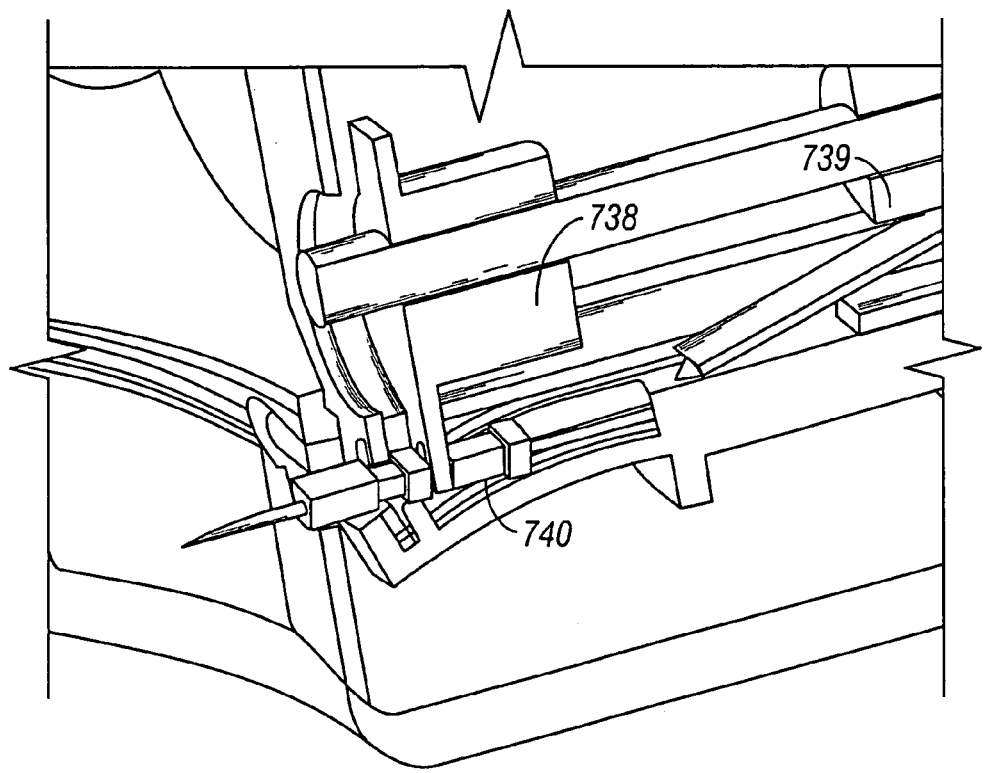
FIGS. 70-72 show views of a sample modules used with still further embodiments of a cartridge according to the present invention.
Figure 71:
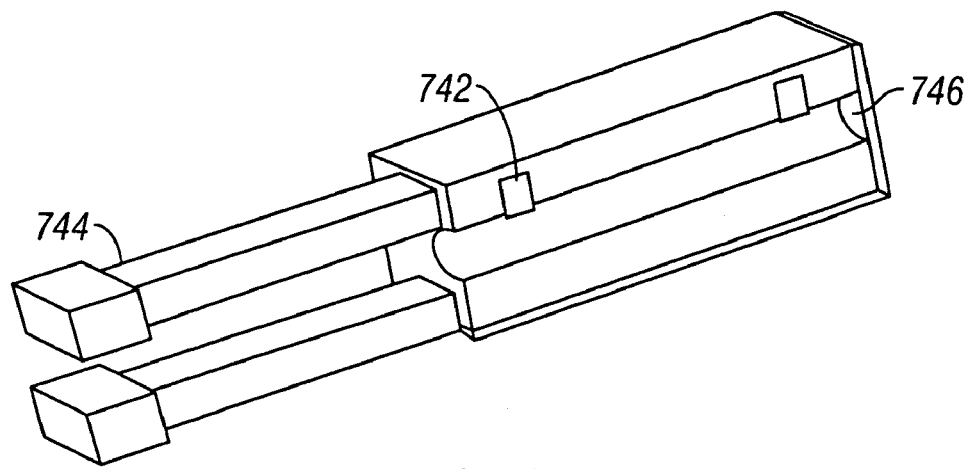

Referring now to FIGS. 70 and 71, one object for some embodiments of the invention is to include blood sampling and sensing on this penetrating member actuation device. In the present embodiment, the drive mechanism (gripper 738 and solenoid drive coil 739) may be used to drive a penetrating member into the skin and couple this lancing event to acquire the blood sample as it forms at the surface of the finger. In a first embodiment shown in FIG. 70, microfluidic module 740 bearing the analyte sensor chemistry and detection device 742 (FIG. 71) is couple on to the shaft of the penetrating member 720. The drive cycle described above may also actuate the module 740 so that it rests at the surface of the finger to acquire blood once the penetrating member retracts from the wound. The module 740 is allowed to remain on the surface of the finger or other tissue site until the gripper 738 has reached the back end 744 of the microfluidics module 740, at which point the module is also retracted into the casing. The amount of time the module 740 remains on the finger, in this embodiment, may be varied based on the distance the end 744 is located and the amount of time it takes the gripper to engage it on the withdrawal stroke. The blood filled module 740, filled while the module remains on pierced tissue site, may then undergo analyte detection by means such as optical or electrochemical sensing.

The blood may be filled in the lumen that the penetrating member was in or the module may have separately defined sample chambers to the side of the penetrating member lumen. The sensor may also be placed right at the immediate vicinity or slightly setback from the module opening receiving blood so that low blood volumes will still reach the sensor. In some embodiments, the analyte sensing device and a visual display or other interface may be on board the apparatus and thus provide a readout of analyte levels without need to plug apparatus or a test strip into a separate reader device. As seen in FIG. 71, the cover 746 may also be clear to allow for light to pass through for optical sensing. The sensor may be used with low volumes such as less than about 1 microliter of sample, preferably less than about 0.6 microliter, more preferably less than about 0.3 microliter, and most preferably less than about 0.1 microliter of sample.

Figure 72:
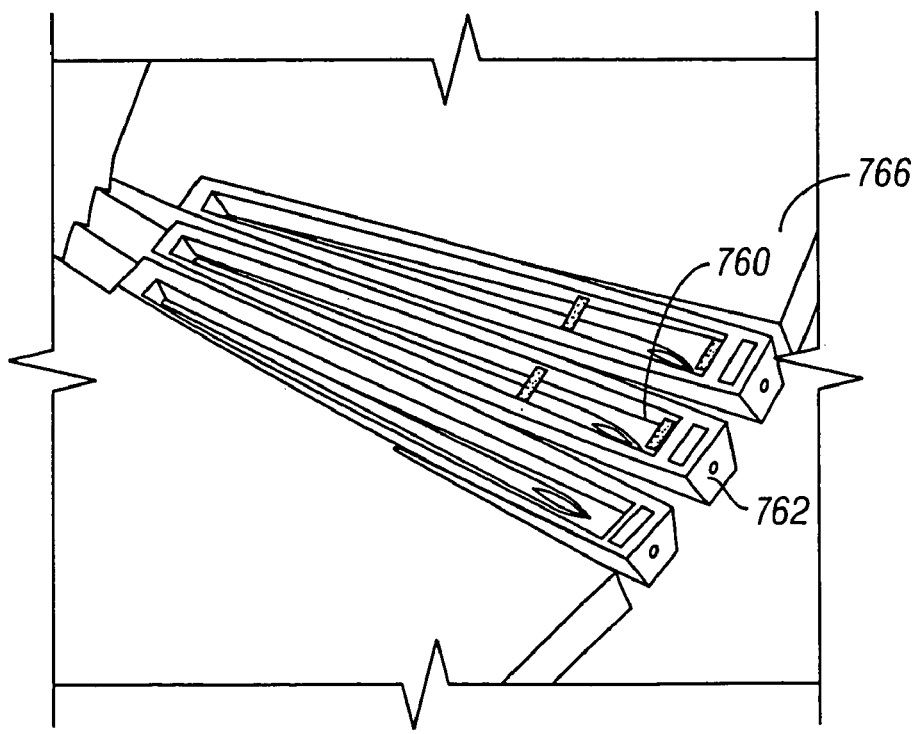

In another embodiment as seen in FIG. 72, sensing elements 760 may be directly printed or formed on the top of bottom of the penetrating member cartridge 700, depending on orientation. The bare penetrating member 720 is then actuated through a hole 762 in the plastic facing, withdrawn into the radial cavity followed by the blood sample. Electrochemical or optical detection for analyte sensing may then be carried out (FIG. 72). Again the cavity 766 may have a clear portion to allow light to pass for optical sensing. In one embodiment, a multiplicity of miniaturized sensor fields may be placed on the floor of the radial cavity as shown in FIG. 72 or on the microfluidic module shown in FIG. 71 to allow many tests on a single analyte form a single drop of blood to improve accuracy and precision of measurement. Although not limited in this manner, additional sensor fields or regions may also be included for calibration or other purposes.

Figure 73:
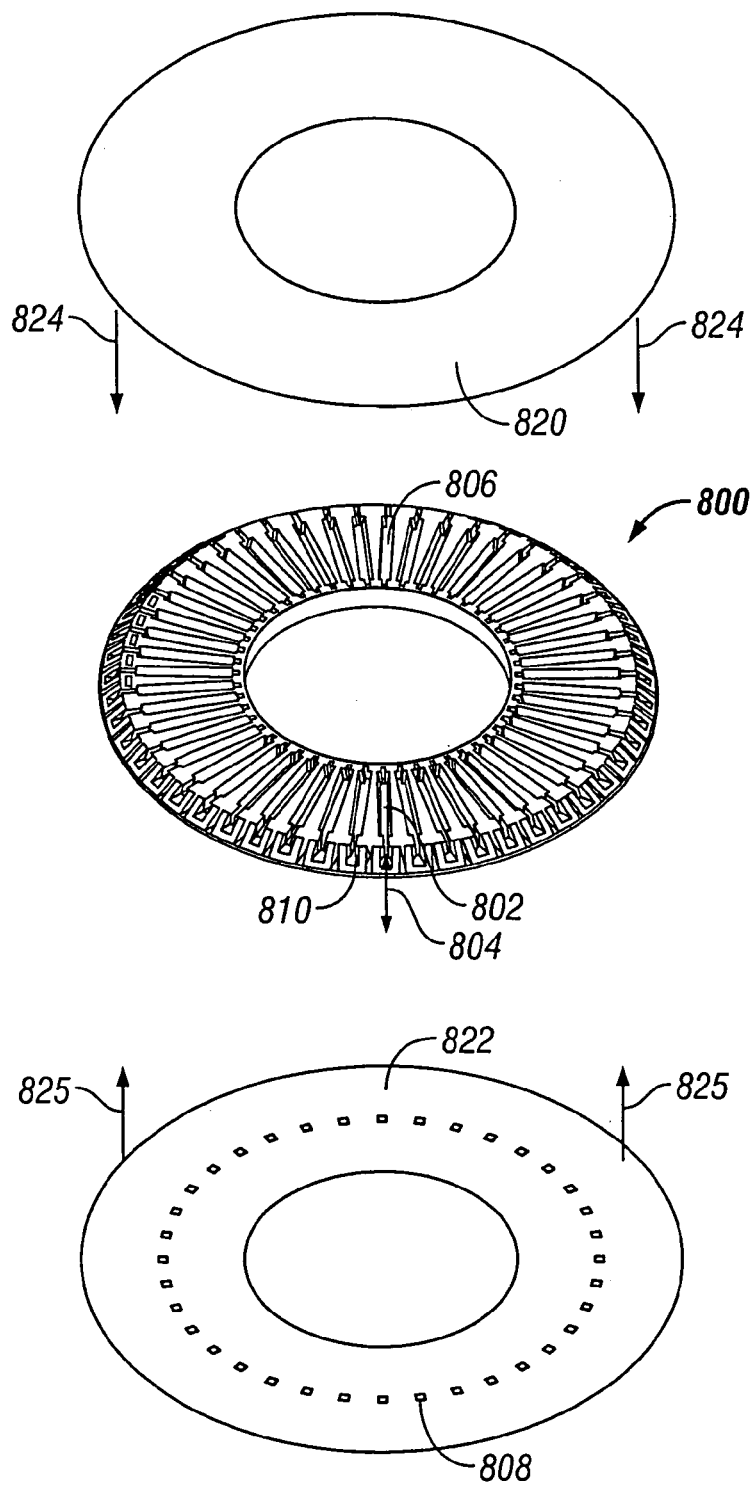
FIG. 73 shows a cartridge with a sterility barrier and a sensor layer.

Referring now to FIG. 73, a still further embodiment of a cartridge according to the present invention will be described. FIG. 73 shows one embodiment of a cartridge 800 which may be removably inserted into an apparatus for driving penetrating members to pierce skin or other tissue. The cartridge 800 has a plurality of penetrating members 802 that may be individually or otherwise selectively actuated so that the penetrating members 802 may extend outward from the cartridge, as indicated by arrow 804, to penetrate tissue. In the present embodiment, the cartridge 800 may be based on a flat disc with a number of penetrating members such as, but in no way limited to, (25, 50, 75, 100, . . . ) arranged radially on the disc or cartridge 800. It should be understood that although the cartridge 800 is shown as a disc or a disc-shaped housing, other shapes or configurations of the cartridge may also work without departing from the spirit of the present invention of placing a plurality of penetrating members to be engaged by a penetrating member driver.

Figure 75:
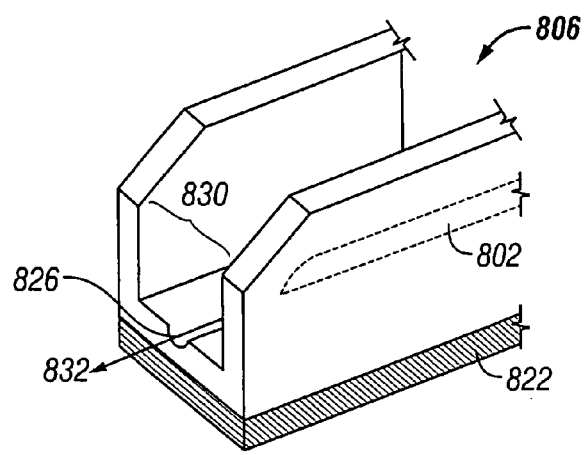

Each penetrating member 802 may be contained in a molded cavity 806 in the cartridge 800 with the penetrating member's sharpened end facing radially outward and may be in the same plane as that of the cartridge. Although not limited in this manner, the ends of the protective cavities 806 may be divided into individual fingers (such as one for each cavity) on the outer periphery of the disc. The particular shape of each cavity 806 may be designed to suit the size or shape of the penetrating member therein or the amount of space desired for placement of the analyte sensors 808. For example and not limitation, the cavity 806 may have a V-shaped cross-section, a U-shaped cross-section, C-shaped cross-section, a multi-level cross section or the other cross-sections. The opening 810 through which a penetrating member 802 may exit to penetrate tissue may also have a variety of shapes, such as but not limited to, a circular opening, a square or rectangular opening, a U-shaped opening, a narrow opening that only allows the penetrating member to pass, an opening with more clearance on the sides, a slit, a configuration as shown in FIG. 75, or the other shapes.

After actuation, the penetrating member 802 is returned into the cartridge and may be held within the cartridge 800 in a manner so that it is not able to be used again. By way of example and not limitation, a used penetrating member may be returned into the cartridge and held by the launcher in position until the next lancing event. At the time of the next lancing, the launcher may disengage the used penetrating member with the cartridge 800 turned or indexed to the next clean penetrating member such that the cavity holding the used penetrating member is position so that it is not accessible to the user (i.e. turn away from a penetrating member exit opening). In some embodiments, the tip of a used penetrating member may be driven into a protective stop that hold the penetrating member in place after use. The cartridge 800 is replaceable with a new cartridge 800 once all the penetrating members have been used or at such other time or condition as deemed desirable by the user.

Referring still to FIG. 73, the cartridge 800 may provide sterile environments for penetrating members via seals, foils, covers, polymeric, or similar materials used to seal the cavities and provide enclosed areas for the penetrating members to rest in. In the present embodiment, a foil or seal layer 820 is applied to one surface of the cartridge 800. The seal layer 820 may be made of a variety of materials such as a metallic foil or other seal materials and may be of a tensile strength and other quality that may provide a sealed, sterile environment until the seal layer 820 is penetrate by a suitable or penetrating device providing a preselected or selected amount of force to open the sealed, sterile environment. Each cavity 806 may be individually sealed with a layer 820 in a manner such that the opening of one cavity does not interfere with the sterility in an adjacent or other cavity in the cartridge 800. As seen in the embodiment of FIG. 73, the seal layer 820 may be a planar material that is adhered to a top surface of the cartridge 800.

Depending on the orientation of the cartridge 800 in the penetrating member driver apparatus, the seal layer 820 may be on the top surface, side surface, bottom surface, or other positioned surface. For ease of illustration and discussion of the embodiment of FIG. 73, the layer 820 is placed on a top surface of the cartridge 800. The cavities 806 holding the penetrating members 802 are sealed on by the foil layer 820 and thus create the sterile environments for the penetrating members. The foil layer 820 may seal a plurality of cavities 806 or only a select number of cavities as desired.

Figure 76:
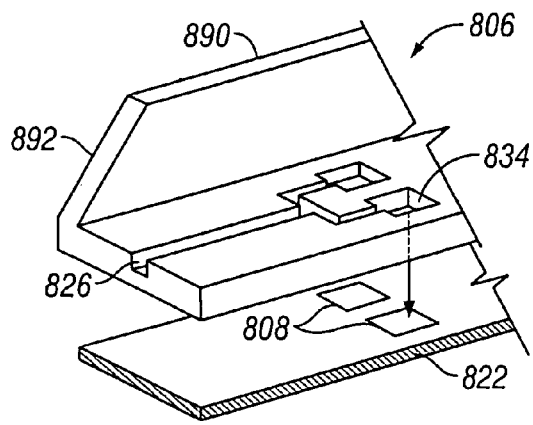

In a still further feature of FIG. 73, the cartridge 800 may optionally include a plurality of analyte sensors 808 on a substrate 822 which may be attached to a bottom surface of the cartridge 800. The substrate may be made of a material such as, but not limited to, a polymer, a foil, or other material suitable for attaching to a cartridge and holding the sensors 808. As seen in FIG. 73, the substrate 822 may hold a plurality of sensors, such as but not limited to, about 10-50, 50-100, or other combinations of sensors. This facilitates the assembly and integration of sensors 808 with cartridge 800. These sensors 808 may enable an integrated body fluid sampling system where the penetrating members 802 create a wound tract in a target tissue, which expresses body fluid that flows into the cartridge for analyte detection by at least one of the sensors 808. The substrate 822 may contain any number of analyte sensors 808 suitable for detecting analytes in cartridge having a plurality of cavities 806. In one embodiment, many analyte sensors 808 may be printed onto a single substrate 822 which is then adhered to the cartridge to facilitate manufacturing and simplify assembly. The sensors 808 may be electrochemical in nature. The sensors 808 may further contain enzymes, dyes, or other detectors which react when exposed to the desired analyte. Additionally, the sensors 808 may comprise of clear optical windows that allow light to pass into the body fluid for analyte analysis. The number, location, and type of sensor 808 may be varied as desired, based in part on the design of the cartridge, number of analytes to be measured, the need for sensor calibration, and the sensitivity of the sensors. If the cartridge 800 uses a sensor arrangement where the sensors are on a substrate attached to the bottom of the cartridge, there may be through holes (as shown in FIG. 76), wicking elements, capillary tube or other devices on the cartridge 800 to allow body fluid to flow from the cartridge to the sensors 808 for analysis. In other configurations, the sensors 808 may be printed, formed, or otherwise located directly in the cavities housing the penetrating members 802 or areas on the cartridge surface that receive blood after lancing.

The use of the seal layer 820 and substrate or sensor layer 822 may facilitate the manufacture of these cartridges 10. For example, a single seal layer 820 may be adhered, attached, or otherwise coupled to the cartridge 800 as indicated by arrows 824 to seal many of the cavities 806 at one time. A sheet 822 of sensors may also be adhered, attached, or otherwise coupled to the cartridge 800 as indicated by arrows 825 to provide many sensors on the cartridge at one time. During manufacturing of one embodiment of the present invention, the cartridge 800 may be loaded with penetrating members 802, sealed with layer 820 and a temporary layer (not shown) on the bottom where substrate 822 would later go, to provide a sealed environment for the penetrating members. This assembly with the temporary bottom layer is then taken to be sterilized. After sterilization, the assembly is taken to a clean room where the temporary bottom layer is removed and the substrate 822 with sensors is coupled to the cartridge as shown in FIG. 73. This process allows for the sterile assembly of the cartridge with the penetrating members 802 using processes and/or temperatures that may degrade the accuracy or functionality of the sensors on substrate 822.

In some embodiments, more than one seal layer 820 may be used to seal the cavities 806. As examples of some embodiments, multiple layers may be placed over each cavity 806, half or some selected portion of the cavities may be sealed with one layer with the other half or selected portion of the cavities sealed with another sheet or layer, different shaped cavities may use different seal layer, or the like. The seal layer 820 may have different physical properties, such as those covering the penetrating members 802 near the end of the cartridge may have a different color such as red to indicate to the user (if visually inspectable) that the user is down to say 10, 5, or other number of penetrating members before the cartridge should be changed out.

Figure 74:
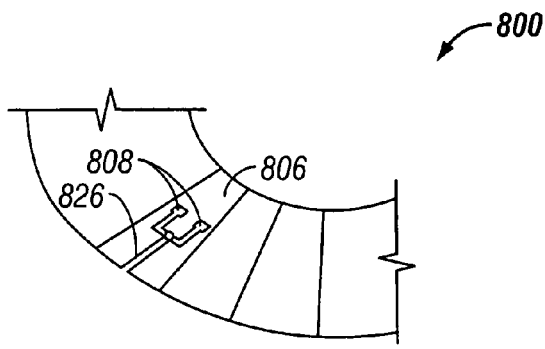
FIGS. 74-78 show still further embodiments of analyte sensors coupled to a cartridge.

Referring now to FIGS. 74 and 75, one embodiment of the microfluidics used with the sensors 808 in cartridge 800 will now be described. For ease of illustration, the shape of cavity 806 has been simplified into a simple wedge shape. It should be understood that more sophisticated configurations such as that shown in FIG. 73 may be used. FIG. 74 shows a channel 826 that assists in drawing body fluid towards the sensors 808. In the present embodiment, two sensors 808 are shown in the cavity 806. This is purely for illustrative purposes as the cavity 806 may have only one sensor or any other number of sensors as desired. Body fluid entering cavity 806, while filling part of the cavity, will also be drawn by capillary action through the groove 826 towards the sensors 808.

FIG. 75 shows a perspective view of a cutout of the cavity 806. The penetrating member 802 (shown in phantom) is housed in the cavity 806 and may extend outward through a penetrating member exit opening 830 as indicated by arrow 832. The position of the tip of penetrating member 802 may vary, such as being near the penetrating member exit port or spaced apart from the exit. The location of the tip relative to the sensor 808 may also be varied, such as being spaced apart or away from the sensor or collocated or in the immediate vicinity of the sensor. Fluid may then enter the cavity 806 and directed by channel 826. The channel 826 as shown in FIG. 75 is a groove that is open on top. The channel 826 may be entirely a groove with an open top or it may have a portion that is has a sealed top forming a lumen, or still further, the groove may be closed except for an opening near the penetrating member exit opening 830. It should be understood that capillary action can be achieved using a groove having one surface uncovered. In some embodiments, the sensor 808 is positioned close to the penetrating member exit opening 830 so that the sensor 808 may not need a capillary groove or channel to draw body fluid, such as in FIG. 78.

As seen in FIGS. 75 and 76, the cavity 806 may include the substrate 822 coupled to its bottom surface containing the sensors 808. With the sensors 808 located on the underside of the cartridge 800 as seen in FIG. 76, the cartridge 800 may include at least one through hole 834 to provide a passage for body fluid to pass from the cavity 806 to the sensor 808. The size, location, shape, and other features of the through hole 834 may be varied based on the cavity 806 and number of sensors 808 to be provided. In other embodiments, wicking elements or the like may be used to draw body fluid from the groove 826 to down to the sensor 808 via the through hole or holes 834.

Figure 77:
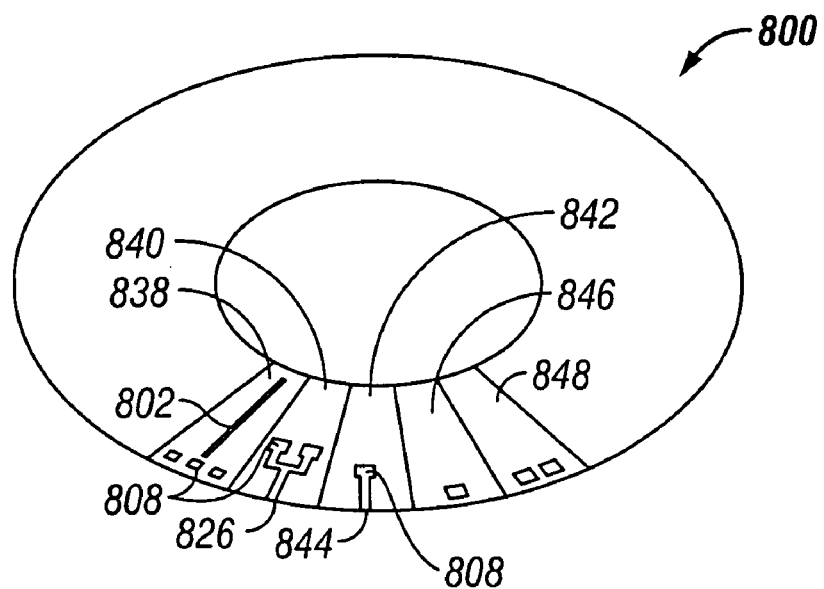

Referring now to FIG. 77, a variety of groove and sensor configurations are shown on a single cartridge. These configurations are shown only for illustrative purposes and a single cartridge may not incorporate each of these configurations. It should be understood, however, that sensor configuration could be customized for each cavity, such as but not limited to, using a different number and location of sensors depending lancing variables associated with that cavity, such as the time of day of the lancing event, the type of analyte to be measured, the test site to be lanced, or other lancing parameter.

FIG. 77 shows a penetrating member 802 in a cavity 838 with three sensors 808 in the cavity. For ease of illustration, the penetrating member 802 is omitted from the remaining cavities so that the sensor configurations can be more easily seen. Cavity 840 has a channel 826 with two sensors 808. Cavity 842 has a channel 844 coupled to a single sensor 808. Cavities 846 and 848 have one and two sensors 808, respectively. The sensors 808 in those cavities may be located directly at the penetrating member exit from the cartridge or substantially at the penetrating member exit. Other sensor configurations are also possible, such as but not limited to, placing one or more sensors on a side wall of the cavity, placing the sensors in particular arrays (for example, a linear array, triangular array, square array, etc. . . . ) on the side wall or bottom surface, using mixed types of sensors (for example, electrochemical and optical, or some other combination), or mixed positioning of sensors (for example, at least one sensor on the substrate below the cartridge and at least one sensor in the cavity).

Figure 78:
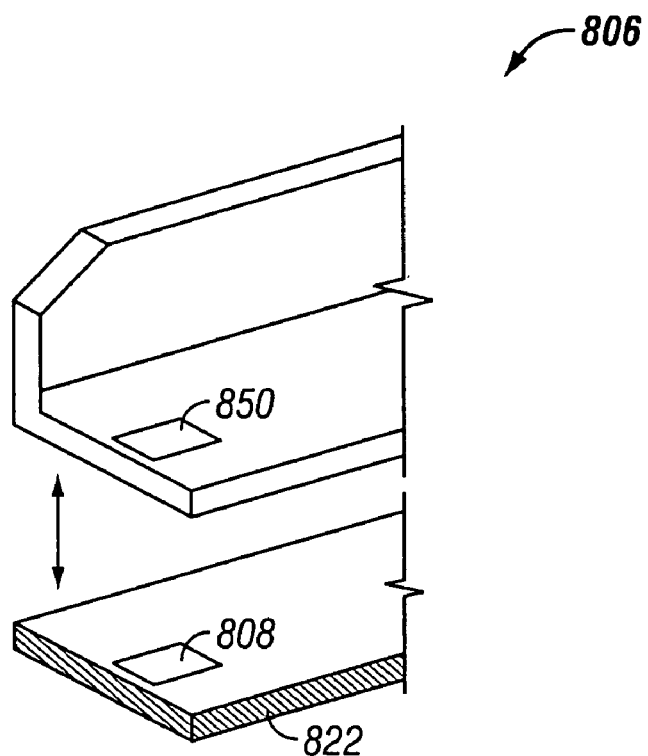

FIG. 78 shows an embodiment of cartridge 800 where the sensor 850 is located near the distal end of cavity 806. The sensor 850 may be formed, deposited, or otherwise attached there to the cartridge 800. In another embodiment, the sensor 850 may be a well or indentation having a bottom with sufficient transparency to allow an optical sensor to detect analytes in fluid deposited in the well or indentation. The well or indentation may also include some analyte reagent that reacts (fluoresces, changes colors, or presents other detectable qualities) when body fluid is placed in the well. In a still further embodiment, sensor 850 may be replaced with a through hole that allow fluid to pass there through. A sensor 808 on a substrate 822 may be attached to the underside of the cartridge 800, accessing fluid passing from the cavity 806 down to the sensor 808.

As mentioned above, the sensors 808 may also be placed right at the immediate vicinity or slightly setback from the module opening receiving blood so that low blood volumes will still reach the sensor. The sensors 808 may be used with low volumes such as less than about 1 microliter of sample, preferably less than about 0.6 microliter, more preferably less than about 0.3 microliter, and most preferably less than about 0.1 microliter of sample. Sensors 808 may also be directly printed or formed on the bottom of the penetrating member cartridge 800. In one embodiment, a multiplicity of miniaturized sensor fields may be placed on the floor of the radial cavity or on the microfluidic module to allow many tests on a single analyte form a single drop of blood to improve accuracy and precision of measurement. Although not limited in this manner, additional sensor fields or regions may also be included for calibration or other purposes.

Figure 79:
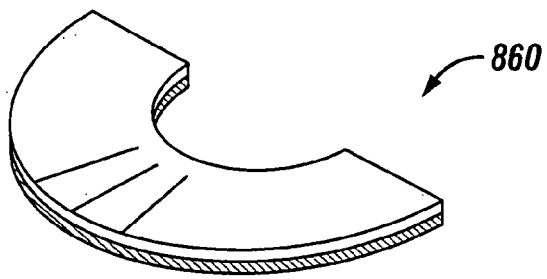
FIGS. 79-84 show optional configurations for a cartridge for use with the present invention.
Figure 80:
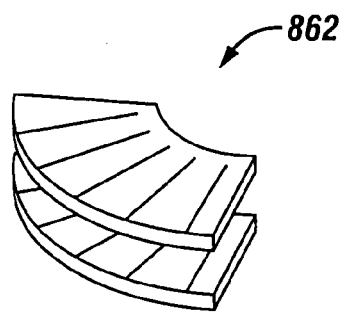
Figure 81:
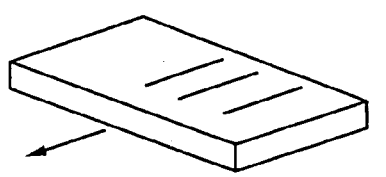
Figure 82:
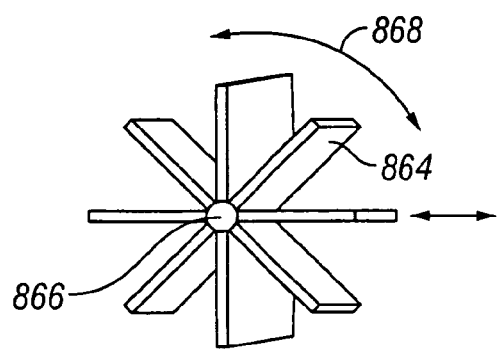
Figure 83:
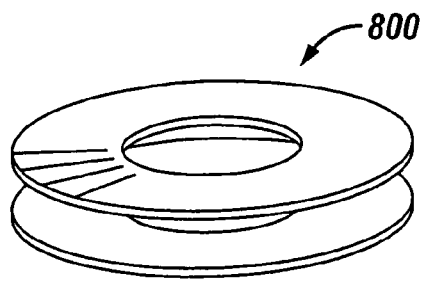
Figure 84:
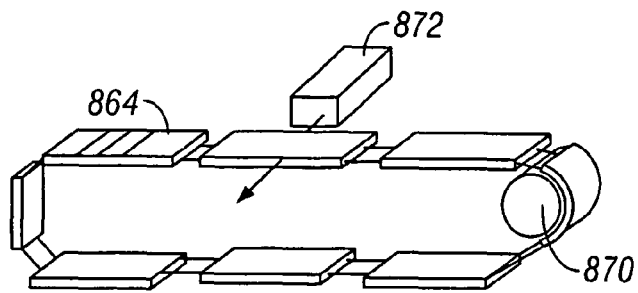

Referring now to FIGS. 79-84, further embodiments of the cartridge 800 will now be described. FIG. 79 shows a cartridge 860 having a half-circular shape. FIG. 80 shows a cartridge 862 in the shape of a partial curve. FIG. 80 also shows that the cartridges 862 may be stacked in various configurations such as vertically, horizontally, or in other orientations. FIG. 81 shows a cartridge 864 having a substantially straight, linear configuration. FIG. 82 shows a plurality of cartridges 864 arranged to extend radially outward from a center 866. Each cartridge may be on a slide (not shown for simplicity) that allows the cartridge 864 to slide radially outward to be aligned with a penetrating member launcher. After use, the cartridge 864 is slide back towards the center 866 and the entire assembly is rotated as indicated by arrow 868 to bring a new cartridge 864 into position for use with a penetrating member driver. FIG. 83 shows a still further embodiment where a plurality of cartridges 800 may be stacked for use with a penetrating member driver (see FIG. 85). The driver may be moved to align itself with each cartridge 800 or the cartridges may be moved to alight themselves with the driver. FIG. 84 shows a still further embodiment where a plurality of cartridge 864 are coupled together with a flexible support to define an array. A roller 870 may be used to move the cartridges 864 into position to be actuated by the penetrating member driver 872.

Figure 85:
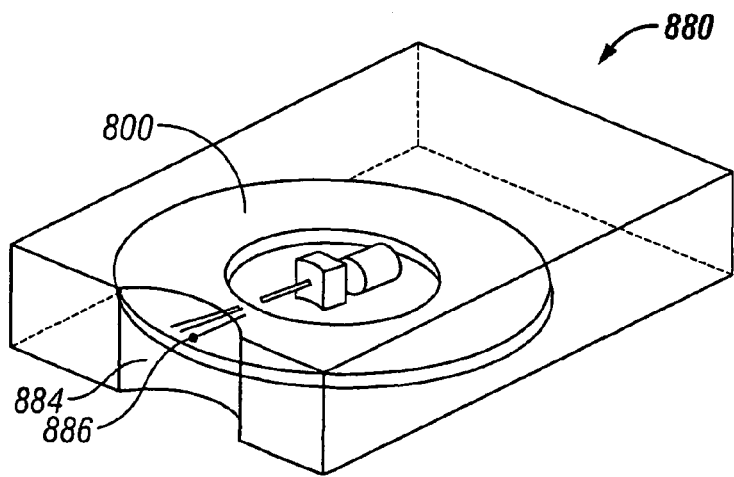
FIG. 85 shows a see-through view of one embodiment of a system according to the present invention.

Referring now to FIG. 85, one embodiment of an apparatus 880 using a radial cartridge 800 with a penetrating member driver 882 is shown. A contoured surface 884 is located near a penetrating member exit port 886, allowing for a patient to place their finger in position for lancing. Although not shown, the apparatus 880 may include a human readable or other type of visual display to relay status to the user. The display may also show measured analyte levels or other measurement or feedback to the user without the need to plug apparatus 880 or a separate test strip into a separate analyte reader device. The apparatus 880 may include a processor or other logic for actuating the penetrating member or for measuring the analyte levels. The cartridge 800 may be loaded into the apparatus 880 by opening a top housing of the apparatus which may be hinged or removably coupled to a bottom housing. The cartridge 800 may also drawn into the apparatus 880 using a loading mechanism similar in spirit to that found on a compact disc player or the like. In such an embodiment, the apparatus may have a slot (similar to a CD player in an automobile) that allows for the insertion of the cartridge 800 into the apparatus 880 which is then automatically loaded into position or otherwise seated in the apparatus for operation therein. The loading mechanism may be mechanically pow-ered or electrically powered. In some embodiments, the loading mechanism may use a loading tray in addition to the slot. The slot may be placed higher on the housing so that the cartridge 800 will have enough clearance to be loaded into the device and then dropped down over the penetrating member driver 882. The cartridge 800 may have an indicator mark or indexing device that allows the cartridge to be properly aligned by the loading mechanism or an aligning mechanism once the cartridge 800 is placed into the apparatus 880. The cartridge 800 may rest on a radial platform that rotates about the penetrating member driver 882, thus providing a method for advancing the cartridge to bring unused penetrating members to engagement with the penetrating member driver. The cartridge 800 on its underside or other surface, may shaped or contoured such as with notches, grooves, tractor holes, optical markers, or the like to facilitate handling and/or indexing of the cartridge. These shapes or surfaces may also be varied so as to indicate that the cartridge is almost out of unused penetrating members, that there are only five penetrating members left, or some other cartridge status indicator as desired.

A suitable method and apparatus for loading penetrating members has been described previously in commonly assigned, copending U.S. patent applications, and are included here by reference for all purposes. Suitable devices for engaging the penetrating members and for removing protective materials associated with the penetrating member cavity are described in commonly assigned, copending U.S. patent applications, and are included here by reference for all purposes. For example in the embodiment of FIG. 78, the foil or seal layer 820 may cover the cavity by extending across the cavity along a top surface 890 and down along the angled surface 892 to provide a sealed, sterile environment for the penetrating member and sensors therein. A piercing element described in U.S. patent applications has a piercing element and then a shaped portion behind the element which pushes the foil to the sides of the cavity or other position so that the penetrating member 802 may be actuated and body fluid may flow into the cavity.

Figure 86:
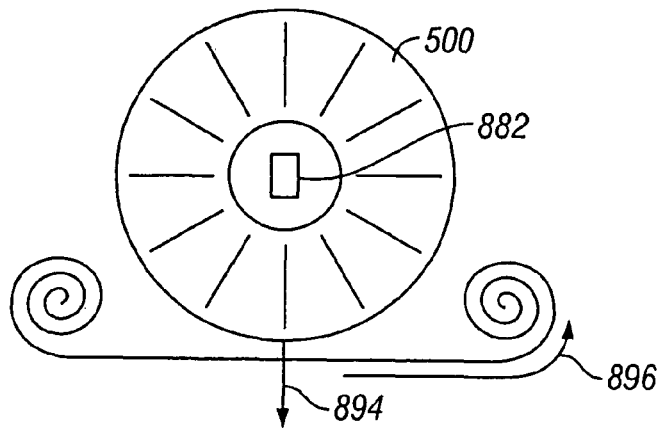
FIG. 86 is a schematic of an optional embodiment of a system according to the present invention.

Referring now to FIG. 86, a still further embodiment of a lancing system according to the present invention will be described. A radial cartridge 500 may be incorporated for use with a penetrating member driver 882. A penetrating member may be driven outward as indicated by arrow 894. A plurality of analyte sensors are presented on a roll 895 that is laid out near a penetrating member exit. The roll 895 may be advanced as indicated by arrow 896 so that used analyte sensors are moved away from the active site. The roll 895 may also be replaced by a disc holding a plurality of sensors, wherein the sensor disc (not shown) is oriented in a plane substantially orthogonal to the plane of cartridge 500. The sensor disc may also be at other angles not parallel to the plane of cartridge 500 so as to be able to rotate and present new, unused sensor in sequence with new unused penetrating members of cartridge 500.

Figure 87A:
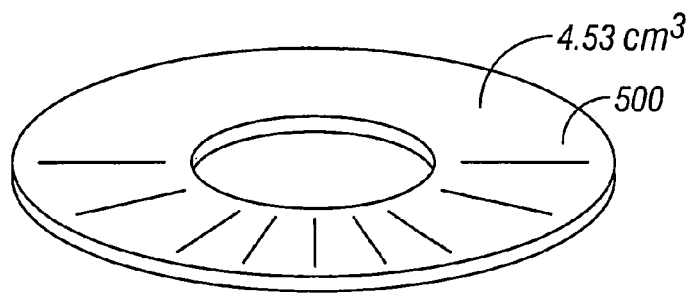
FIGS. 87A-87B show still further embodiments of cartridges according to the present invention.

Referring now to FIG. 87A, the cartridge 500 provides a high density packaging system for a lancing system. This form factor allows a patient to load a large number penetrating members through a single cartridge while maintaining a substantially handheld device. Of course such a cartridge 500 may also be used in non-handheld devices. The present cartridge 500 provide a high test density per volume of the disposable. For embodiments of a cartridge that includes sensors in addition to penetrating members such as cartridge 800, the density may also be measured in terms of density of sensors and penetrating members in a disposable. In other embodiments, the density may also be expressed in terms of sensors per disposable. For example, by taking the physical volume of one embodiment or the total envelope, this number can be divided by the number of penetrating members or number of tests. This result is the volume per penetrating member or per test in a cassetted fashion. For example, in one embodiment of the present invention, the total volume of the cartridge 500 is determined to be 4.53 cubic centimeters. In this one embodiment, the cartridge 500 holds 50 penetrating members. Dividing the volume by 50, the volume per test is arrived at 0.090 cubic centimeters. Conventional test devices such as drum is in the range of 0.720 or 0.670 cubic centimeters and that is simply the volume to hold a plurality of test strips. This does not include penetrating members as does the present embodiment 800. Thus, the present embodiment is at a substantially higher density. Even a slightly lower density device having penetrating members and sensors in the 0.500 cubic centimeter range would be a vast improvement over known devices since the numbers listed above for known devices does not include penetrating members, only packaging per test strip.

Figure 87B:
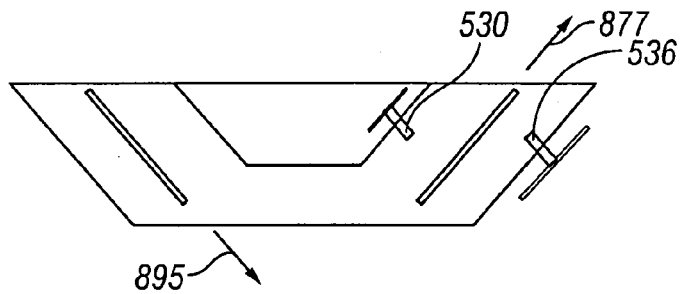

Referring now to FIG. 87B, a still further embodiment of a cartridge according to the present invention will now be described. FIG. 87B shows a cross-section of a conical shaped cartridge with the penetrating member being oriented in one embodiment to move radially outward as indicated by arrow 897. In another embodiment, the penetrating member may be oriented to move radially inward as indicated by arrow 895. The gripper may be positioned to engage the penetrating member from an inner surface or an outer surface of the cartridge.

Figure 88:
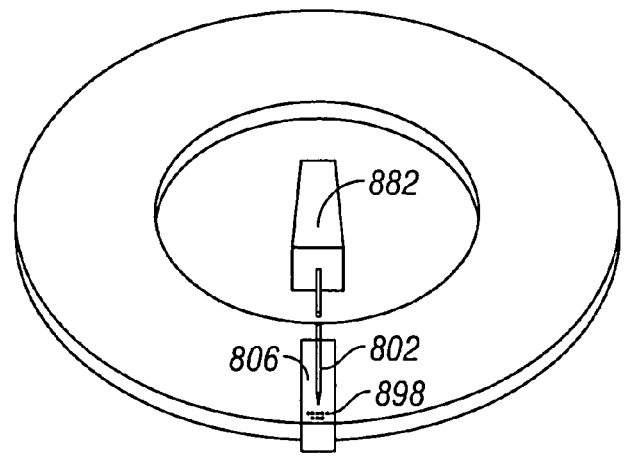
FIG. 88 shows a cartridge having an array of analyte sensors.

Referring now to FIG. 88, nanowires may also be used to create low volume sensors used with the cartridge 800. Further details of a nanowire device is described in commonly assigned, copending U.S. Provisional Patent Application Ser. No. 60/433,286 filed Dec. 13, 2002, fully incorporated herein by reference for all purposes. These nanowire sensors 898 may be incorporated into the cavity 806 housing the penetrating member 802. They may be placed on the floor or bottom surface of the cavity 806, on the wall, on the top surface, or any combinations of some or all of these possibilities. The sensors 898 may be designed to have different sensitivity ranges so as to enhance the overall sensitivity of an array of such sensors. Methods to achieve this may include, but are not limited to, using nanowires of varying sizes, varying the number of nanowires, or varying the amount of glucose oxidase or other glucose detection material on the nanowires. These nanowire sensors may be designed to use low volumes of body fluid for each sample, due to their size. In some embodiments, each of the sensors are accurate using volumes of body fluid sample less than about 500 nanoliters. In some embodiments, each of the sensors are accurate using volumes of body fluid sample less than about 300 nanoliters. In still other embodiments, each sensor is accurate with less than about 50 nanoliters, less than about 30 nanoliters, less than about 10 nanoliters, less than about 5 nanoliters, and less than about 1 nanoliters of body fluid sample. In some embodiments, the combined array of sensors uses less than 300 nanoliters of body fluid to arrive at an analyte measurement.

Figure 89:
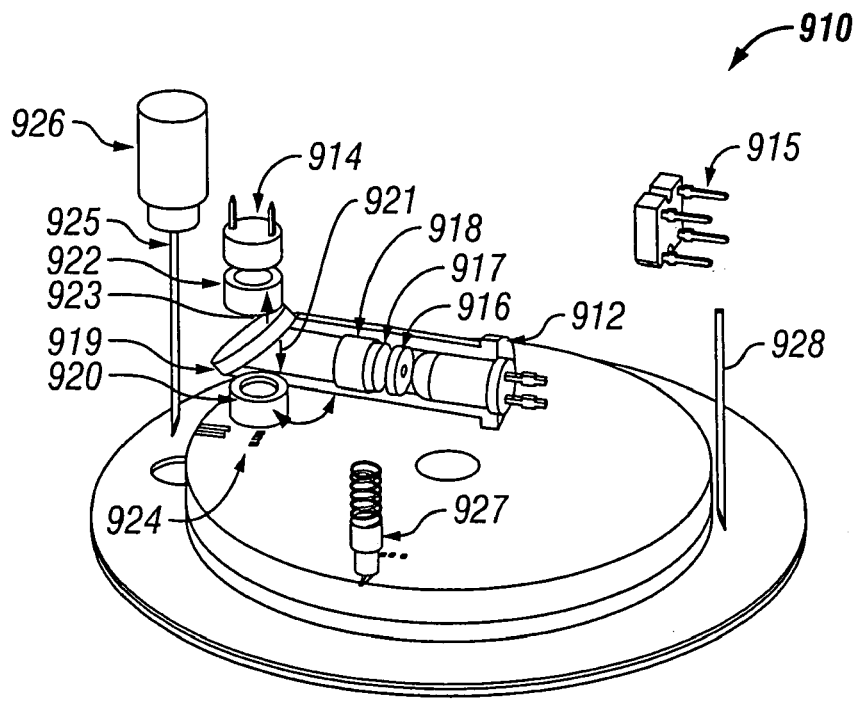
FIGS. 89-90 show embodiments of illumination systems for use with the present invention.

Referring now to FIG. 89, a still further embodiment of the present invention will be described. FIG. 89 shows one embodiment of an optical illumination system 910 for use with optical analyte sensors (FIG. 91) that may be in contact with a body fluid sample. The overall system may include a plurality of analyte sensors which provide some optical indicator, a light source 912 for providing light to shine on the sensors, at least one light detector 914, and a processor (not shown). The sensor or sensors are exposed to a sample of the fluid of unknown composition. A plurality of sensors may be arranged into an array of sensors exposed to one fluid sample, each group targeting a specific analyte and may contain an analyte-specific chemical that interacts more specifically with one analyte than with some other analytes to be analyzed. Each sensor may also have different sensitivity ranges so as to maximize overall sensitivity of an array of such sensors. The light source 912 shines light on at least one sensor to cause light interaction. The differences in the sensors may lead to differences in the light interaction. The light detector detects the light interaction by the sensors. The processor analyzes the light interaction by the sensors to take into account interference in light interaction among the analytes, thereby determining the concentration of the desired analyte in the fluid.

Figure 91:
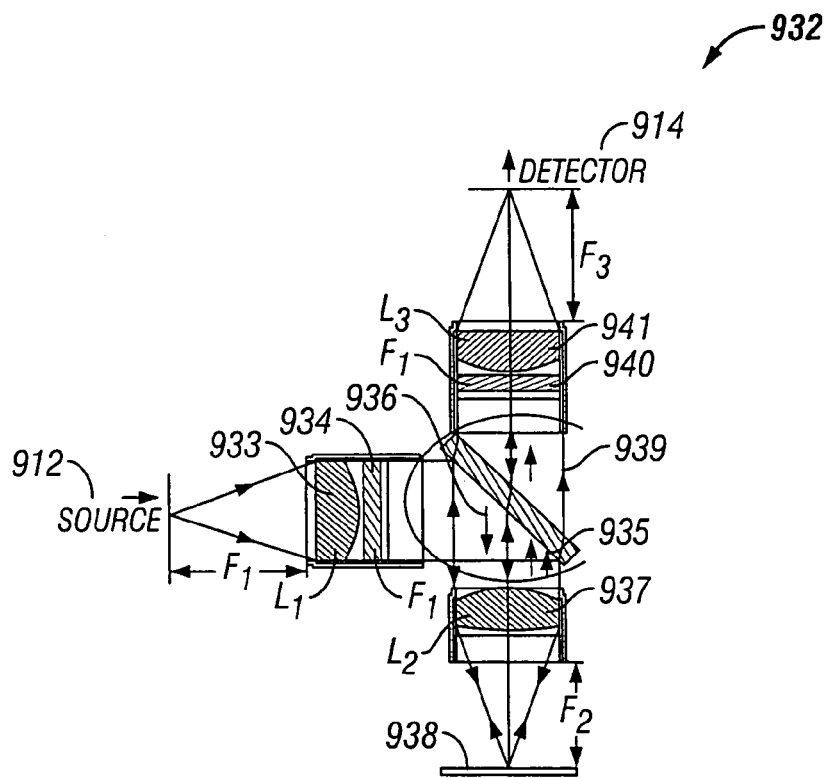
FIG. 91 shows a cross-section of an embodiment of an illumination system.

Referring still to the embodiment of FIG. 89, the light source 912 may be but is not limited to an LED. An alternative LED 915 may also be used with the present invention. Light, illumination, or excitation energy from LED 912 travels along a path through a pinhole 916, a filter 917, and a lens 918. The light then comes into contact with a beamsplitter 919 such as a dichroic mirror or other device useful for beamsplitting. The light is then directed towards lens 920 as indicated by arrow 921. The lens 920 focuses light onto the sensor (FIG. 91). This excitation energy may cause a detectable optical indicator from the sensor. By way of example and not limitation, fluorescence energy may be reflected bay up the lens 920. This energy passes through the beamsplitter 919 and to lens 922 which is then received by detector 914 as indicated by arrow 923. The detector 914 measures the energy and this information is passed on to the processor (not shown) to determine analyte levels. The illumination system 910 may also include cells 924 on the disc surface. In this specific embodiment, a penetrating member 925 drive by a force generator 926 such as but not limited to a solenoid may be used to obtain the fluid sample. A detent 927 may also be included with the device along with other bare lancets or penetrating members 928.

Figure 90:
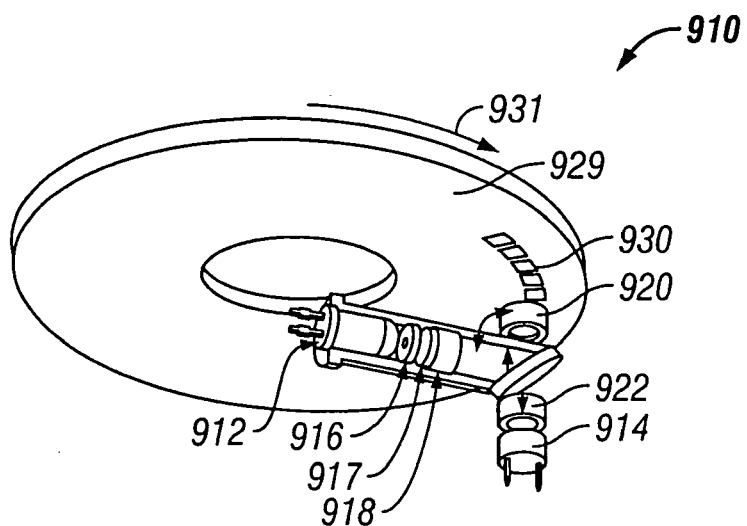

Referring now to FIG. 90, another embodiment of the illumination system 910 is shown for use with a cartridge 929. Cartridge 929 is similar to cartridge 800. Cartridge 929 is a single cartridge having a plurality of penetrating members and a plurality of optical sensors (not shown). The cartridge 929 further includes a plurality of optically transparent portions 930 which may be but is not limited to windows or the like for the light from LED 912 to shine into a cavity of the cartridge 929. In one embodiment, each cavity of the cartridge 929 may include at least one transparent portion 930. This allows the light to generate energy that may be read by sensor 914. The cartridge 929 may be used a driver 882 to actuate penetrating members and the cartridge 929 may rotate as indicated by arrow 931.

Referring now to FIG. 91, a cross-section of a similar embodiment of the illumination system is shown. This system 932 has source 912 with a lens 933 having an excitation filter 934. This excitation filter 934, in one embodiment, only allows excitation energy to pass. This filter 934 allows the excitation energy to pass to dichroic mirror 935, but does not let it return to source 912. Excitation energy is reflected down as indicated by arrow 936. Lens 937 focuses the energy to optical analyte sensor 938. Fluorescence energy 939 passes through the dichroic mirror 935 and towards a fluorescent filter 940. In one embodiment, the fluorescent filter 940 only allows fluorescent energy to pass through to lens 941. Thus, the detector 914 only receives fluorescent energy from the sensor 938. It should be understood of course, that the filter may be changed to allow the type of energy being generated by sensor 938 to pass. In some embodiments, no filter may be used. The dichroic mirror 935 may be a Bk7 substrate, 63×40×8 mm. The filters may also be a Bk7 substrate about 40 mm in diameter and about 6 mm thick. The lens 933, 937, and 941 may be achromat:bfl=53.6, working aperture 38 mm.

Figure 92:
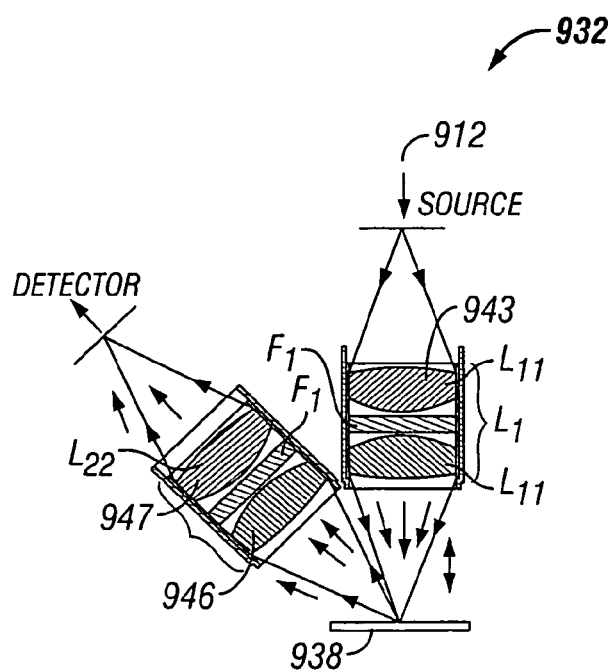
FIG. 92 shows a still further embodiment of an illumination system.

Referring now to FIG. 92, a still further embodiment of an illumination system 942 will be described. This system does not use a beamsplitter or dichroic mirror. Instead, both the source or LED 912 and detector 914 have direct line of sight to the optical analyte sensor 938. In this embodiment, multiple elements are combined into a single housing. For example, lens 943, lens 944, and filter 945 are combined while lens 946, lens 947, and filter 948 are also combined.

Figure 93:
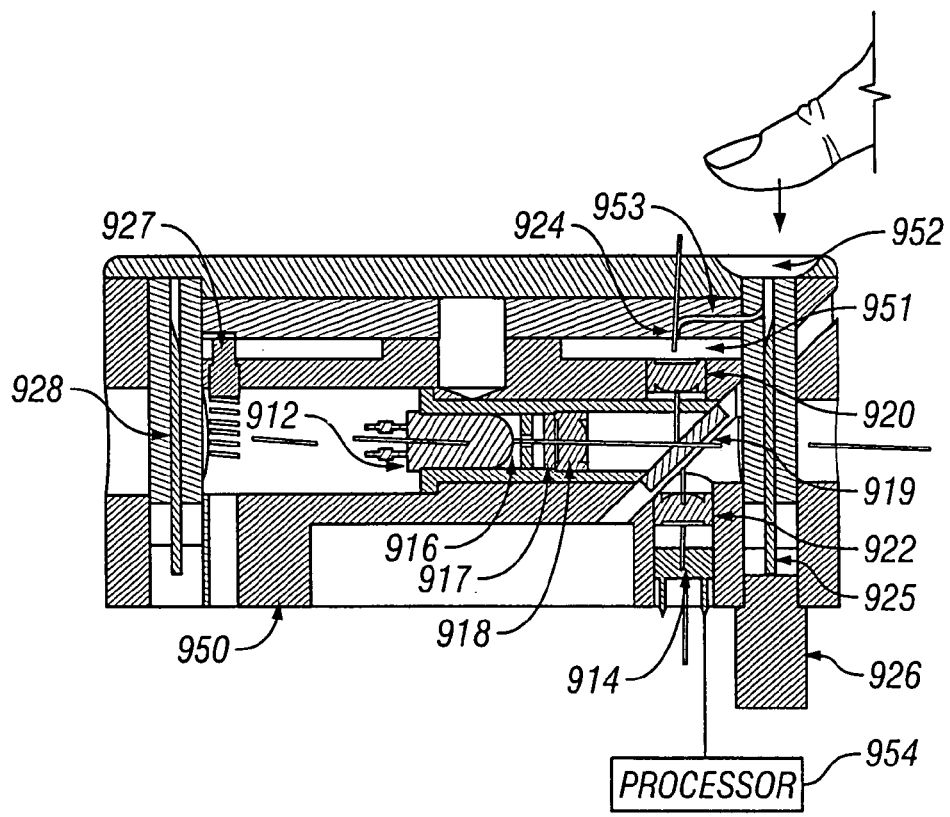
FIG. 93 shows a cross-section of a system similar to that of FIG. 89 in a housing.

Referring now to FIG. 93, a cross-section of a system similar to that of FIG. 89 is shown in a housing 950. LED 912 sends light to mirror 919 to a light path 951 to cells 924 on a surface of the disc. A finger access 952 allows a sample to be obtained and flow along a fluid pathway 953 to be analyzed. A processor 954 may be coupled to detector 914 to analyze the results.

Figure 94:
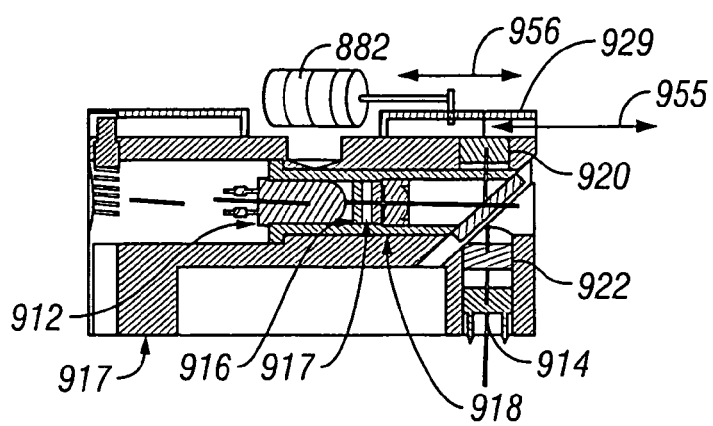
FIG. 94 shows a cross-section of a system similar to that of FIG. 90.
Figure 95:
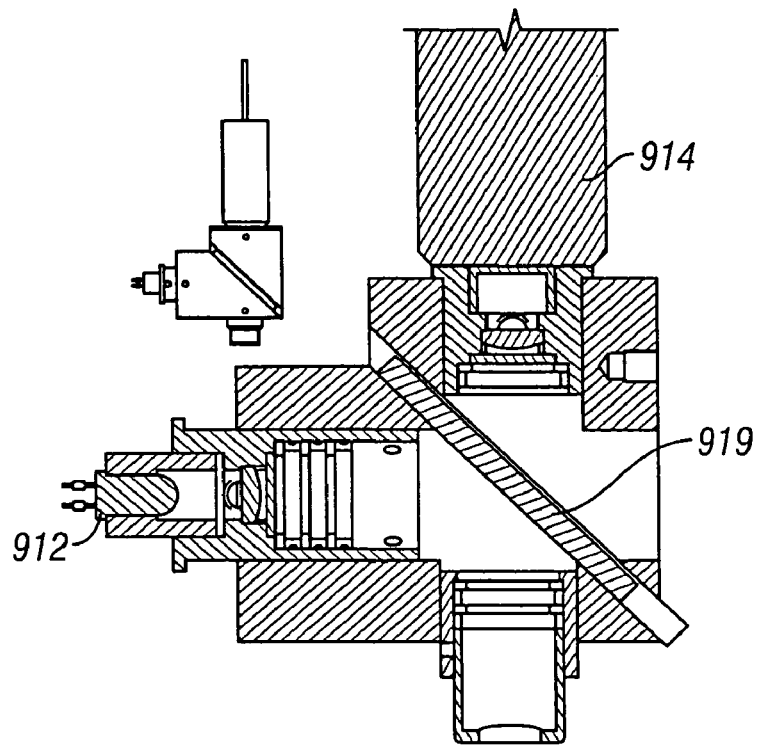
FIGS. 95 and 96 show further views of a system similar to that of FIG. 89, which include additional lenses or filters as may be useful to refine energy detection.
Figure 96:
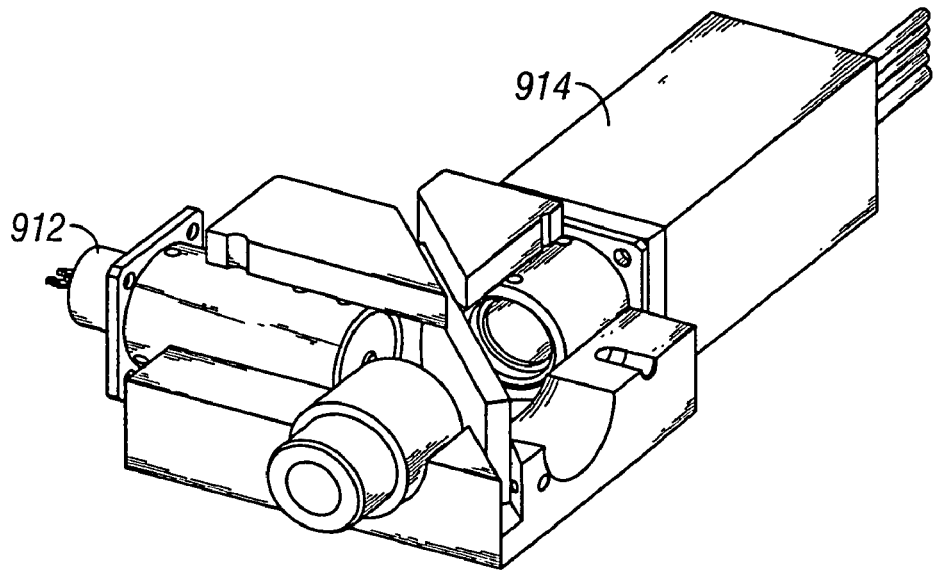

Referring now to FIG. 94, a cross-section of a system similar to that of FIG. 90 will be further described. This shows a cartridge 929 used with a driver 882. This allows for a radial design where the penetrating members extend radially outward as indicated by arrow 955. The driver 882 may have a coupler portion that reciprocates as indicated by arrow 956. FIGS. 95 and 96 provide further views of a system similar to that of FIG. 89. The embodiment of FIGS. 95 and 96 may include additional lenses or filters as may be useful to refine energy detection.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, sensors may be printed on the top, bottom, or side of the cavities. The front end of the cartridge may be in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue.

Any of the features described in this application or any reference disclosed herein may be adapted for use with any embodiment of the present invention. For example, the devices of the present invention may also be combined for use with injection penetrating members or needles as described in commonly assigned, copending U.S. patent application Ser. No. 10/127,395 filed Apr. 19, 2002. A sensor to detect the presence of foil may also be included in the lancing apparatus. For example, if a cavity has been used before, the foil or sterility barrier will be punched. The sensor can detect if the cavity is fresh or not based on the status of the barrier. It should be understood that in optional embodiments, the sterility barrier may be designed to pierce a sterility barrier of thickness that does not dull a tip of the penetrating member. The lancing apparatus may also use improved drive mechanisms. For example, a solenoid force generator may be improved to try to increase the amount of force the solenoid can generate for a given current. A solenoid for use with the present invention may have five coils and in the present embodiment the slug is roughly the size of two coils. One change is to increase the thickness of the outer metal shell or windings surround the coils. By increasing the thickness, the flux will also be increased. The slug may be split; two smaller slugs may also be used and offset by ½ of a coil pitch. This allows more slugs to be approaching a coil where it could be accelerated. This creates more events where a slug is approaching a coil, creating a more efficient system.

In another optional alternative embodiment, a gripper in the inner end of the protective cavity may hold the penetrating member during shipment and after use, eliminating the feature of using the foil, protective end, or other part to retain the used penetrating member. Some other advantages of the disclosed embodiments and features of additional embodiments include: same mechanism for transferring the used penetrating members to a storage area; a high number of penetrating members such as 25, 50, 75, 100, 500, or more penetrating members may be put on a disk or cartridge; molded body about a lancet becomes unnecessary; manufacturing of multiple penetrating member devices is simplified through the use of cartridges; handling is possible of bare rods metal wires, without any additional structural features, to actuate them into tissue; maintaining extreme (better than 50 micron—lateral—and better than 20 micron vertical) precision in guiding; and storage system for new and used penetrating members, with individual cavities/slots is provided. The housing of the lancing device may also be sized to be ergonomically pleasing. In one embodiment, the device has a width of about 56 mm, a length of about 105 mm and a thickness of about 15 mm. Additionally, some embodiments of the present invention may be used with non-electrical force generators or drive mechanism. For example, the punch device and methods for releasing the penetrating members from sterile enclosures could be adapted for use with spring based launchers. The gripper using a frictional coupling may also be adapted for use with other drive technologies.

Still further optional features may be included with the present invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). The penetrating members may be a bare penetrating member during launch. The same driver may be used for advancing and retraction of the penetrating member. Different sensors detecting different ranges of glucose concentration, different analytes, or the like may be combined for use with each penetrating member. Non-potentiometric measurement techniques may also be used for analyte detection. For example, direct electron transfer of glucose oxidase molecules adsorbed onto carbon nanotube powder microelectrode may be used to measure glucose levels. In all methods, nanoscopic wire growth can be carried out via chemical vapor deposition (CVD). In all of the embodiments of the invention, preferred nanoscopic wires may be nanotubes. Any method useful for depositing a glucose oxidase or other analyte detection material on a nanowire or nanotube may be used with the present invention. This application cross-references commonly assigned copending U.S. patent application Ser. No. 10/323,623 filed Dec. 18, 2002; commonly assigned copending U.S. patent application Ser. No. 10/323,624 filed Dec. 18, 2002; and commonly assigned copending U.S. patent application Ser. No. 10/324,053 filed Dec. 18, 2002. All applications listed above are fully incorporated herein by reference for all purposes. Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A device for use in penetrating tissue to obtain a body fluid sample, comprising:
   a disposable;
   a plurality of penetrating members positioned in said disposable and each of a penetrating member being housing in an associated chamber in the disposable, each of said penetrating members having a distal end sufficiently sharp to pierce tissue, each of said penetrating members being moveable relative to the other ones of the penetrating members so that the sharpened distal ends extend radially outward to penetrate tissue; and
   wherein said penetrating members are elongate members without molded attachments, each of a penetrating member being coupled to a penetrating member driver with a coupler that couples a penetrating member to the penetrating member driver when the penetrating member is positioned in its associated chamber, and
   a plurality of ratchet surfaces near an inner radial surface of the disposable.

2. The device of claim 1 wherein said disposable defines a plane and said penetrating members are contained in substantially the same plane.

3. The device of claim 1 wherein said disposable defines a plane and said penetrating members are oriented to extend radially outward in substantially the same plane as the disposable.

4. The device of claim 1 wherein said penetrating members are substantially in a common plane.

5. The device of claim 1 wherein said penetrating members are arranged in a radial pattern.

6. The device of claim 1 wherein said penetrating members are coated with a material.

7. The device of claim 1 wherein said penetrating members are coated with a material selected from the following: Teflon, glass, silicon, or polymer.

8. The device of claim 1 wherein said disposable has a flat radial configuration.

9. The device of claim 1 wherein said disposable comprises a disc-shaped housing.

10. The device of claim 1 wherein said disposable has a plurality of cavities housing said lancets.

11. The device of claim 1 wherein said disposable has a plurality of grooves housing said lancets.

12. The device of claim 1 wherein said disposable comprises a disc-shaped housing with a non-chamfered outer periphery.

13. A device comprising:
    a single radial disposable;
    a plurality of penetrating members without molded attachments slidably positioned in said disposable and selectively actuatable to penetrate tissue, each of said penetrating members without molded attachments having an longitudinal axis;
    wherein the penetrating members without molded attachments are longitudinally oriented to be substantially in a common plane, each of the penetrating members without molded attachments being positioned in an associated chamber in the disposable and encased with a sterility seal, each of the penetrating member without molded attachment being coupled to a penetrating member driver with a coupler and
    a plurality of ratchet surfaces near an inner radial surface of the disposable.

* * * * *